United States Patent
Tieger et al.

(10) Patent No.: US 10,532,981 B2
(45) Date of Patent: Jan. 14, 2020

(54) CRYSTALLINE MODIFICATIONS OF METHYL (3Z)-3-{[(4-{METHYL[(4-METHYLPIPERAZIN-1-YL)ACETYL]AMINO}PHENYL)AMINO](PHENYL)METHYLIDENE}-2-OXO-2,3-DIHYDRO-1H-INDOLE-6-CARBOXYLATE SALTS AND METHODS OF PREPARATION THEREOF

(71) Applicant: Zentiva k.s., Prague (CZ)

(72) Inventors: Eszter Tieger, Magyarlak (HU);
Marcela Tkadlecova, Prague (CZ);
Ondrej Dammer, Hostivice (CZ);
Tomas Gurgut, Prague (CZ)

(73) Assignee: Zentiva k.s., Prague (CZ)

( * ) Notice: Subject to any disclaimer, the term of this patent is extended or adjusted under 35 U.S.C. 154(b) by 0 days.

(21) Appl. No.: 16/077,475

(22) PCT Filed: Feb. 20, 2017

(86) PCT No.: PCT/CZ2017/000008
§ 371 (c)(1),
(2) Date: Aug. 12, 2018

(87) PCT Pub. No.: WO2017/144029
PCT Pub. Date: Aug. 31, 2017

(65) Prior Publication Data
US 2019/0055197 A1 Feb. 21, 2019

(30) Foreign Application Priority Data
Feb. 24, 2016 (CZ) .................... 2016-104

(51) Int. Cl.
*C07D 209/34* (2006.01)
(52) U.S. Cl.
CPC ........ *C07D 209/34* (2013.01); *C07B 2200/13* (2013.01)
(58) Field of Classification Search
CPC .................................................. C07D 209/34
See application file for complete search history.

(56) References Cited

U.S. PATENT DOCUMENTS 7,700,617 B2 * 4/2010 Kim ................... A61K 31/4375
514/300

2014/0051713 A1 * 2/2014 Gidwani .............. C07D 405/12
514/266.24

FOREIGN PATENT DOCUMENTS

WO  WO 2007/141283  12/2007
WO  WO 2012/068441  5/2012

OTHER PUBLICATIONS

Kakkar et al. Drug Development and Industrial Pharmacy, 23(11), p. 1063-1067 (Year: 1997).*
Hilfiker et al, 2006, "Relevance of Solid-state Properties for Pharmaceutical products", pp. 1-19, XP002525043, ISBN:978-3-527-31146-0.

* cited by examiner

*Primary Examiner* — Emily A Bernhardt
(74) *Attorney, Agent, or Firm* — Pearl Cohen Zedek Latzer Baratz LLP

(57) ABSTRACT

The compounds are crystalline modifications of methyl (3Z)-3-{[4-{methyl[(4-methylpiperazin-1-yl)acetyl]amino}phenyl)amino](phenyl)methylidene}-2-oxo-2,3-dihydro-1H-indole-6-carboxylate salts of Formula I, wherein H—X represents at least one acid component, processes for the preparation thereof, and pharmaceutical compositions.

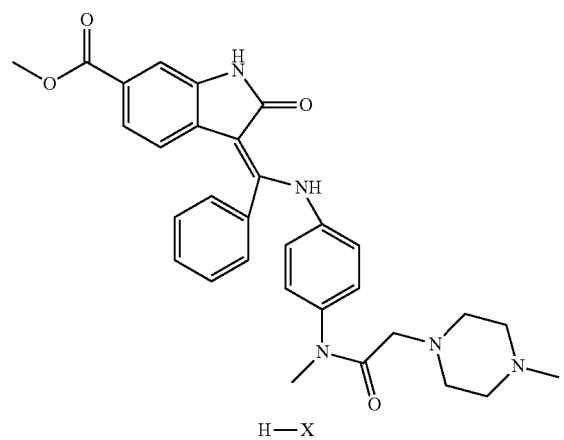

2 Claims, 48 Drawing Sheets

CRYSTALLINE MODIFICATIONS OF METHYL (3Z)-3-{[(4-{METHYL[(4-METHYLPIPERAZIN-1-YL)ACETYL]AMINO}PHENYL)AMINO](PHENYL)METHYLIDENE}-2-OXO-2,3-DIHYDRO-1H-INDOLE-6-CARBOXYLATE SALTS AND METHODS OF PREPARATION THEREOF

CROSS-REFERENCE TO RELATED APPLICATIONS

This application is a National Phase Application of PCT International Application No. PCT/CZ2017/000008 International Filing Date Feb. 20, 2017, claiming priority of the Czech Patent Application No. PV 2016-104, filed Feb. 24, 2016, which is hereby incorporated by reference.

FIELD OF THE INVENTION

The present invention relates to crystalline modifications of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate salts of Formula I,

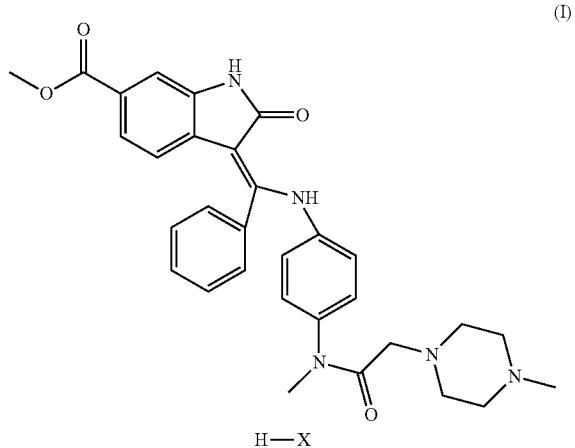

(I)

wherein HX represents at least one acid component, preferably methanesulfonic acid, p-toluenesulphonic acid, L-tartaric acid, maleic acid, acetic acid and phosphoric acid. The invention also relates to the processes for the preparation thereof as well as said use thereof in pharmaceutically acceptable compositions. Use of said crystalline forms of intedanib and manufactured salts in the preparation of methyl (3Z)-3-{[(4-{methyl[(4-methylpiperazin-1-yl)acetyl]amino}phenyl)amino]-(phenyl)methylidene}-2-oxo-2,3-dihydro-1H-indole-6-carboxylate in the form of any pharmaceutically acceptable salt thereof is also part of this invention.

BACKGROUND ART

Methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate compound which is also known as intedanib (CAS no.: 656247-17-5) has a selective inhibitor activity on the tyrosine-kinase enzymes targeting vascular endothelial growth factor receptor (VEGFR), fibroblast growth factor receptor (FGFR) and platelet derived growth factor receptor (PDGFR). It is a drug indicated for the treatment of idiopathic pulmonary fibrosis (IPF) and for some types of non-small-cell lung cancer. The enzymes tyrosine kinases are responsible for the activation of many proteins by signal transduction cascades. The proteins are activated by adding a phosphate group to the protein (phosphorylation), a step that TKIs inhibit. TKIs are typically used as anticancer drugs.

WO0127081 describes protein kinase inhibitors with valuable pharmacological effect in the treatment of related diseases. One example of the compounds disclosed is methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate.

Crystalline modification of intedanib was described in WO2004013099 which describes intedanib monoethanesulphonate hemihydrate and preparation thereof with valuable pharmacological effect in the treatment of related diseases and excessive or abnormal cell proliferation.

Salts of intedanib prepared with hydrochloric acid, hydrobromic acid, phosphoric acid, sulphuric acid, methanesulfonic acid, ethanedisulfuric acid, isethionic acid, benzenesulfonic acid, p-toluenesulfonic acid, camphorsulfonic acid, naphtalene-1,5-disulfonic acid, citric acid, D- and L-tartaric acid, fumaric acid, maleic acid, L-lactic acid, glycolic acid, glycine, L- and D-malic acid, malonic acid, oxalic acid, succinic acid, gentisic acid, camphoric acid, benzoic acid, mandelic acid, saccharic acid, salicylic acid, L-aspartic acid, ascorbic acid and xinafoic acid are disclosed in WO2007141283. Following WO2012068441 discloses salts of intedanib prepared with formic acid, adipic acid, acetic acid, ethanesulfonic acid and orotic acid.

Many solid pharmaceutical compounds can exist in various crystalline forms regarded as polymorphs and hydrates/solvates having different crystal structures and hence different physico-chemical properties including melting point, solubility, dissolution rate and finally, bioavailability. In order to distinguish the distinct solid phases of a compound several solid state analytical techniques can be used, e.g. X-Ray Powder Diffraction, solid state NMR and Raman spectroscopy, thermoanalytical methods.

Discovery of new solid phases (polymorphs, solvates and hydrates) of an active pharmaceutical compound offers the opportunity to find the appropriate modification having desirable physico-chemical properties and processability and improves the characteristics of the pharmaceutical product. For this reason there is an explicit need for new solid forms (polymorphs, solvates, hydrates) of intedanib and salts thereof especially in the crystalline form.

DISCLOSURE OF THE INVENTION

The object of the present invention is to create novel crystal modifications of salts comprising methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate of Formula I and at least one acid component (HX) suitable for oral administration which will meet the pharmaceutical requirements

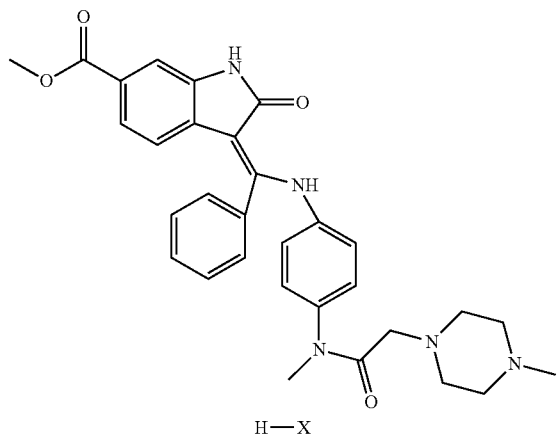

(I)

wherein HX represents at least one acid component, preferably methanesulphonic acid, p-toluenesulphonic acid, L-tartaric acid, maleic acid, acetic acid and phosphoric acid.

In some embodiments of this invention, the solid forms are characterized by a variety of solid state analytical data, including for example X-ray powder diffraction pattern (XRPD) and differential scanning calorimetry (DSC) curve.

The subject of the invention is the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt of Formula I, wherein X represents monomethanesulfonate, having an X-ray powder diffraction pattern comprising characteristic peaks at about 9.8; 14.1; 17.2; 20.0 and 22.8°±0.2° 2-theta measured by CuKα radiation. In some embodiments the Crystal modification 1 is characterised by differential scanning calorimetry curve having a melting process with $T_{desolvation1}=107.9°$ C., $T_{desolvation2}=175.6°$ C., $T_{peak}=314.6°$ C. In some embodiments the Crystal modification 1 is characterised by the thermal gravimetric curve having a 1.69% weight loss in the range of 25° C. to 110° C.

It should be understood that relative intensity can vary depending on a number of factors, including sample preparation and mounting, the instrument and analytical procedure and settings used to obtain the spectrum.

Another object of the invention is a process for the preparation of the Crystal modification 1 of intedanib methanesulfonate wherein intedanib free base is suspended in a polar protic solvent and methanesulfonic acid is then added, preferably the polar protic solvent is at the temperature of 60° C., preferably followed by heating of the system to a temperature 60° C. followed by the addition of the aqueous solution of the counterion, resulting in a clear solution, kept at the temperature of 60° C. for additional 1 hour, then slowly cooled to a temperature of 44° C. where it is seeded and finally cooled to 0-5° C. The polar protic solvent is selected from the group consisting of methanol, ethanol, 1-propanol, 2-propanol, 1-butanol, 2-butanol or a mixture thereof, more preferably the suitable polar protic solvent is methanol, more preferably it is methanol at the temperature of 60° C.

In some embodiments the process for the preparation of the Crystal modification 1 of intedanib methanesulfonate comprises the following steps: a/ suspending intedanib free base in a polar protic solvent selected from the group consisting of: methanol, ethanol, 1-propanol, 2-propanol, 1-butanol, 2-butanol or a mixture thereof, more preferably in methanol at the temperature of 60° C.; b/ drop-wise addition of the aqueous solution of the methanesulfonic acid >98%, resulting in a clear solution; c/ stirring the solution of the step b/ at 60° C. for additional 1 hour; d/ cooling the solution of step c/ to a temperature of 44° C. wherein the seeding is performed and precipitation occurs; e/ cooling the suspension of step d/ to 0-5° C.; f/ keeping the suspension of step e/ for 16 hours at a temperature of 0-5° C.; g/ isolating the intedanib methanesulfonic acid salt in Crystal modification 1 and h/ optionally, drying the product of step g/ under the laboratory conditions until the constant weight of the product is reached.

The object of the invention is the Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt of Formula I, wherein X represents bis-methanesulfonate, having an X-ray powder diffraction pattern comprising characteristic peaks at about 4.0; 10.7; 14.1; 18.1; 20.6 and 22.8±0.2° 2-theta measured by CuKα radiation. In some embodiments the Crystal modification 2 is characterised by differential scanning calorimetry curve having a melting process with $T_{peak}=255.9°$ C. In some embodiments the Crystal modification 1 is characterised by the thermal gravimetric curve having a 2.53% weight loss in the range of 25° C. to 229° C.

It should be understood that relative intensity can vary depending on a number of factors, including sample preparation and mounting, the instrument and analytical procedure and settings used to obtain the spectrum.

Another object of the invention is a process for the preparation of the Crystal modification 2 of intedanib methanesulfonate wherein intedanib free base is suspended in a polar protic solvent and 2 molar equivalent of methanesulfonic acid is then added, preferably the polar protic solvent is at the temperature of 50° C., preferably followed by heating of the system to a temperature 50° C. followed by the addition of the counterion, kept at the temperature of 50° C. for additional 1 hour, then slowly cooled to the temperature of 0-5° C. The polar protic solvent is selected from the group consisting of methanol, ethanol, 1-propanol, 2-propanol, 1-butanol, 2-butanol or a mixture thereof, preferably the suitable polar protic solvent is methanol, preferably it is methanol at the temperature of 50° C.

In some embodiments the process for the preparation of the Crystal modification 2 of intedanib methanesulfonate comprises the following steps: a/ suspending intedanib free base in a polar protic solvent selected from the group consisting of: methanol, ethanol, 1-propanol, 2-propanol, 1-butanol, 2-butanol or a mixture thereof, more preferably in methanol at the temperature of 50° C.; b/ drop-wise addition of the aqueous solution of the methanesulfonic acid >98% when precipitation occurred; c/ stirring the suspension of step b/ at 50° C. for additional 1 hour; d/ cooling the suspension of step c/to a temperature of 0-5° C.; e/ keeping the suspension of step d/ for 16 hours at a temperature of 0-5° C.; f/ isolating the intedanib methanesulfonic acid salt in Crystal modification 2 and g/ optionally, drying the product of step f/ under the laboratory conditions until the constant weight of the product is reached.

The object of the invention is the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt of Formula I, wherein X represents tosylate, having an X-ray powder diffraction pattern comprising characteristic peaks at about 8.3; 9.5; 13.6; 17.9 and 20.4±0.2° 2-theta measured by CuKα radiation. In some embodiments the Crystal modification 1 is characterised by differential scanning calorimetry curve having a melting process with $T_{peak}$=254.6° C. In some embodiments the Crystal modification 1 is characterised by the thermal gravimetric curve having a 0.85% weight loss in the range of 25° C. to 265° C.

It should be understood that relative intensity can vary depending on a number of factors, including sample preparation and mounting, the instrument and analytical procedure and settings used to obtain the spectrum.

Another object of the invention is a process for the preparation of the Crystal modification 1 of intedanib tosylate wherein intedanib free base is suspended in a polar aprotic solvent and p-toluenesulfonic acid is then added, preferably the polar aprotic solvent is methyl ethyl ketone at the temperature of 50° C., preferably followed by heating of the system to a temperature 50° C. followed by the addition of the counterion, kept at the temperature of 50° C. for additional 1 hour, then slowly cooled to the temperature of 0-5° C. The polar aprotic solvent is selected from the group consisting of methyl-acetate, ethyl-acetate, butyl-acetate, acetonitrile, acetone, methyl ethyl ketone or a mixture thereof, more preferably the suitable polar aprotic solvent is methyl ethyl ketone, more preferably it is methyl ethyl ketone at the temperature of 50° C.

In some embodiments the process for the preparation of the Crystal modification 1 of intedanib tosylate comprises the following steps: a/ suspending intedanib free base in a polar aprotic solvent selected from the group consisting of: methyl-acetate, ethyl-acetate, butyl-acetate, acetonitrile, acetone, methyl ethyl ketone or a mixture thereof, more preferably in methyl ethyl ketone at the temperature of 50° C.; b/ drop-wise addition of the solution of the p-toluenesulfonic acid when dissolution and precipitation occurred; c/ stirring the suspension of step b/ at 50° C. for additional 1 hour; d/ cooling the suspension of step c/ to a temperature of 0-5° C.; e/ keeping the suspension of step d/ for 16 hours at a temperature of 0-5° C.; f/ isolating the intedanib p-toluenesulfonic acid salt in Crystal modification 1 and g/ optionally, drying the product of step f/ under the laboratory conditions until the constant weight of the product is reached.

The object of the invention is the Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt of Formula I, wherein X represents tosylate, having an X-ray powder diffraction pattern comprising characteristic peaks at about 7.2; 13.6; 16.0; 18.0; 20.0 and 25.2±0.2° 2-theta measured by CuKα radiation. In some embodiments the Crystal modification 2 is characterised by differential scanning calorimetry curve having a melting process with $T_{desolvation}$=77.7° C. and $T_{peak}$=236.9° C. In some embodiments the Crystal modification 2 is characterised by the thermal gravimetric curve having a 1.5% weight loss in the range of 25° C. to 68° C.

It should be understood that relative intensity can vary depending on a number of factors, including sample preparation and mounting, the instrument and analytical procedure and settings used to obtain the spectrum.

Another object of the invention is a process for the preparation of the Crystal modification 2 of intedanib tosylate wherein intedanib free base is suspended in a polar protic solvent and p-toluenesulfonic acid is then added, preferably the polar protic solvent is at the temperature of 50° C., preferably followed by heating of the system to a temperature 50° C. followed by the addition of the counterion, kept at the temperature of 50° C. for additional 1 hour, then slowly cooled to the temperature of 0-5° C. The polar protic solvent is selected from the group consisting of methanol, ethanol, 1-propanol, 2-propanol, 1-butanol, 2-butanol or a mixture thereof, preferably the polar protic solvent is methanol or ethanol, more preferably it is ethanol at the temperature of 50° C.

In some embodiments the process for the preparation of the Crystal modification 2 of intedanib tosylate comprises the following steps: a/ suspending intedanib free base in a polar protic solvent selected from the group consisting of: methanol, ethanol, 1-propanol, 2-propanol, 1-butanol, 2-butanol or a mixture thereof, more preferably in ethanol at the temperature of 50° C.; b/ drop-wise addition of the solution of the p-toluenesulfonic acid when dissolution and precipitation occurred; c/ stirring the suspension of step b/ at 50° C. for additional 1 hour; d/ cooling the suspension of step c/ to a temperature of 0-5° C.; e/ keeping the suspension of step d/ for 16 hours at a temperature of 0-5° C.; f/ isolating the intedanib p-toluenesulfonic acid salt in Crystal modification 2 and g/ optionally, drying the product of step f/ under the laboratory conditions until the constant weight of the product is reached.

The object of the invention is the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate L-tartaric acid acid salt of Formula I, wherein X represents L-tartrate, having an X-ray powder diffraction pattern comprising characteristic peaks at about 9.5; 14.0; 17.8; 19.5; 20.0 and 22.0±0.2° 2-theta measured by CuKα radiation. In some embodiments the Crystal modification 1 is characterised by differential scanning calorimetry curve having a melting process with $T_{desolvation}$=58.5° C. and $T_{peak}$=253.8° C. In some embodiments the Crystal modification 1 is characterised by the thermal gravimetric curve having a 1.69% weight loss in the range of 25° C. to 57° C.

It should be understood that relative intensity can vary depending on a number of factors, including sample preparation and mounting, the instrument and analytical procedure and settings used to obtain the spectrum.

Another object of the invention is a process for the preparation of the Crystal modification 1 of intedanib L-tartrate wherein intedanib free base is suspended in a polar aprotic solvent and L-tartaric acid is then added, preferably the polar aprotic solvent is methyl ethyl ketone at the temperature of 50° C., preferably followed by heating of the system to a temperature 50° C. followed by the addition of the counterion, kept at the temperature of 50° C. for additional 1 hour, then slowly cooled to the temperature of 0-5° C. The polar aprotic solvent is selected from the group consisting of methyl-acetate, ethyl-acetate, butyl-acetate, acetonitrile, acetone, methyl ethyl ketone or a mixture thereof, more preferably the suitable polar aprotic solvent is methyl ethyl ketone, even more preferably it is methyl ethyl ketone at the temperature of 50° C.

In some embodiments the process for the preparation of the Crystal modification 1 of intedanib L-tartrate comprises the following steps: a/ suspending intedanib free base in a polar aprotic solvent selected from the group consisting of: methyl-acetate, ethyl-acetate, butyl-acetate, acetonitrile, acetone, methyl ethyl ketone or a mixture thereof, more preferably in methyl ethyl ketone at the temperature of 50° C.; b/ drop-wise addition of the solution of the L-tartaric acid when dissolution and precipitation occurred; c/ stirring the suspension of step b/ at 50° C. for additional 1 hour; d/ cooling the suspension of step c/ to a temperature of 0-5° C.; e/ keeping the suspension of the step d/ for 16 hours at a temperature of 0-5° C.; f/ isolating the intedanib L-tartaric acid salt in Crystal modification 1 and g/ optionally, drying the product of step f/ under the laboratory conditions until the constant weight of the product is reached.

The object of the invention is the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate maleic acid salt of Formula I, wherein X represents maleate, having an X-ray powder diffraction pattern comprising characteristic peaks at about 12.6; 16.4; 19.5; 21.4 and 25.0±0.2° 2-theta measured by CuKα radiation. In some embodiments the Crystal modification 1 is characterised by differential scanning calorimetry curve having a melting process with $T_{desolvation}$=216.5° C. and $T_{peak}$=232.5° C. In some embodiments the Crystal modification 2 is characterised by the thermal gravimetric curve having a 1.17% weight loss in the range of 25° C. to 190° C. and 1% weight loss in the range of 190° C. to 221° C.

It should be understood that relative intensity can vary depending on a number of factors, including sample preparation and mounting, the instrument and analytical procedure and settings used to obtain the spectrum.

Another object of the invention is a process for the preparation of the Crystal modification 1 of intedanib maleate wherein intedanib free base is suspended in a polar aprotic solvent and maleic acid is then added, preferably the polar aprotic solvent is at the temperature of 50° C., preferably followed by heating of the system to a temperature 50° C. followed by the addition of the counterion, kept at the temperature of 50° C. for additional 1 hour, then slowly cooled to the temperature of 0-5° C. The polar aprotic solvent is selected from the group consisting of methyl-acetate, ethyl-acetate, butyl-acetate, acetonitrile, acetone, methyl ethyl ketone or a mixture thereof, more preferably the suitable polar aprotic solvent is ethyl-acetate, even more preferably it is ethyl-acetate at the temperature of 50° C.

In some embodiments the process for the preparation of the Crystal modification 1 of intedanib maleate comprises the following steps: a/ suspending intedanib free base in a polar aprotic solvent selected from the group consisting of: methyl-acetate, ethyl-acetate, butyl-acetate, acetonitrile, acetone, methyl ethyl ketone or a mixture thereof, more preferably in ethyl-acetate at the temperature of 50° C.; b/ drop-wise addition of the solution of the L-tartaric acid when dissolution and precipitation occurred; c/ stirring the suspension of step b/ at 50° C. for additional 1 hour; d/ cooling the suspension of step c/ to a temperature of 0-5° C.; e/ keeping the suspension of step d/ for 16 hours at a temperature of 0-5° C.; f/ isolating the intedanib maleic acid salt in Crystal modification 1 and g/optionally, drying the product of step f/ under the laboratory conditions until the constant weight of the product is reached.

The object of the invention is the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate acetic acid salt of Formula I, wherein X represents acetate, having an X-ray powder diffraction pattern comprising characteristic peaks at about 6.6; 9.4; 15.3; 19.0; 20.7 and 21.8±0.2° 2-theta measured by CuKα radiation. In some embodiments the Crystal modification 1 is characterised by differential scanning calorimetry curve having a melting process with $T_{desolvation1}$=120.7° C., $T_{desolvation2}$=146.6° C., $T_{peak1}$=177.5° C. and $T_{peak2}$=254.4° C. In some embodiments the Crystal modification 1 is characterised by the thermal gravimetric curve having a 0.27% weight loss in the range of 25° C. to 100° C., 5.6% weight loss in the range of 100° C. to 155° C., 3.2% weight loss in the range of 155° C. to 182° C. and 3.7% weight loss in the range of 182° C. to 248° C.

It should be understood that relative intensity can vary depending on a number of factors, including sample preparation and mounting, the instrument and analytical procedure and settings used to obtain the spectrum.

Another object of the invention is a process for the preparation of the Crystal modification 1 of intedanib acetate wherein intedanib free base is suspended in a polar aprotic solvent and acetic acid is then added, preferably the polar aprotic solvent is methyl ethyl ketone at the temperature of 50° C., preferably followed by heating of the system to a temperature 50° C. followed by the addition of the counterion, kept at the temperature of 50° C. for additional 1 hour, then slowly cooled to the temperature of 0-5° C. The polar aprotic solvent is selected from the group consisting of methyl-acetate, ethyl-acetate, butyl-acetate, acetonitrile, acetone, methyl ethyl ketone or a mixture thereof, more preferably the suitable polar aprotic solvent is methyl ethyl ketone, even more preferably it is methyl ethyl ketone at the temperature of 50° C.

In some embodiments the process for the preparation of the Crystal modification 1 of intedanib acetate comprises the following steps: a/ suspending intedanib free base in a polar aprotic solvent selected from the group consisting of: methyl-acetate, ethyl-acetate, butyl-acetate, acetonitrile, acetone, methyl ethyl ketone or a mixture thereof, more preferably in methyl ethyl ketone at the temperature of 50° C.; b/ drop-wise addition of the solution of the acetic acid when dissolution and precipitation occurred; c/ stirring the suspension of step b/ at 50° C. for additional 1 hour; d/ cooling the suspension of step c/ to a temperature of 0-5° C.; e/ keeping the suspension of step d/ for 16 hours at a temperature of 0-5° C.; f/ isolating the intedanib acetic acid salt in Crystal modification 1 and g/optionally, drying the product of step f/ under the laboratory conditions until the constant weight of the product is reached.

The object of the invention is the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate phosphoric acid salt of Formula I, wherein X represents phosphate, having an X-ray powder diffraction pattern comprising characteristic peaks at about 5.5; 8.1; 11.2; 16.2; 19.5 and 22.3±0.2° 2-theta measured by CuKα radiation. In some embodiments the Crystal modification 1 is characterised by differential scanning calorimetry curve having a melting process with $T_{desolvation}$=140.1° C., $T_{peak}$=247.6° C. and $T_{peak2}$=283.0° C. In some embodiments the Crystal modification 1 is characterised by the thermal gravimetric curve having a 2.85% weight loss in the range of 25° C. to 110° C.

It should be understood that relative intensity can vary depending on a number of factors, including sample preparation and mounting, the instrument and analytical procedure and settings used to obtain the spectrum.

Another object of the invention is a process for the preparation of the Crystal modification 1 of intedanib phosphate wherein intedanib free base is suspended in a polar aprotic solvent and phosphoric acid is then added, preferably the polar aprotic solvent is at the temperature of 50° C., preferably followed by heating of the system to a temperature 50° C. followed by the addition of the counterion, kept at the temperature of 50° C. for additional 1 hour, then slowly cooled to the temperature of 0-5° C. The polar aprotic solvent is selected from the group consisting of methyl-acetate, ethyl-acetate, butyl-acetate, acetonitrile, acetone, methyl ethyl ketone or a mixture thereof, more preferably the suitable polar aprotic solvent is ethyl-acetate, even more preferably it is ethyl-acetate at the temperature of 50° C.

In some embodiments the process for the preparation of the Crystal modification 1 of intedanib phosphate comprises the following steps: a/ suspending intedanib free base in a polar aprotic solvent selected from the group consisting of: methyl-acetate, ethyl-acetate, butyl-acetate, acetonitrile, acetone, methyl ethyl ketone or a mixture thereof, more preferably in ethyl-acetate at the temperature of 50° C.; b/ drop-wise addition of the solution of the phosphoric acid (85%) when dissolution and precipitation occurred; c/ stirring the suspension of the step b/ at 50° C. for additional 1 hour; d/ cooling the suspension of step c/ to a temperature of 0-5° C.; e/ keeping the suspension of step d/ for 16 hours at a temperature of 0-5° C.; f/ isolating the intedanib phosphoric acid salt in Crystal modification 1 and g/ optionally, drying the product of step f/ under the laboratory conditions until the constant weight of the product is reached.

Another object of the present invention is a pharmaceutical composition comprising the crystal modification of intedanib mesylate, tosylate, L-tartrate, maleate, acetate, or phosphate and one or more pharmaceutically acceptable carriers or excipients.

BRIEF DESCRIPTION OF THE DRAWINGS

The figures depict the following spectrum, patterns and curves the various solid phases prepared according to the present invention.

Figure 21:
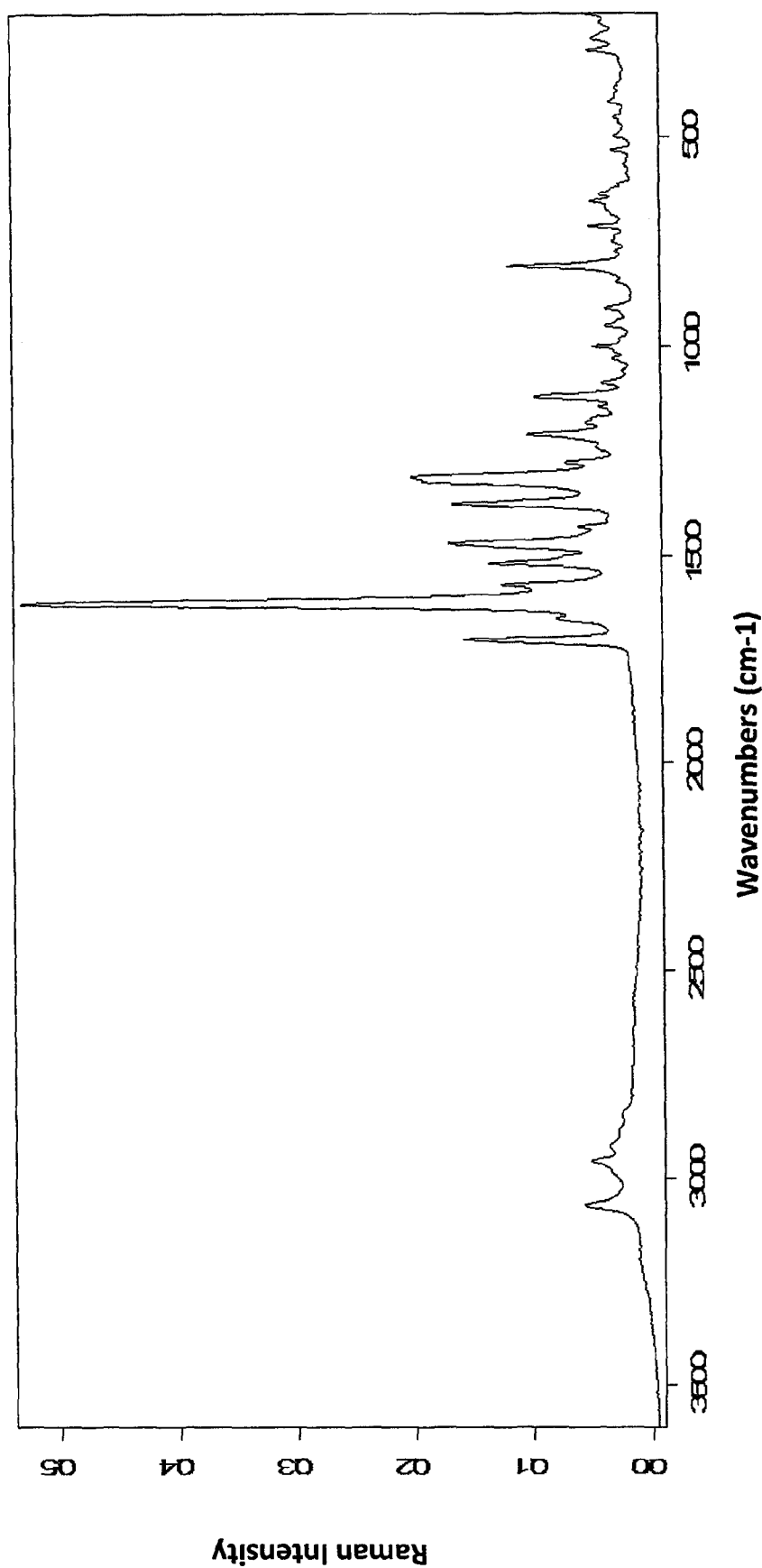
Figure 22:
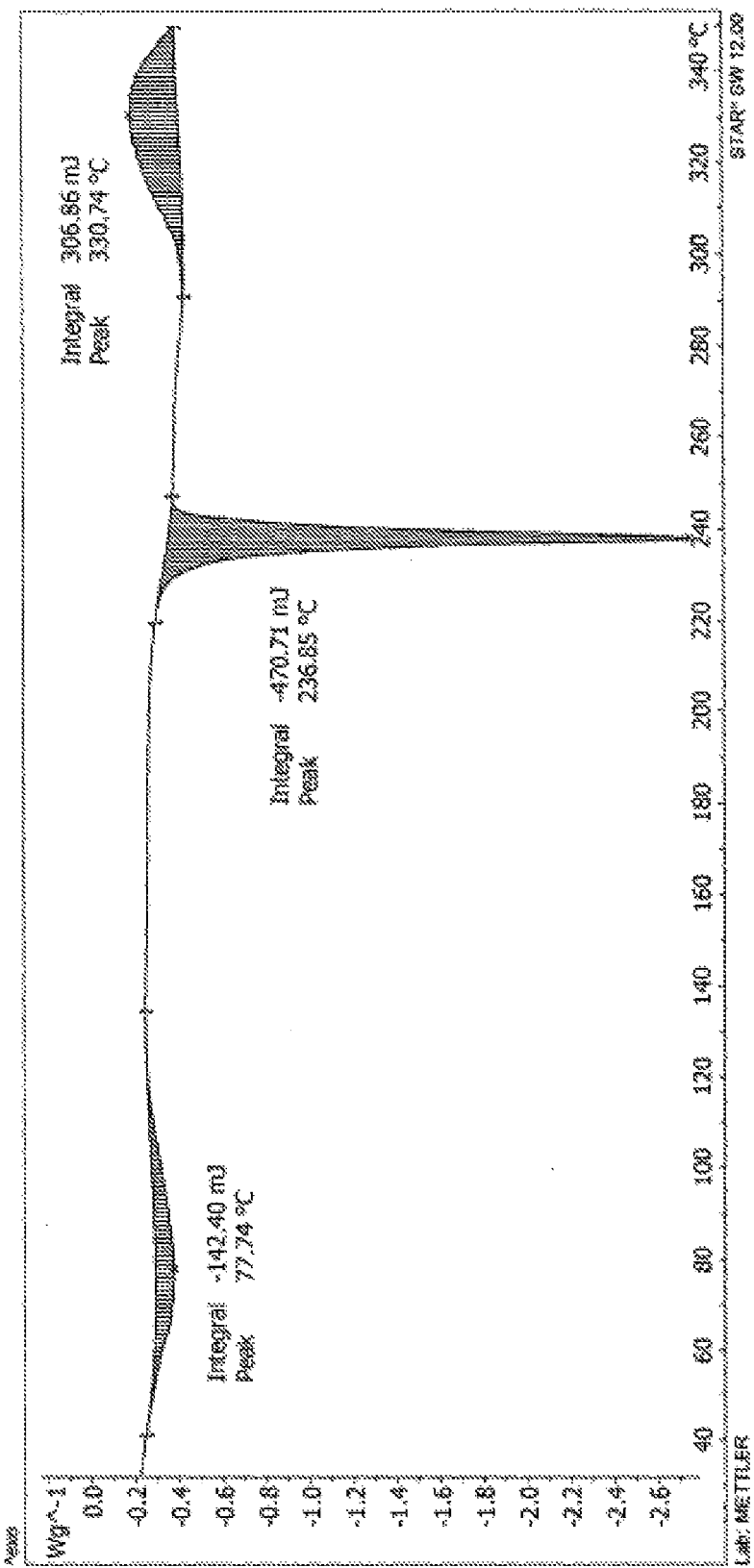
Figure 23:
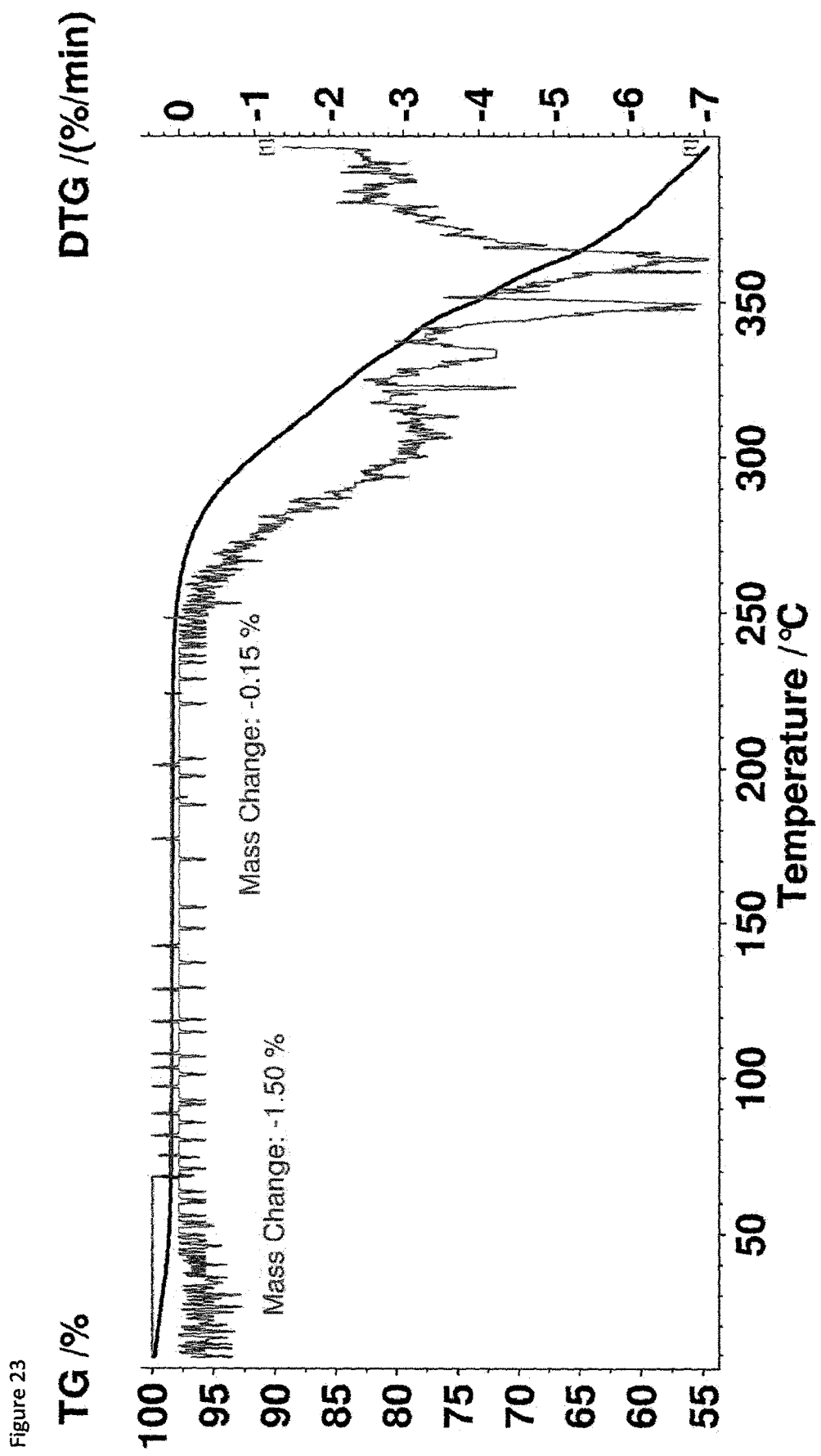
Figure 24:
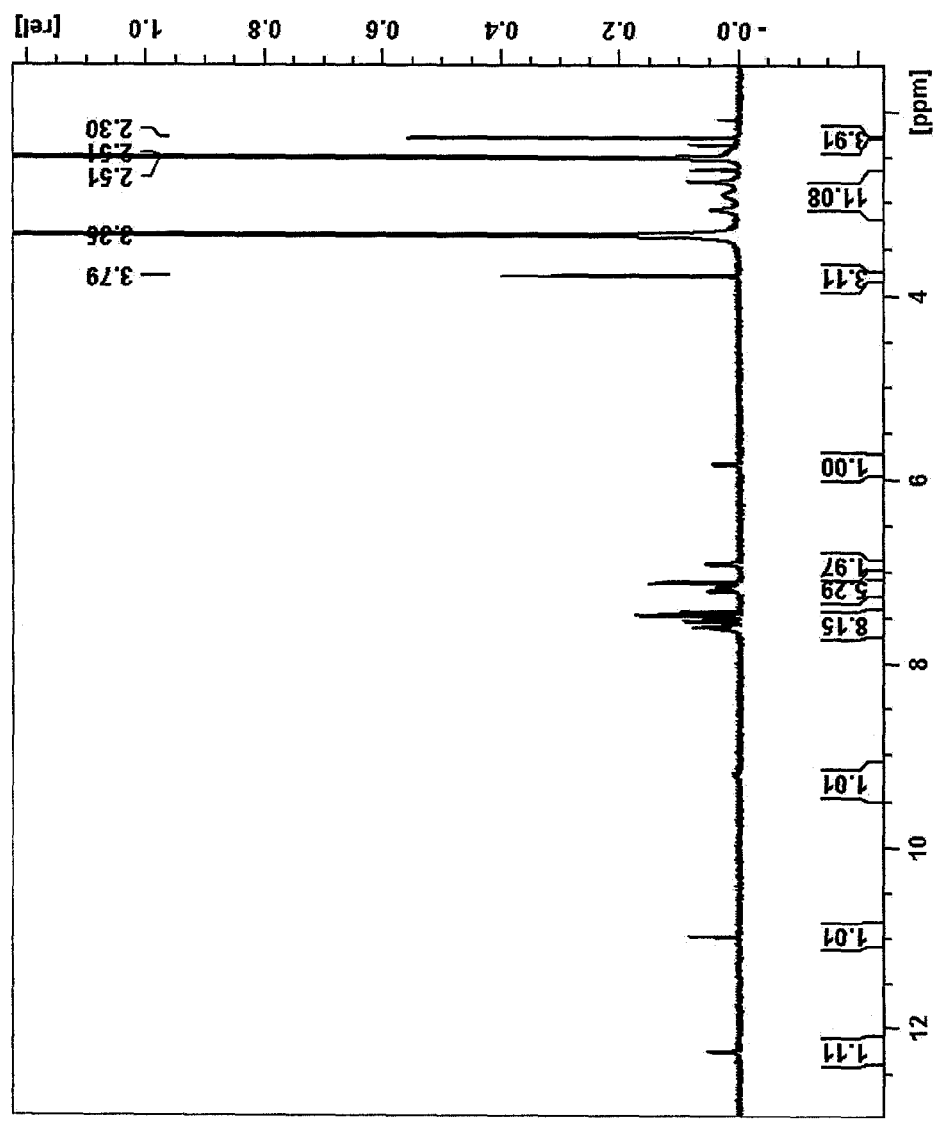
Figure 25:
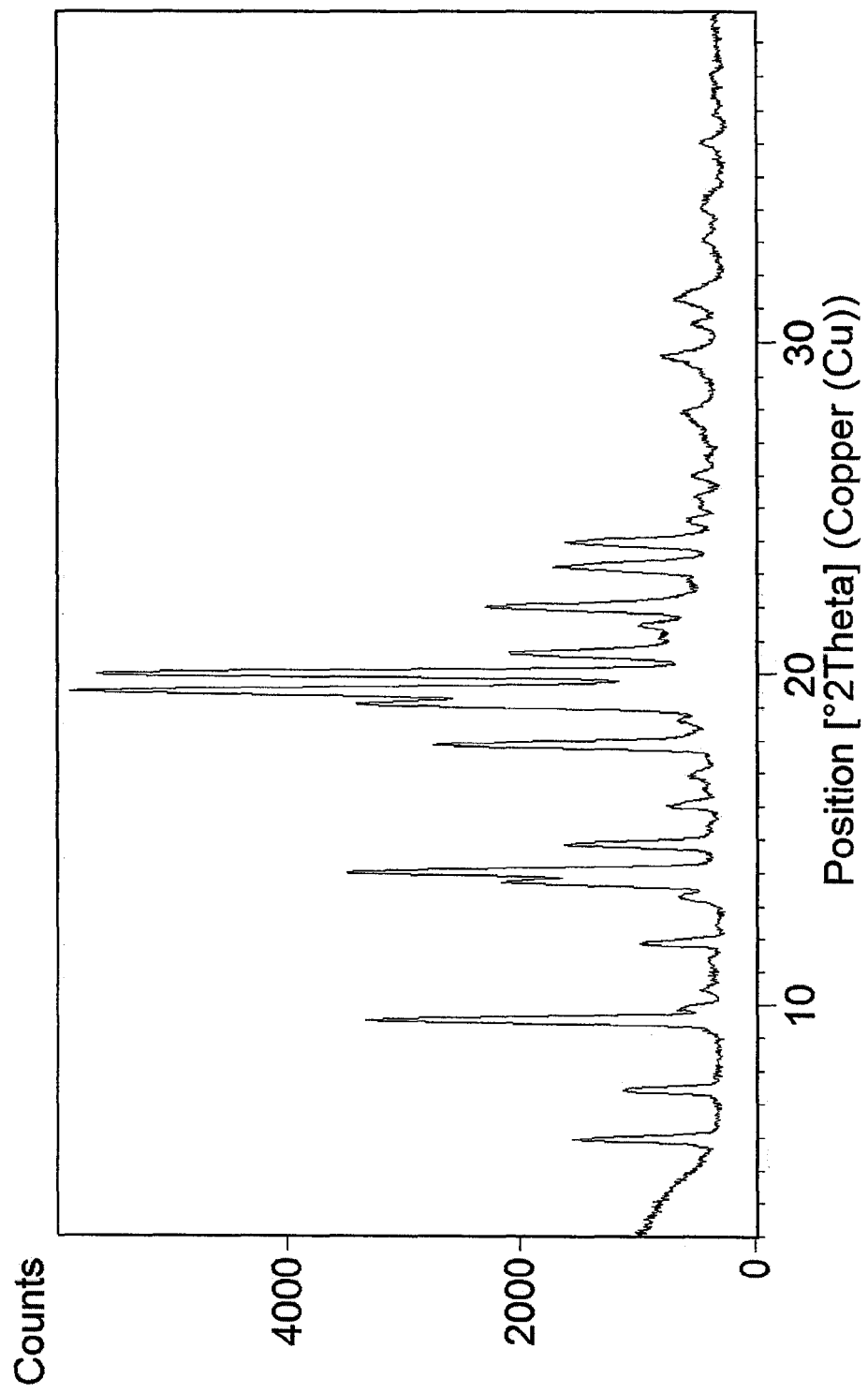
Figure 26:
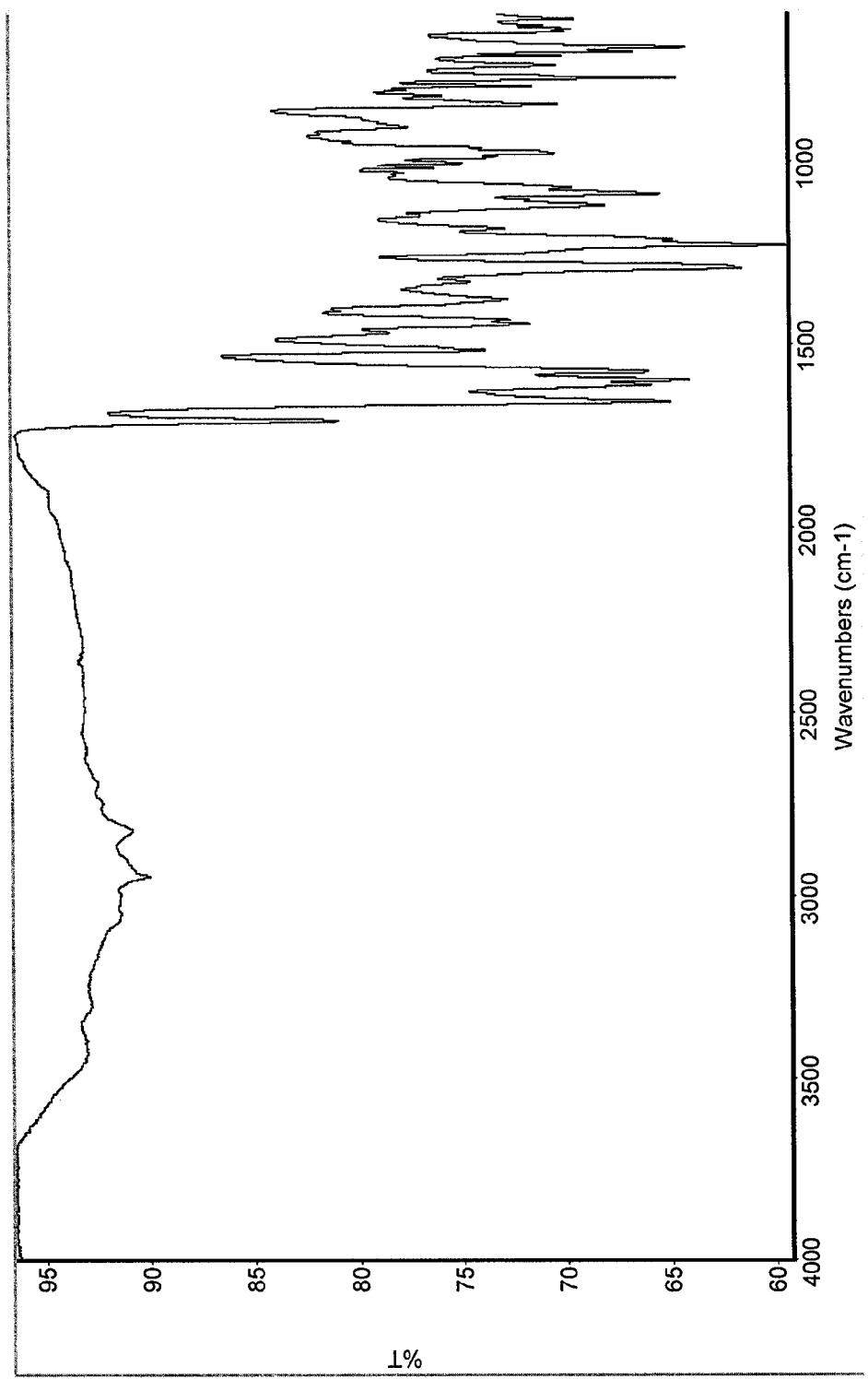
Figure 27:
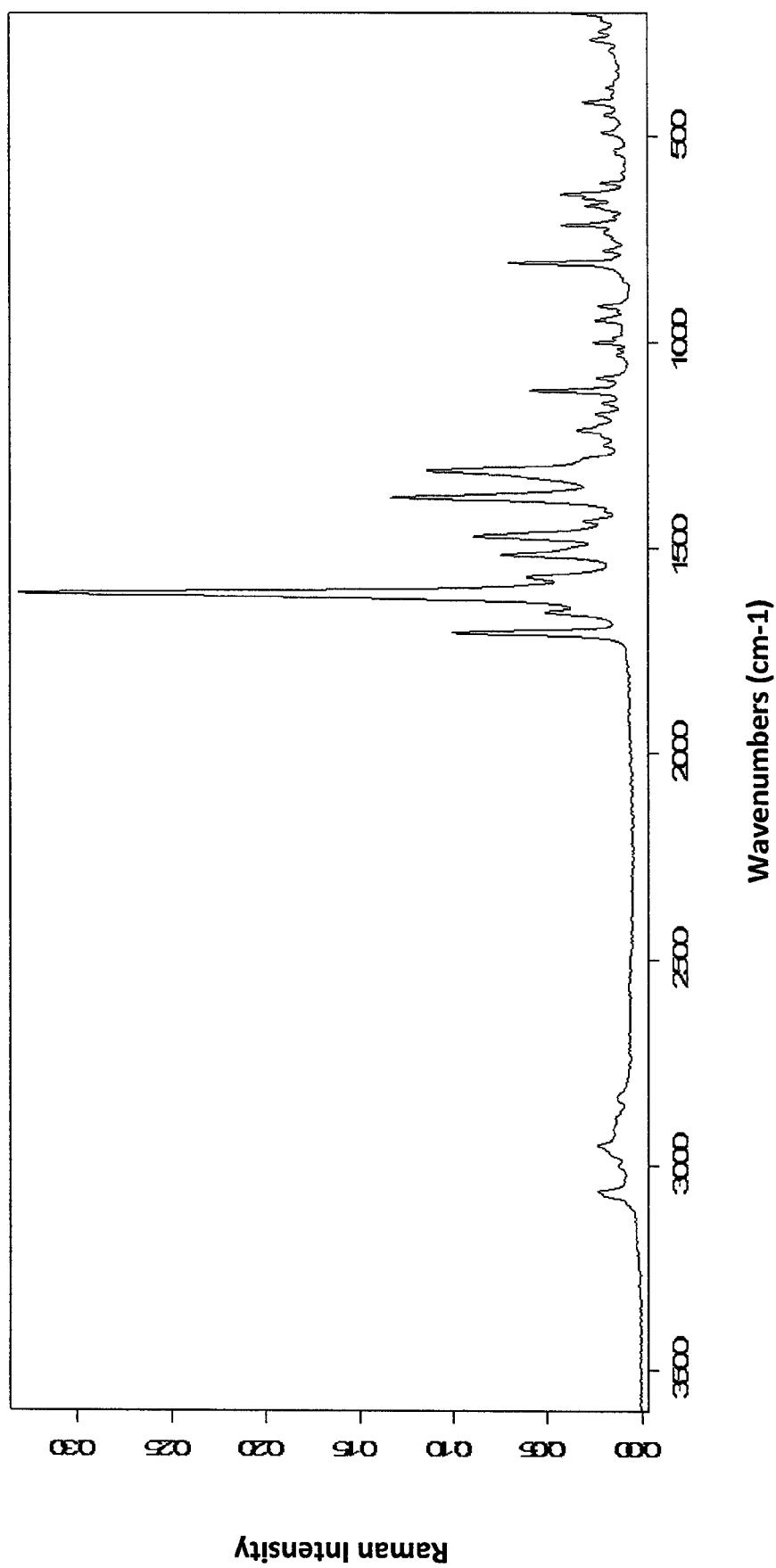
Figure 28:
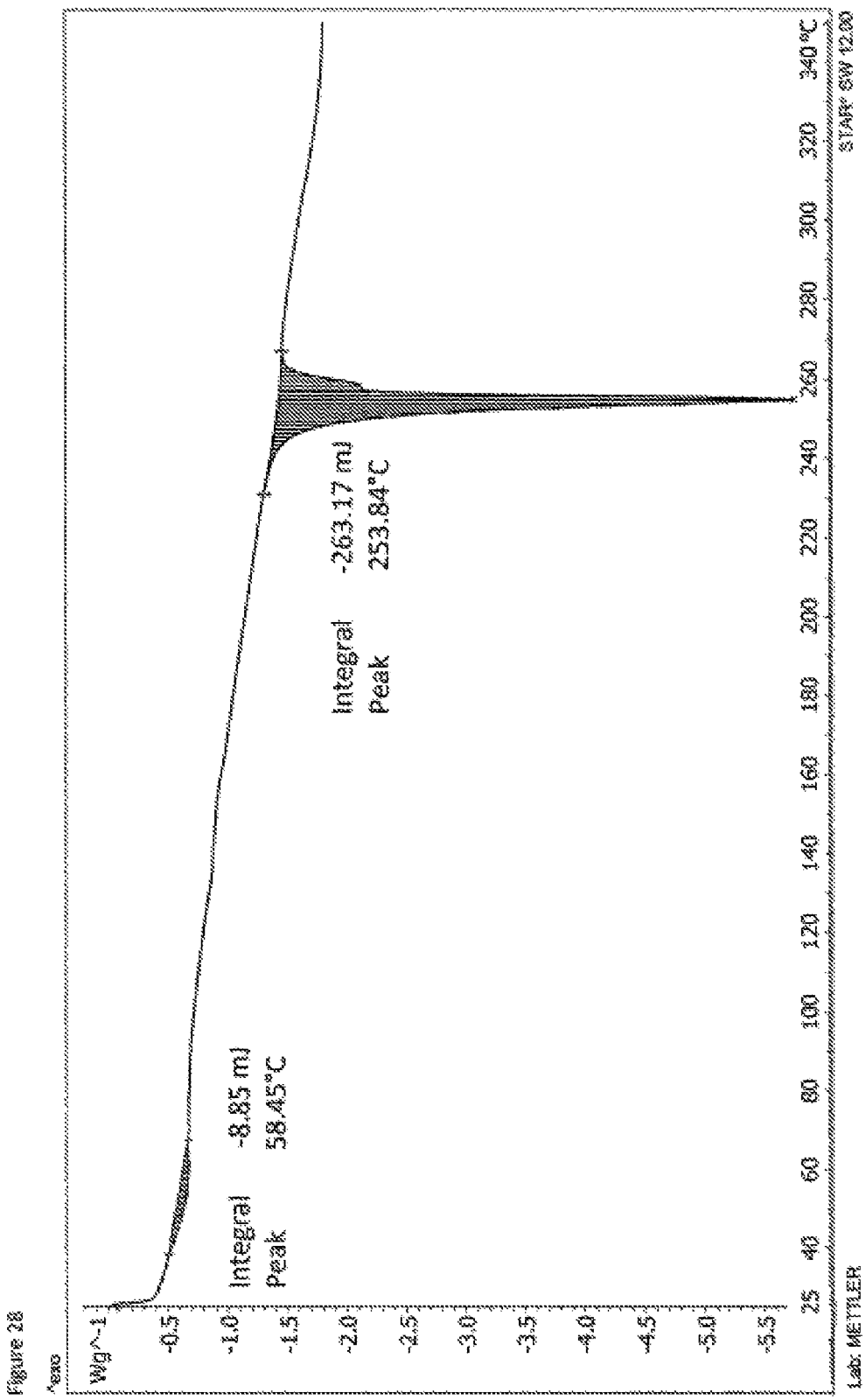
Figure 29:
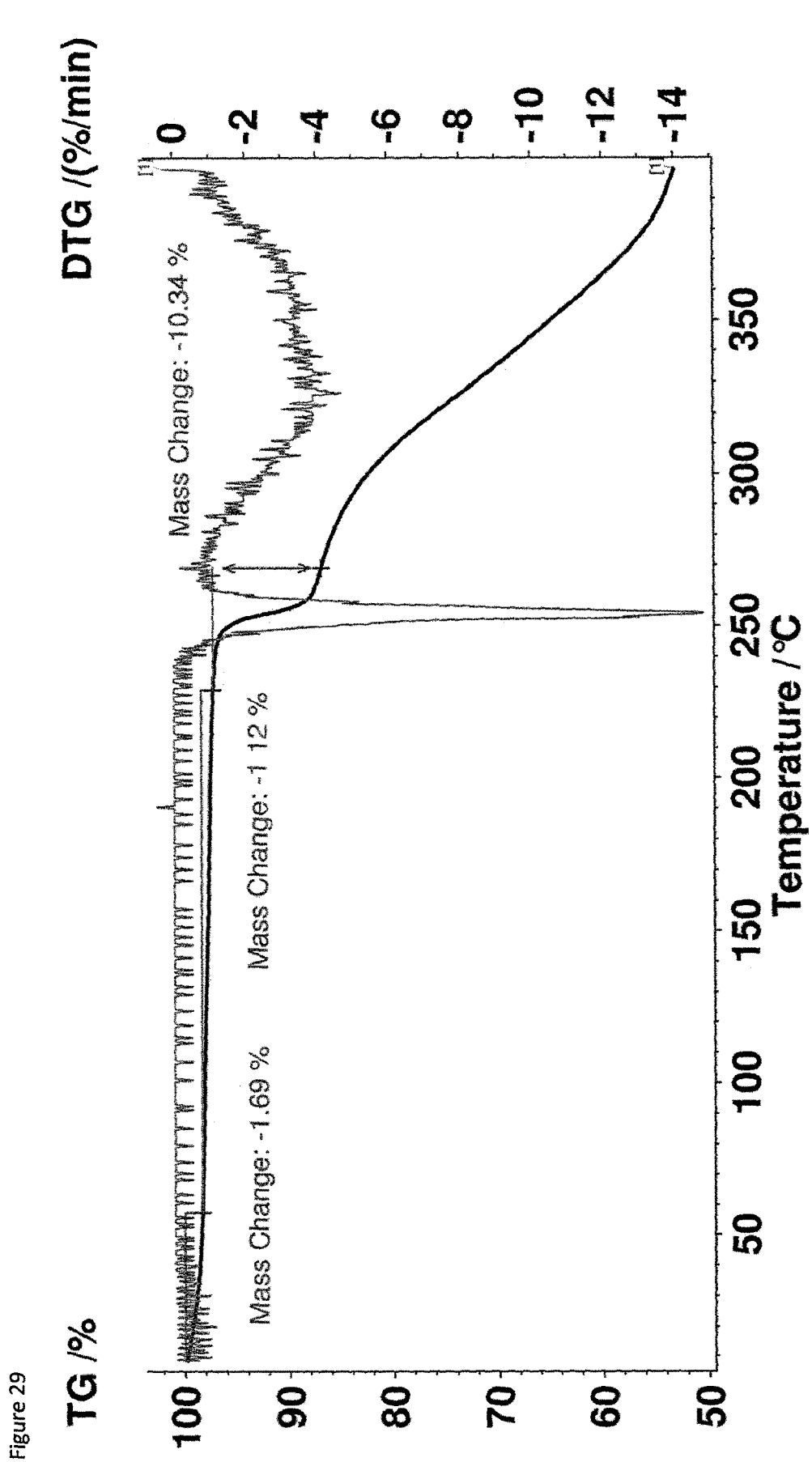
Figure 30:
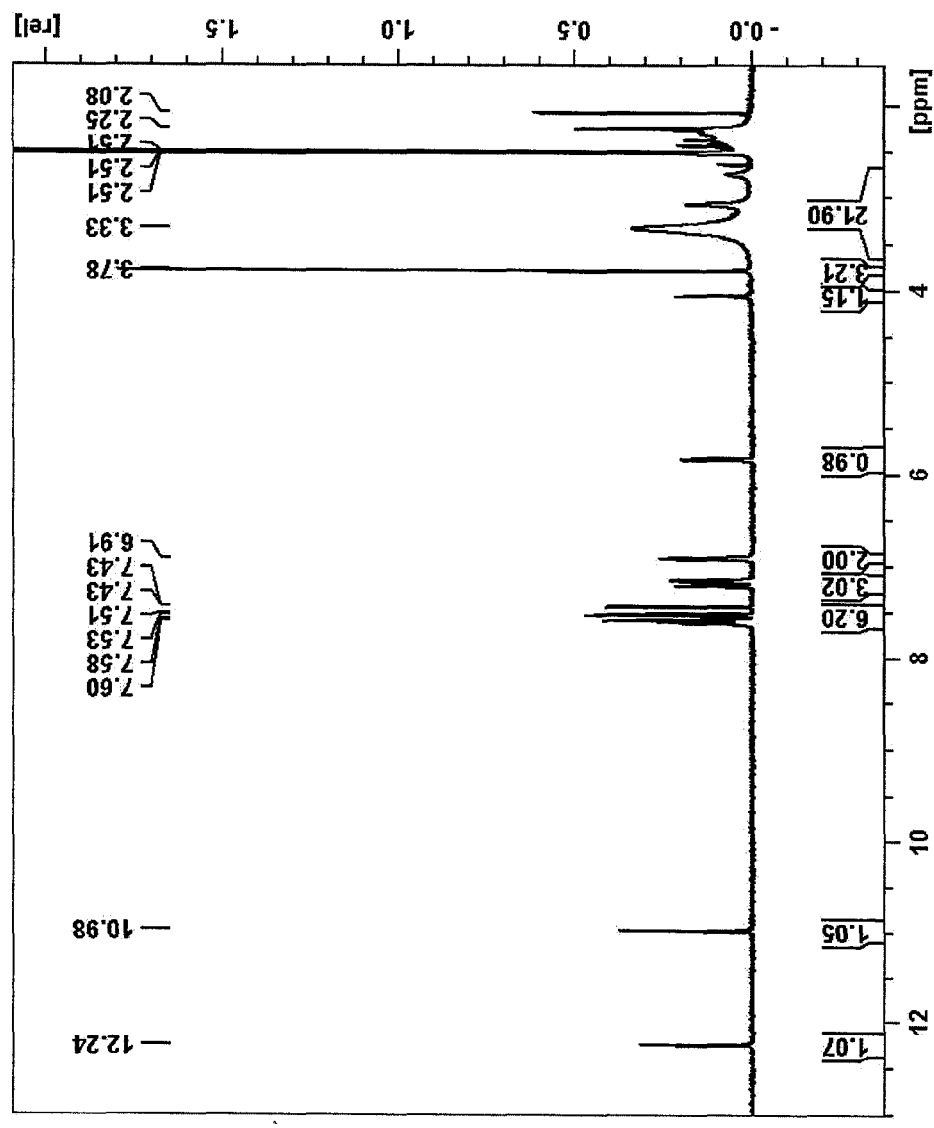
Figure 31:
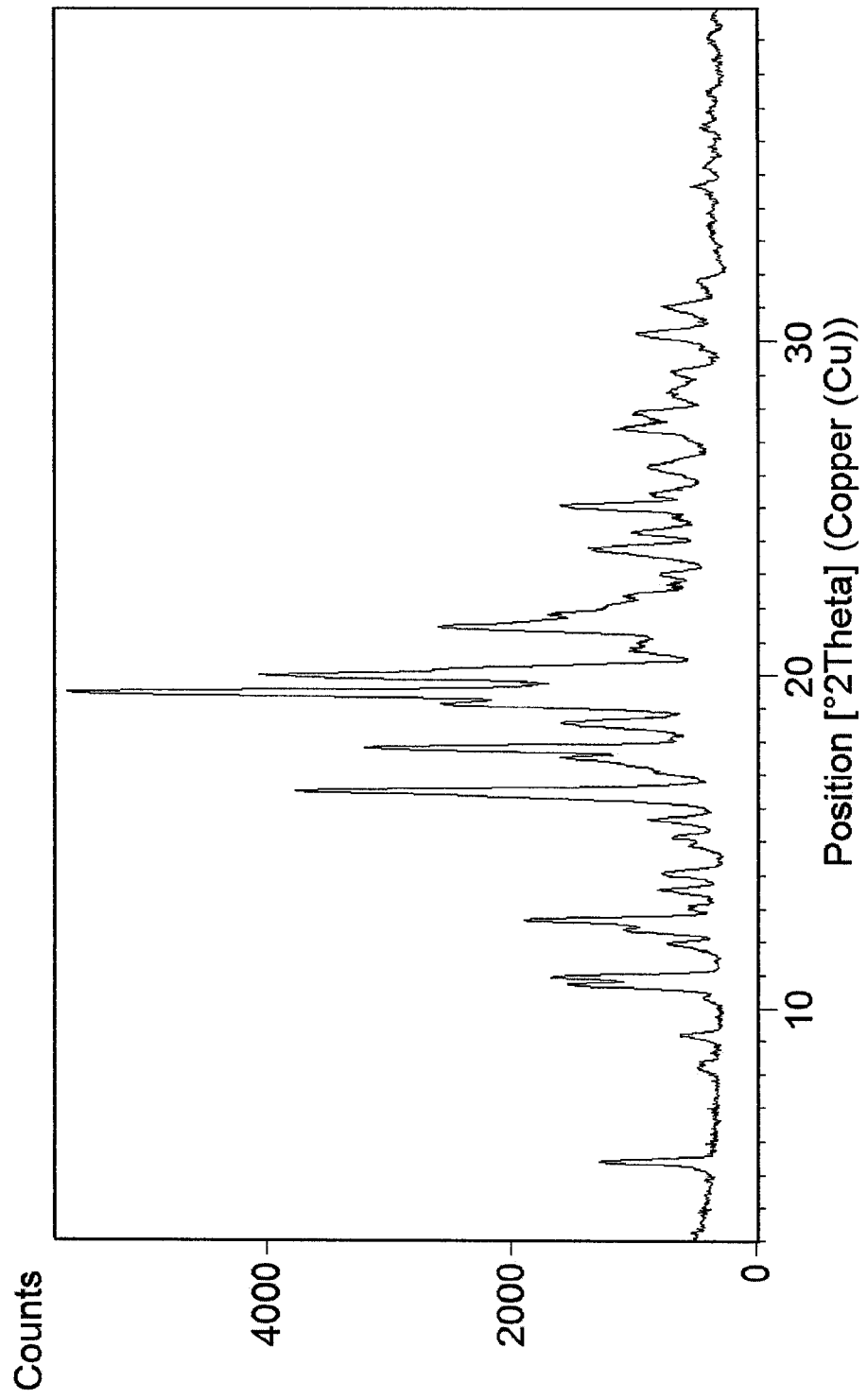
Figure 32:
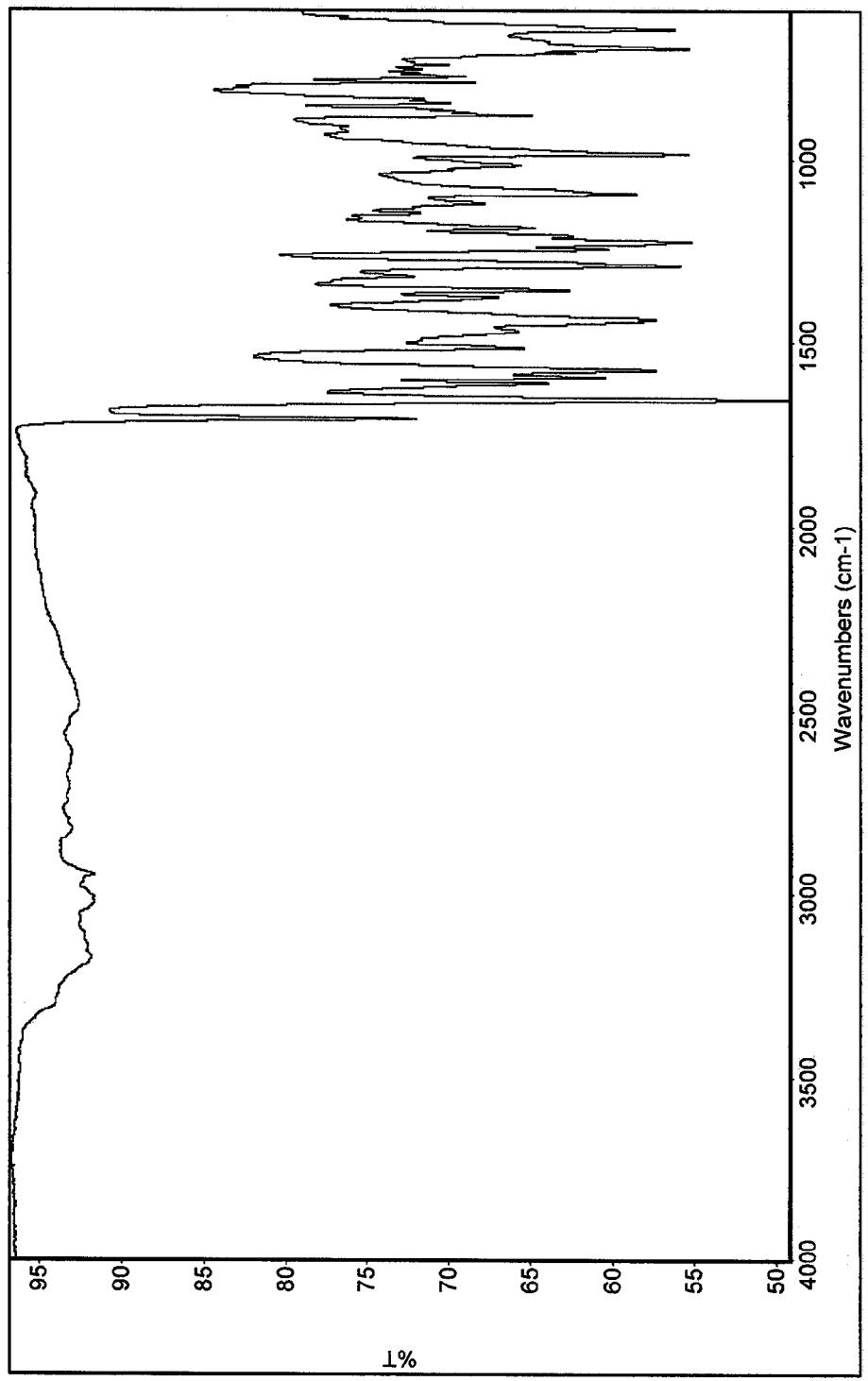
Figure 33:
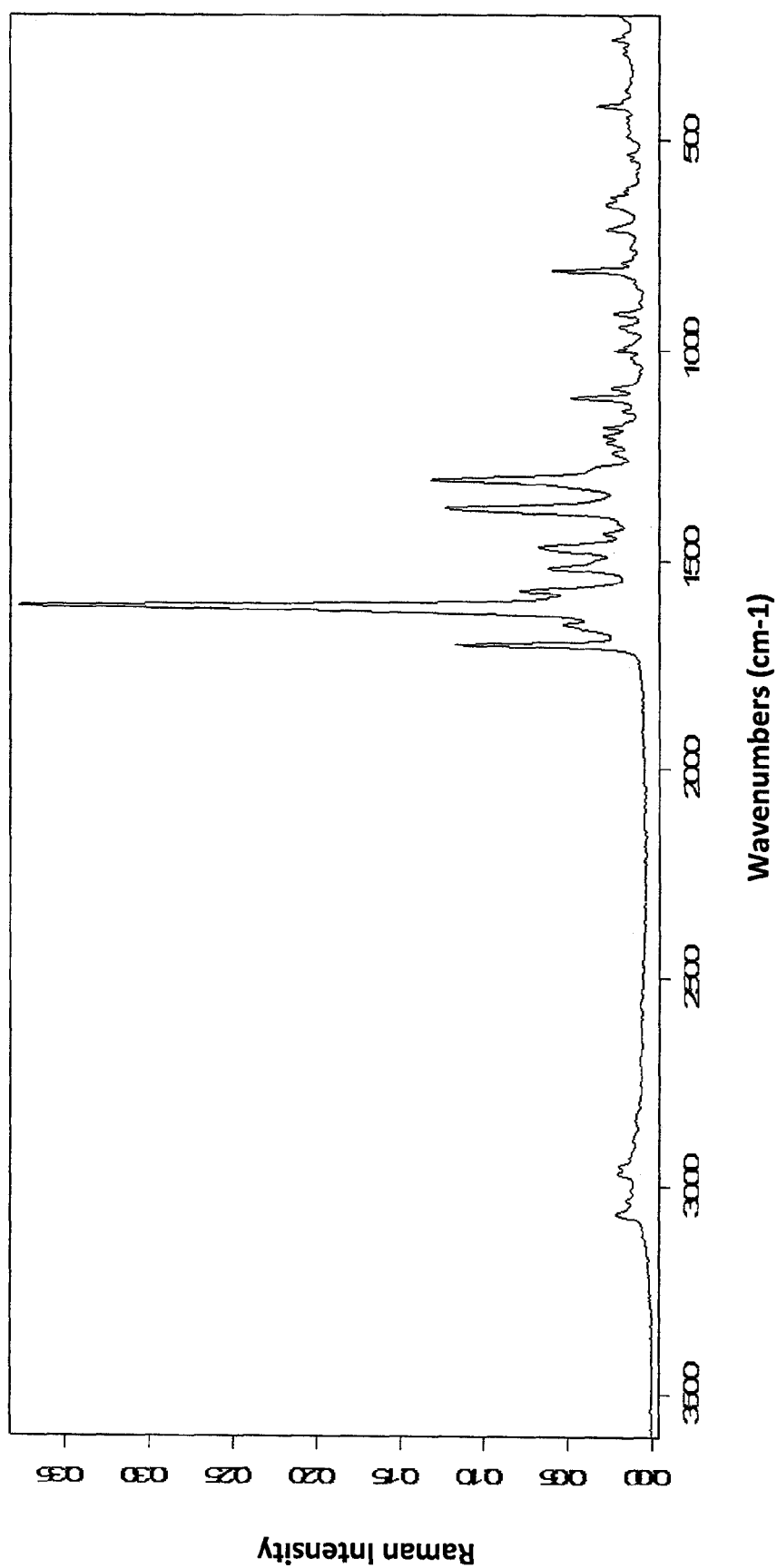
Figure 34:
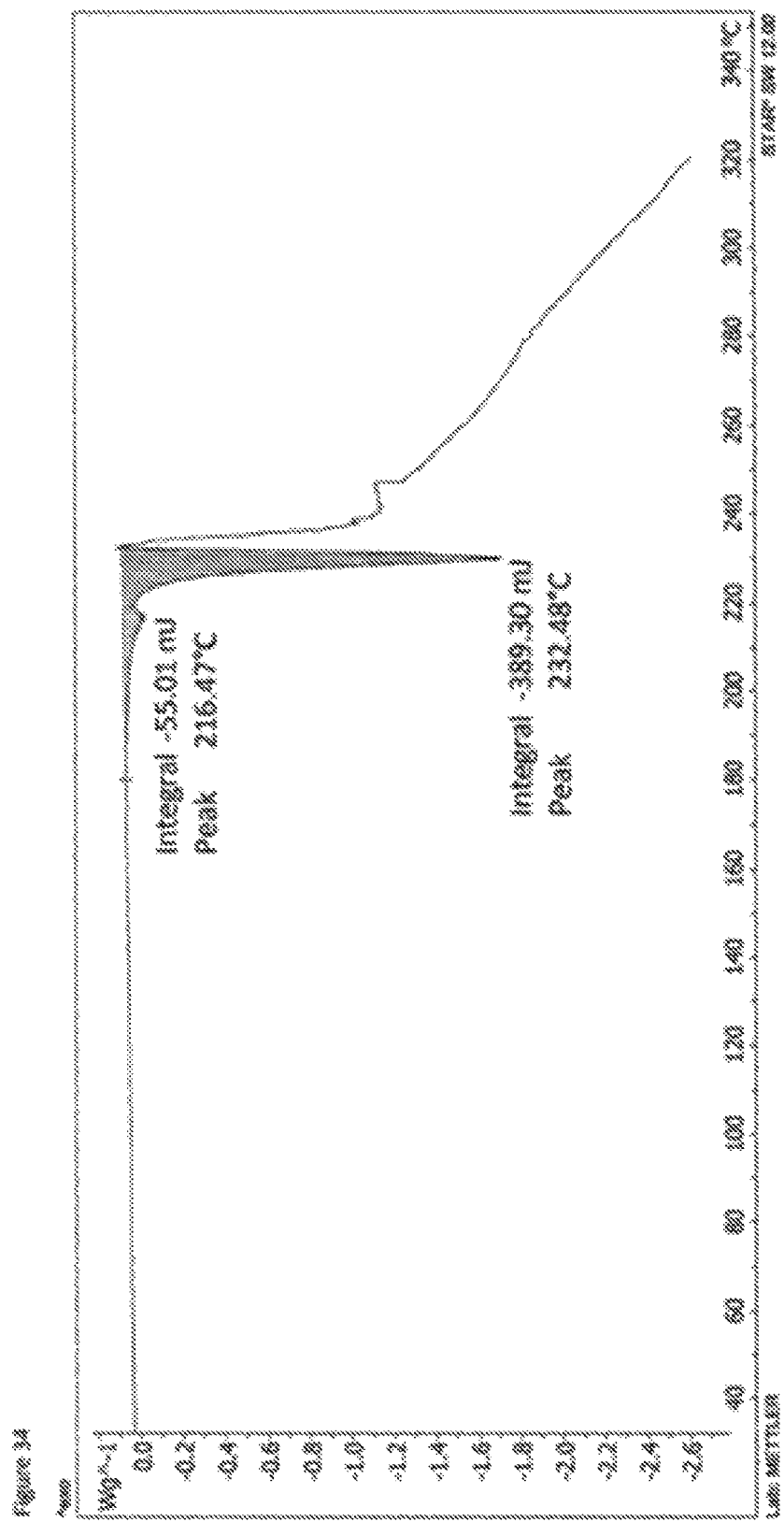
Figure 35:
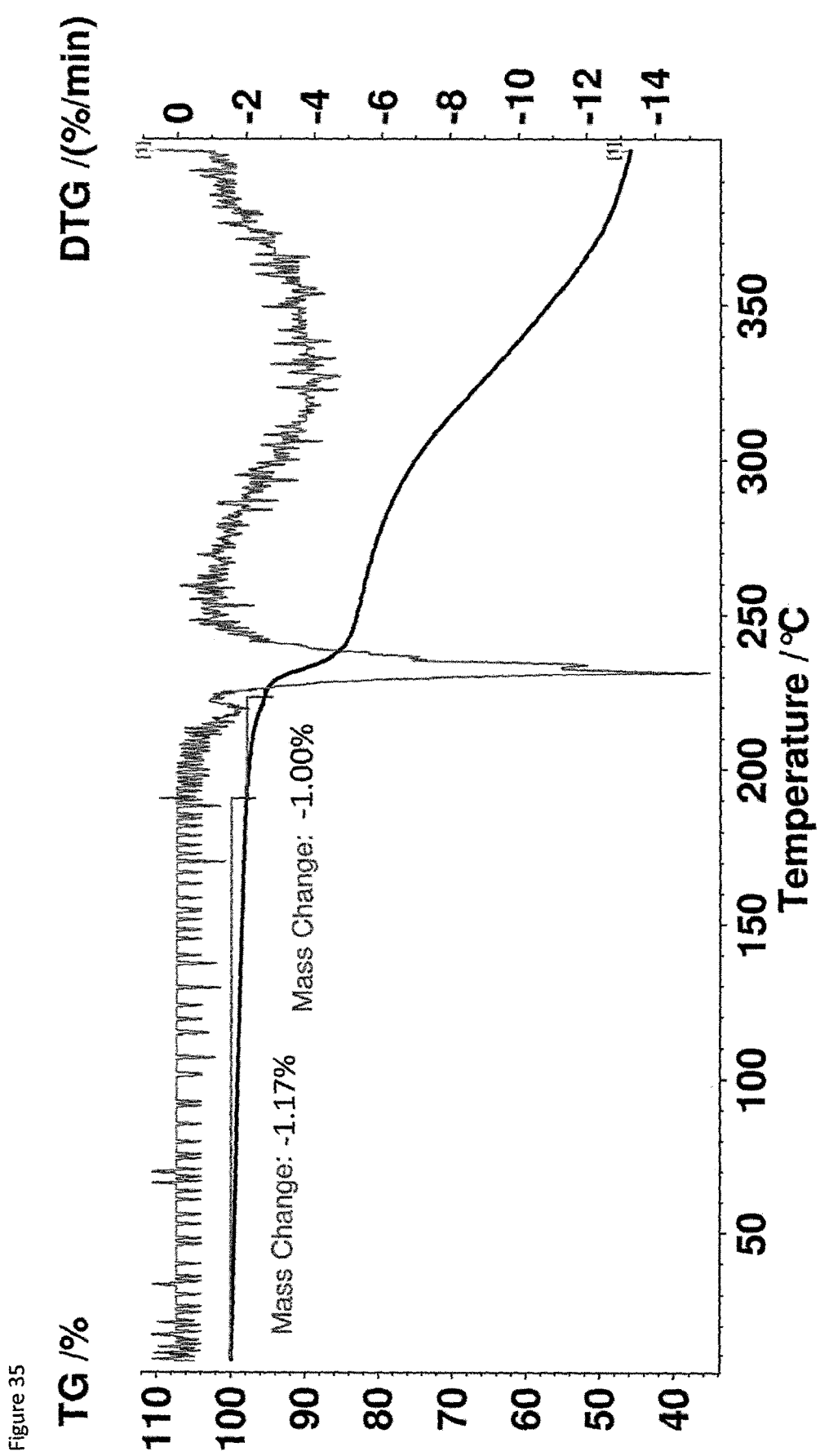
Figure 36:
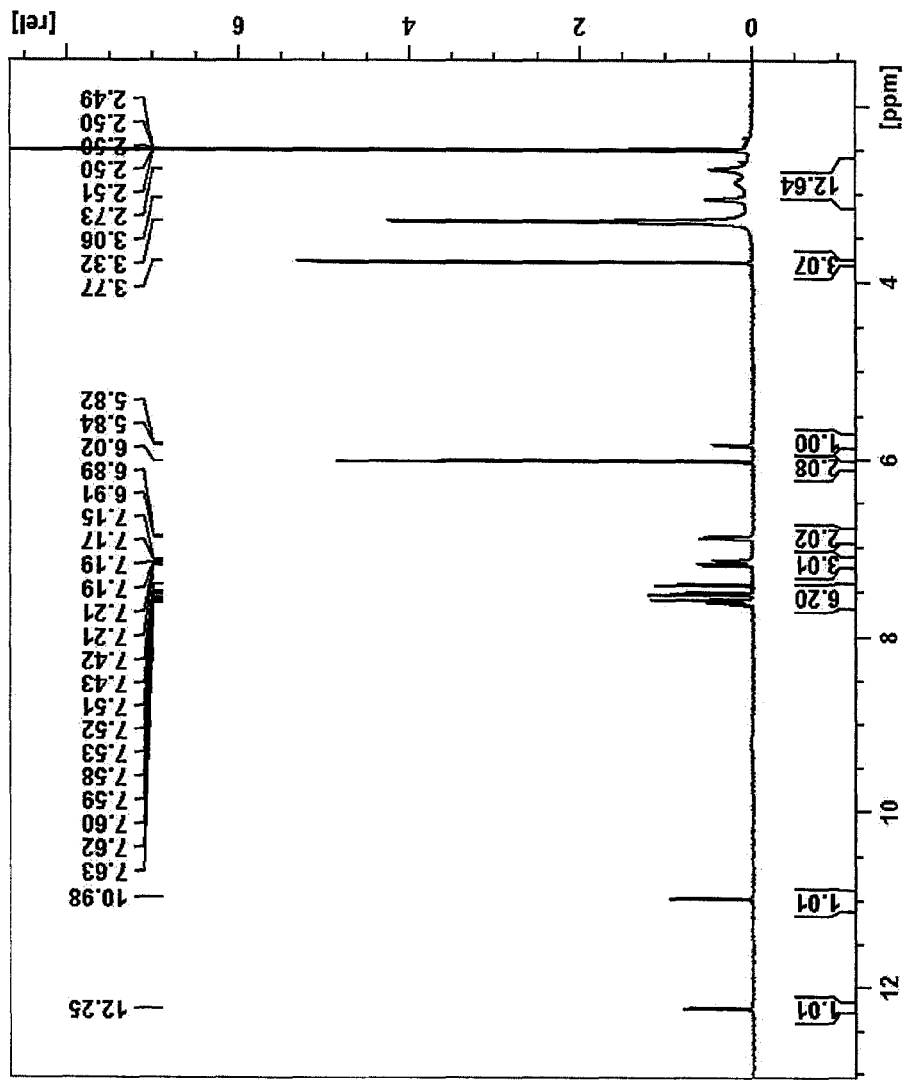
Figure 37:
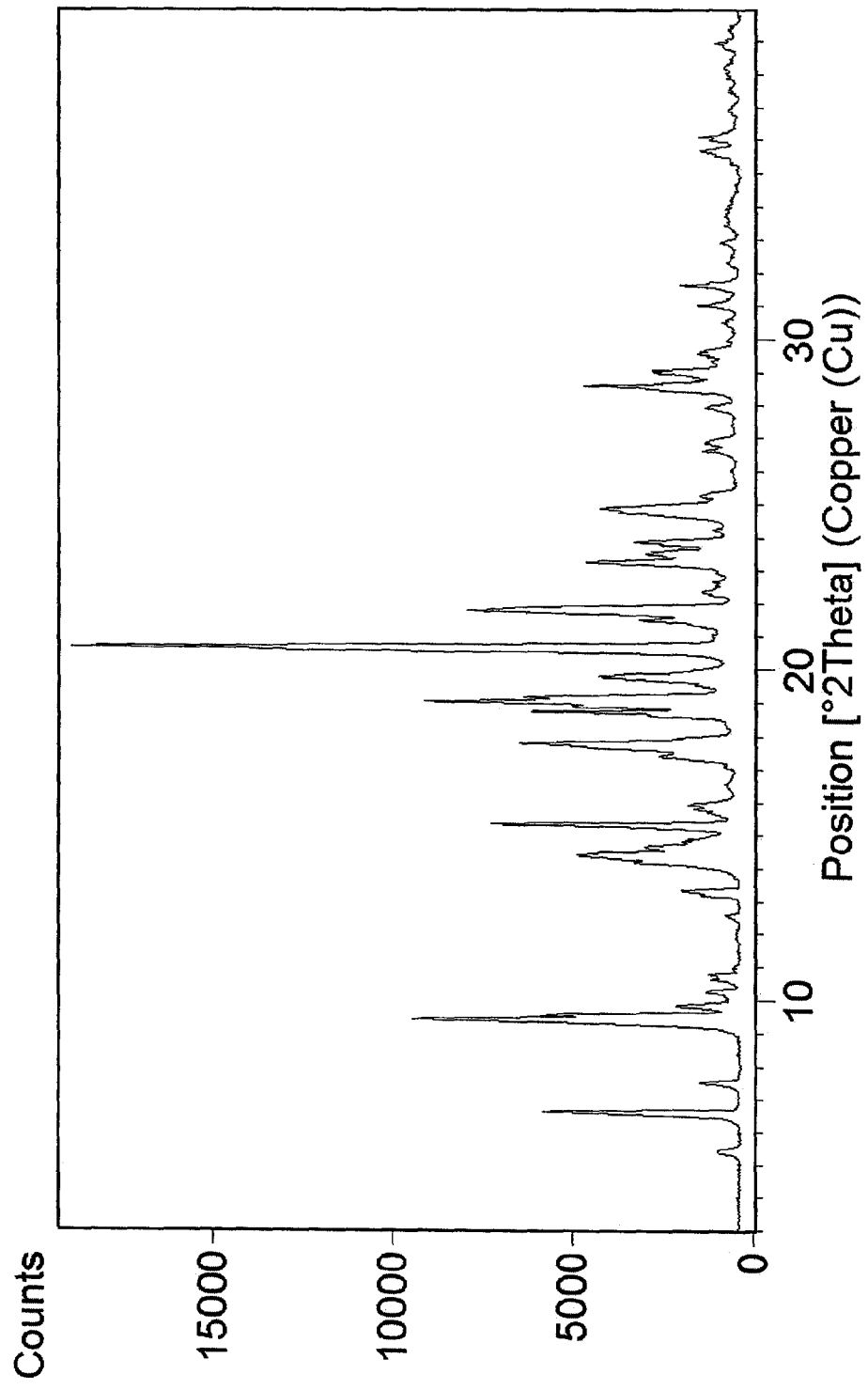
Figure 38:
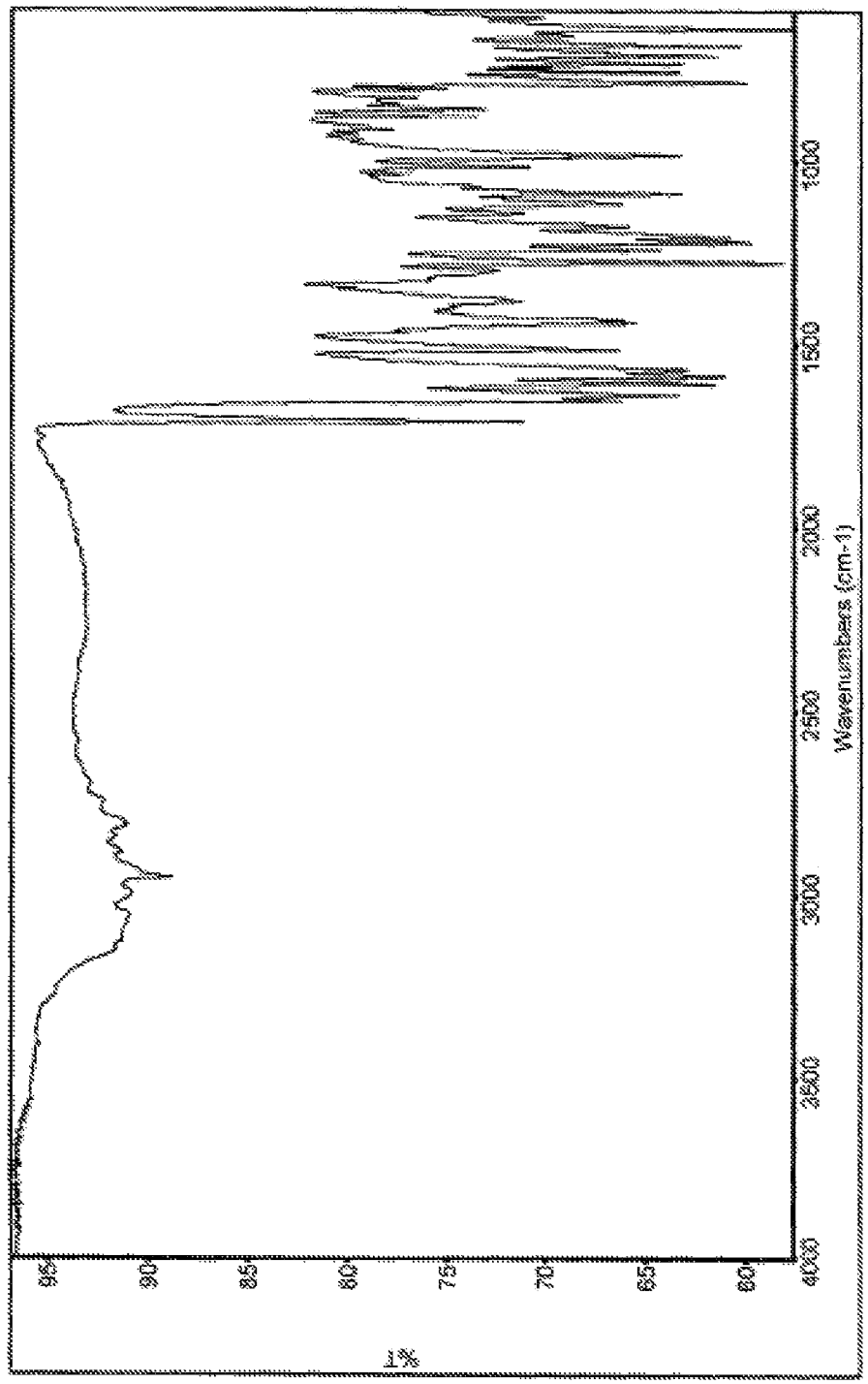
Figure 39:
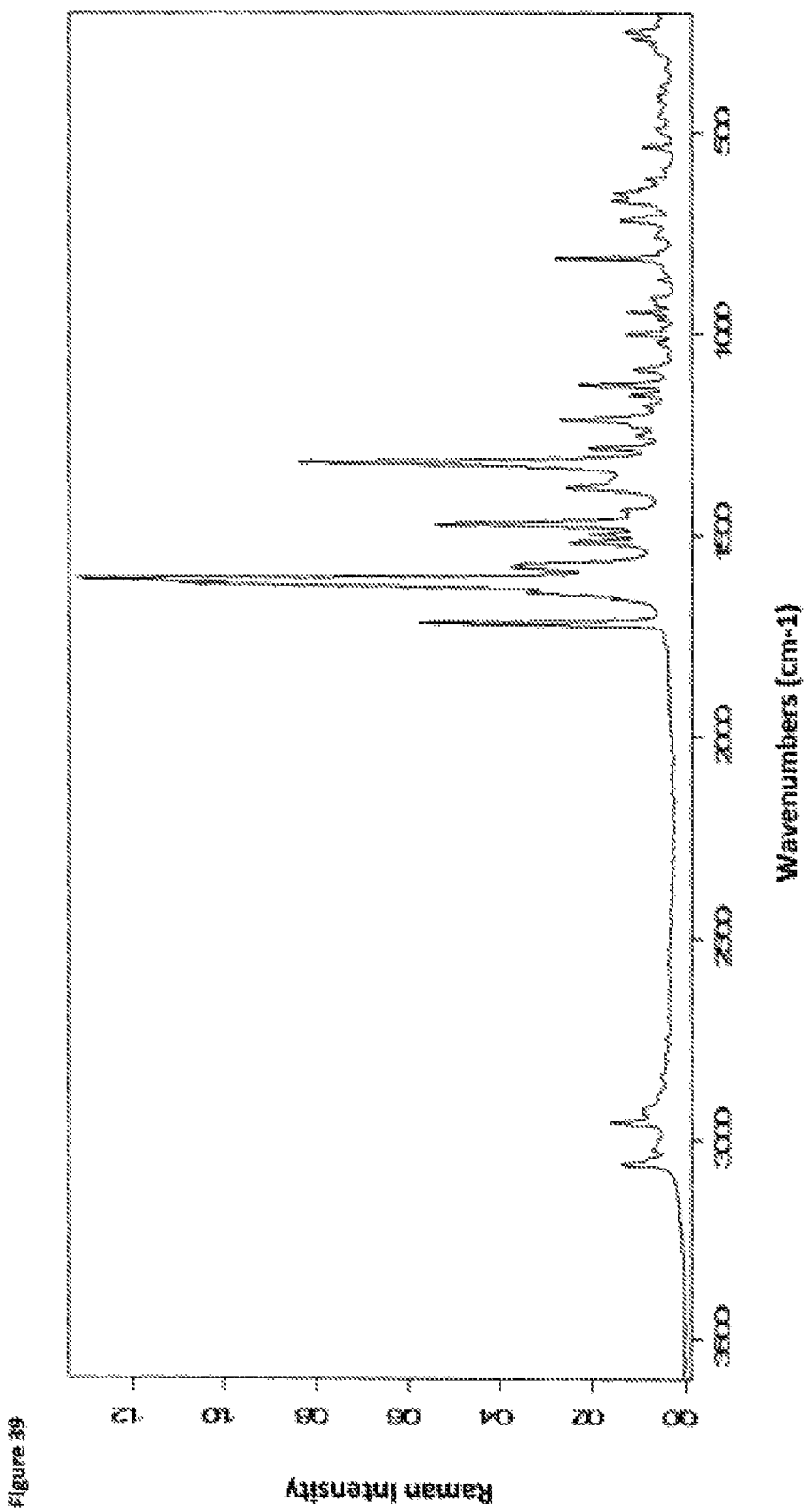
Figure 40:
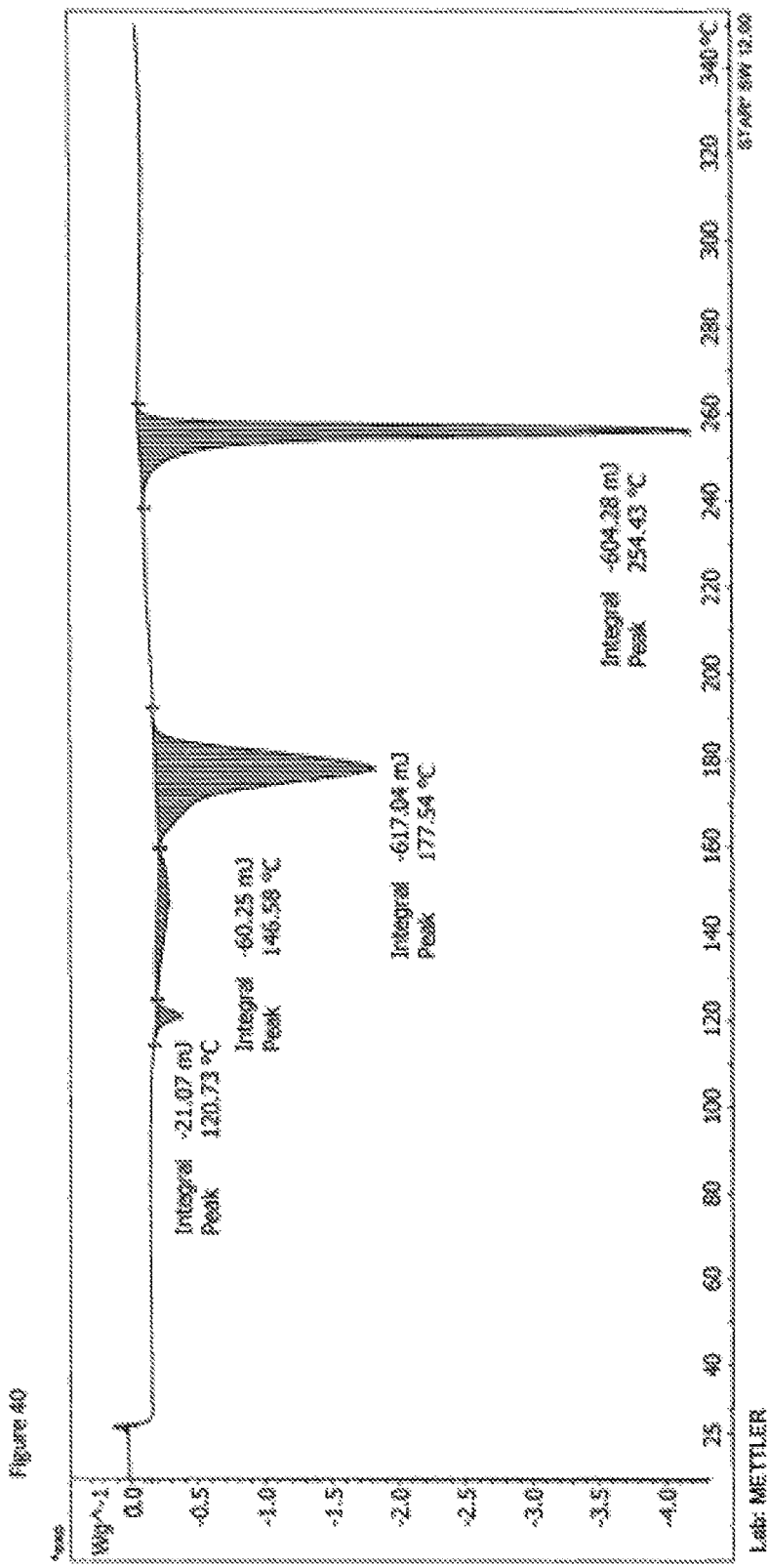
Figure 41:
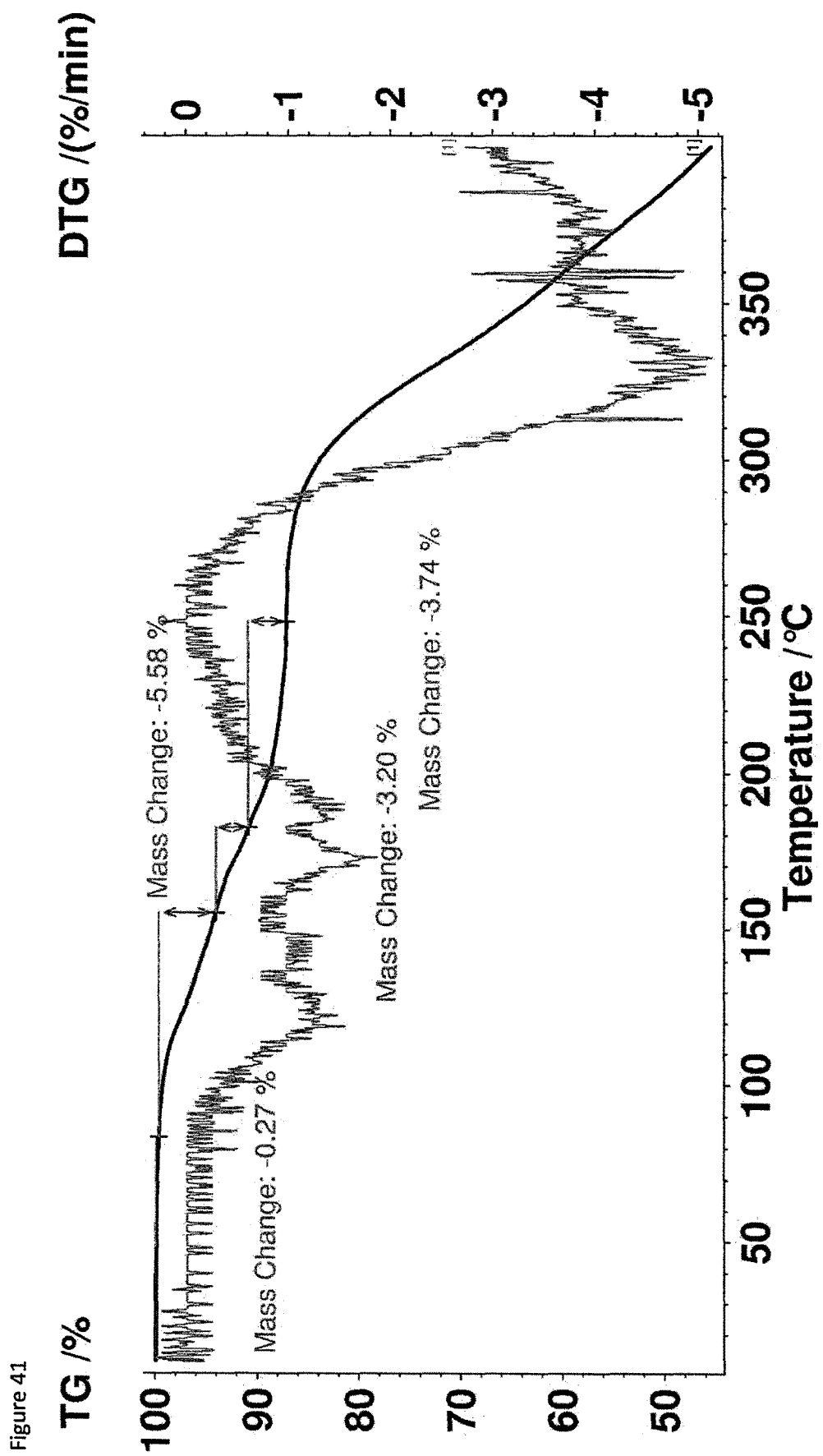
Figure 42:
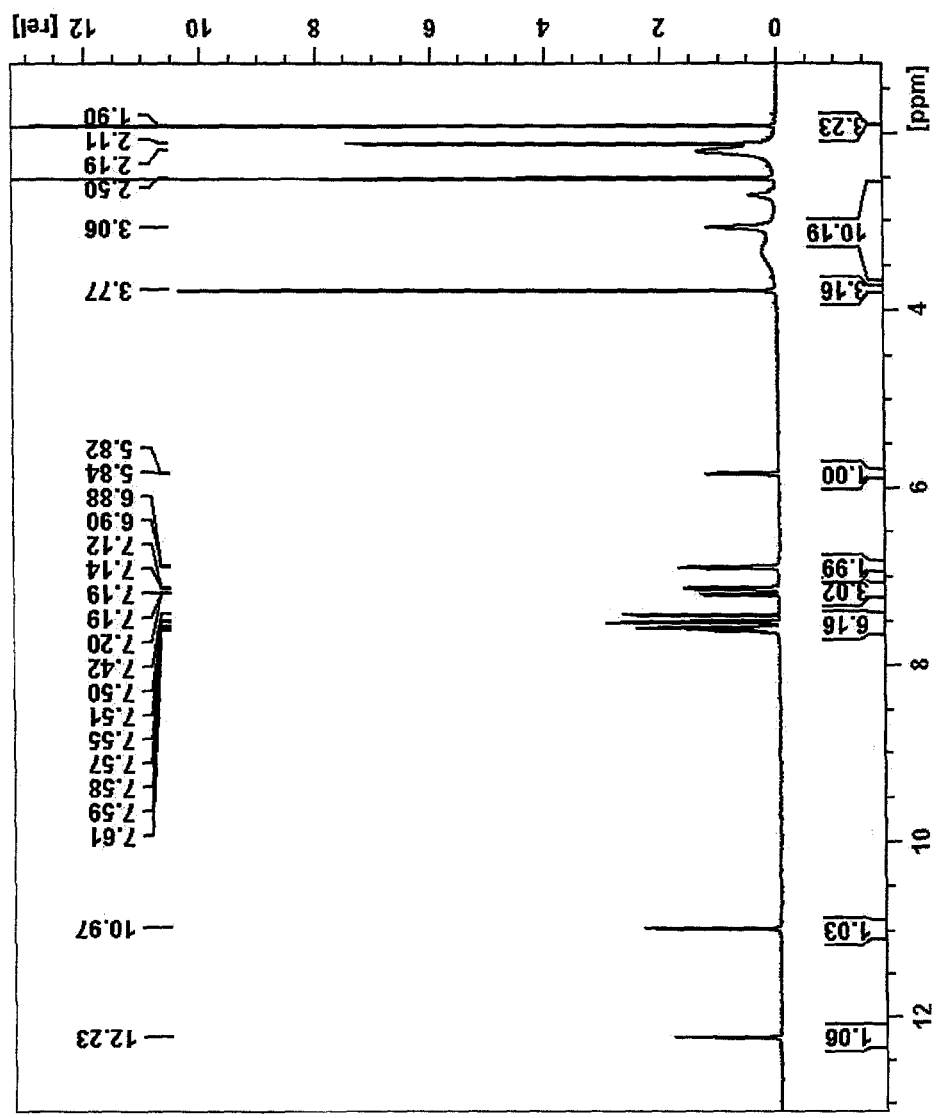
Figure 43:
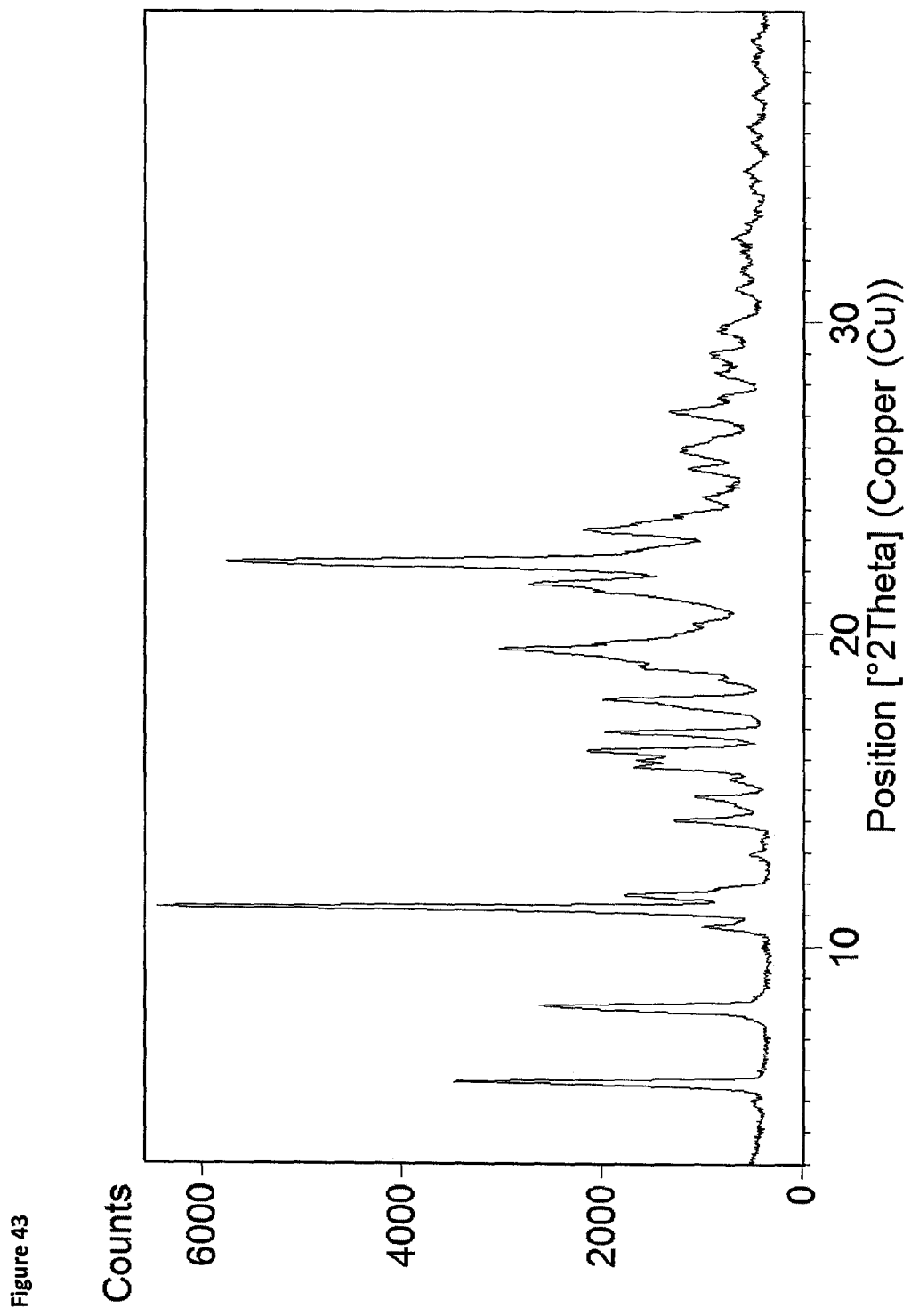
Figure 44:
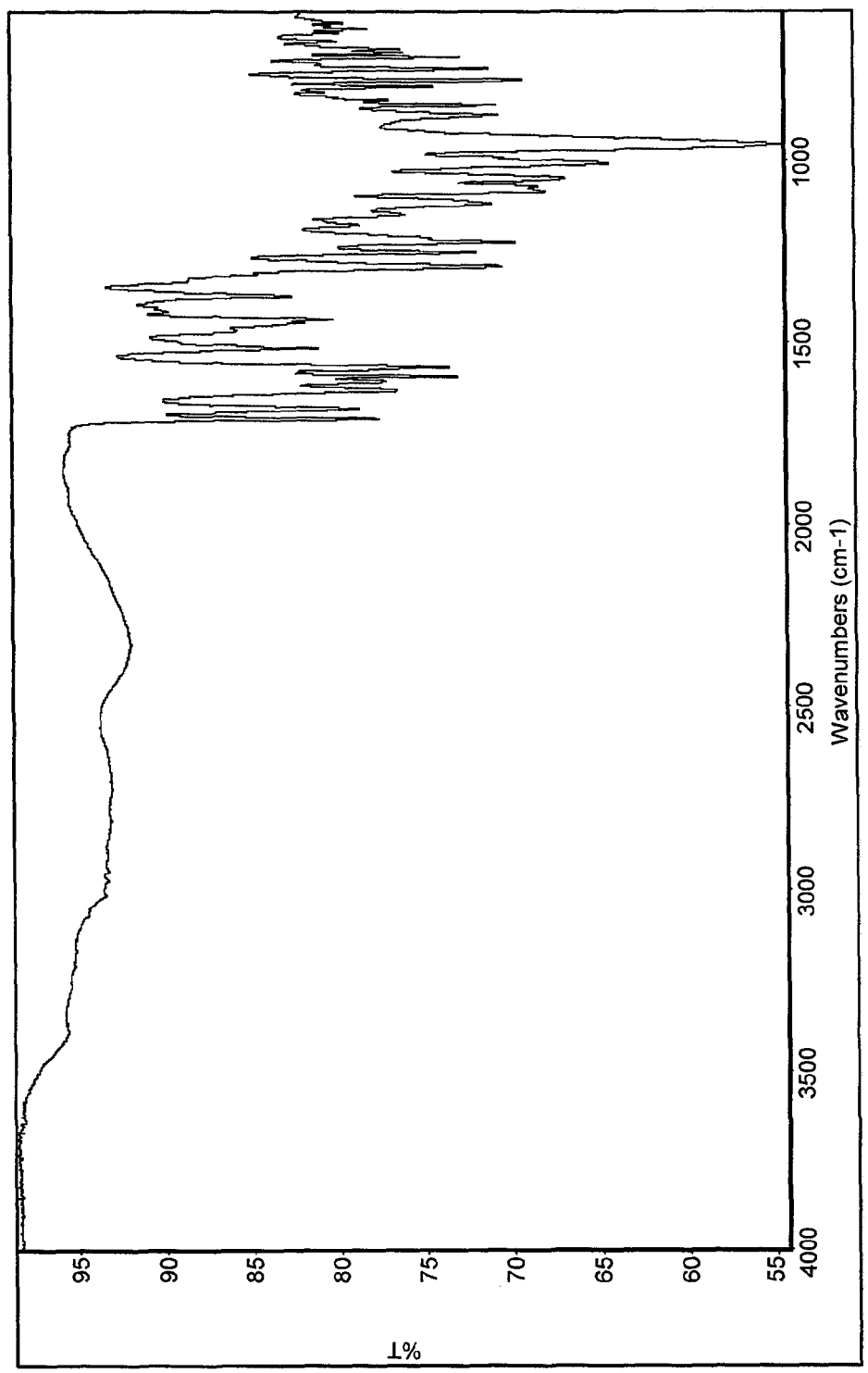
Figure 45:
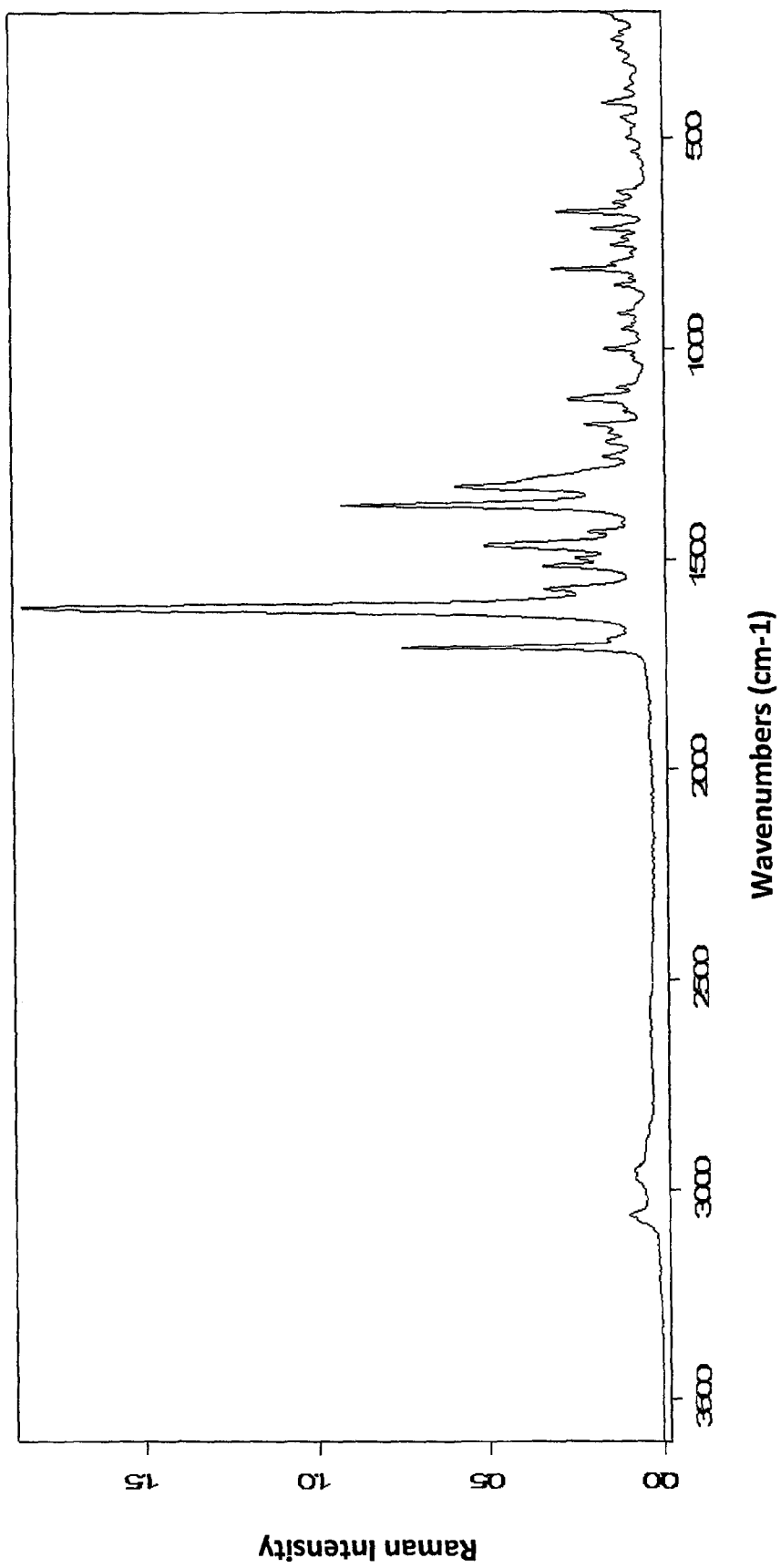
Figure 46:
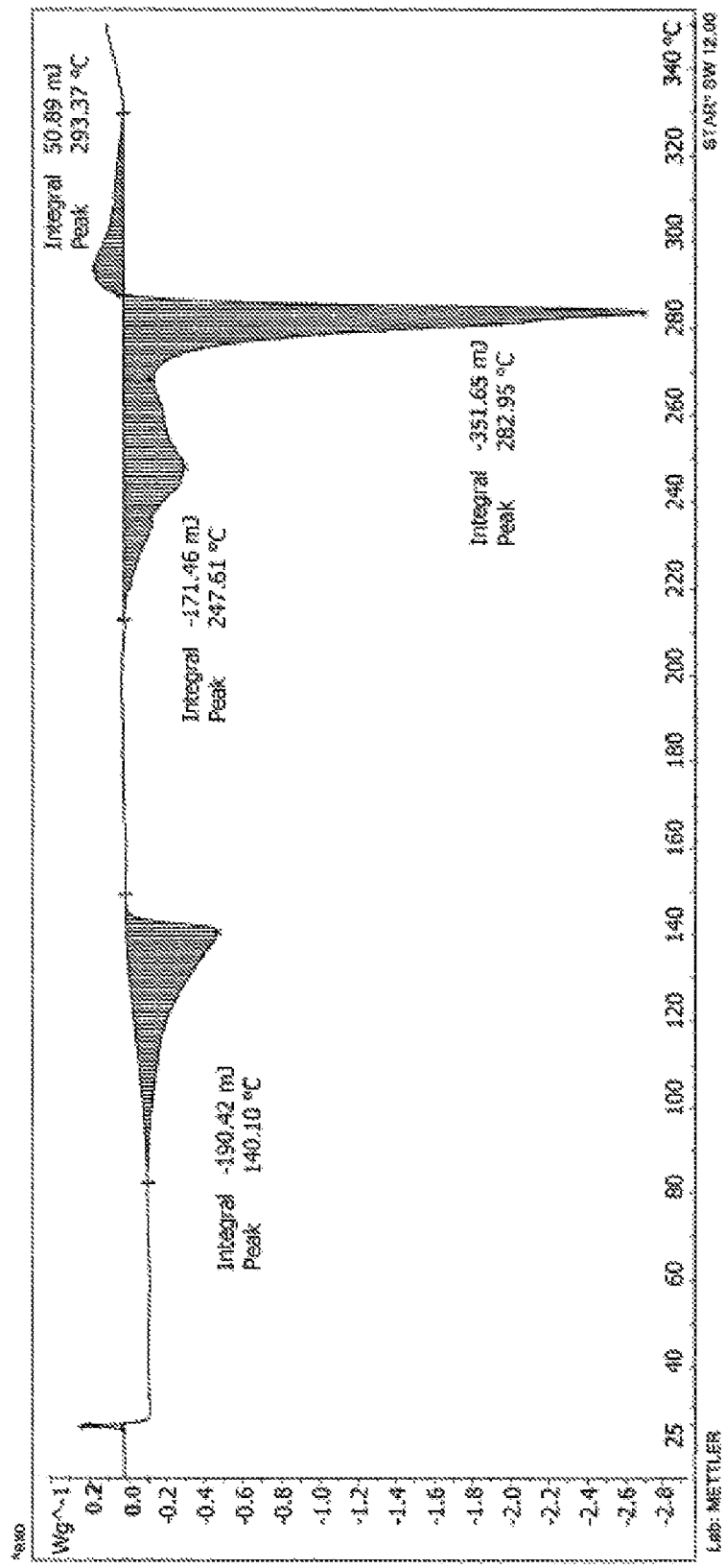
Figure 47:
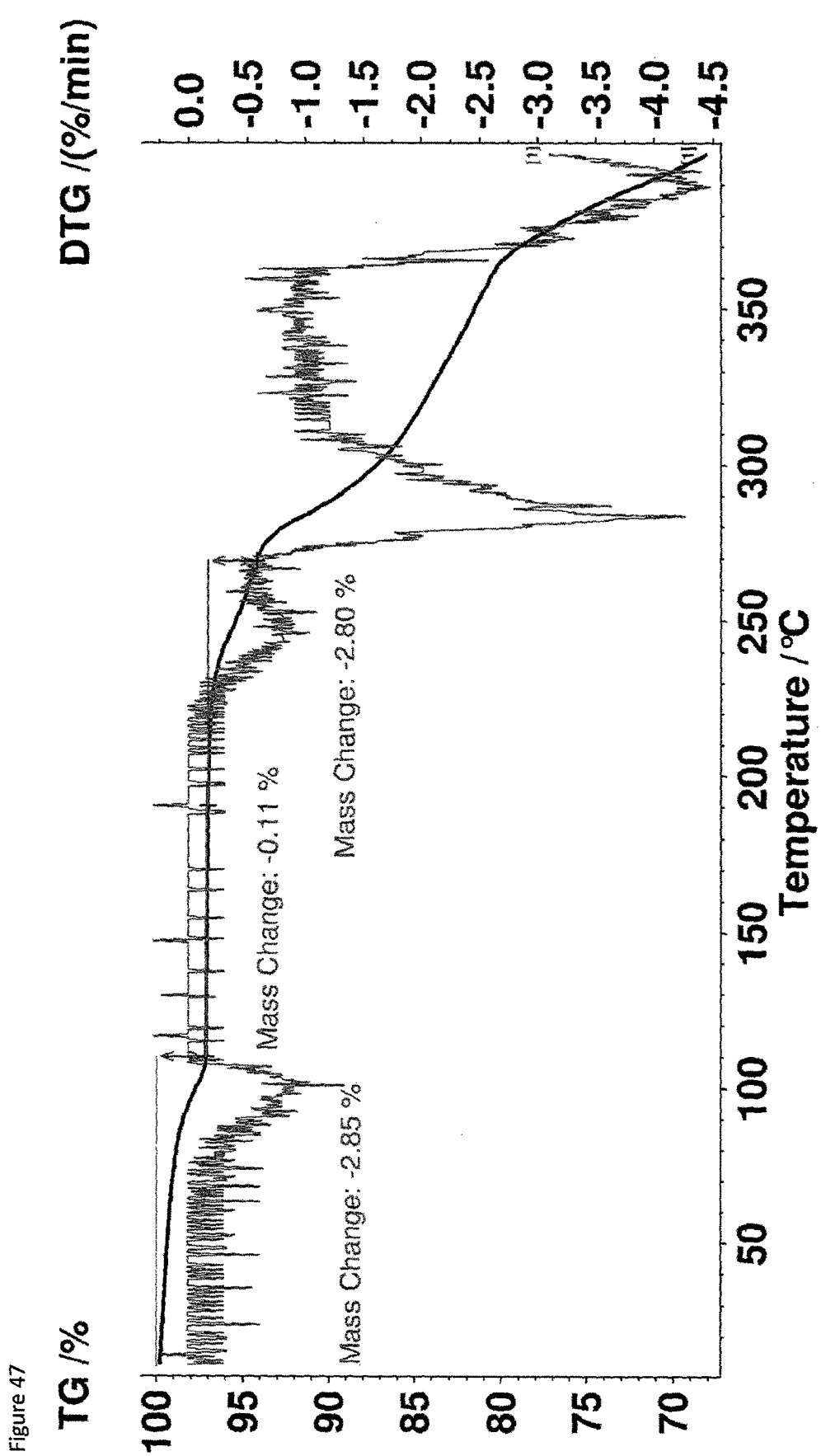
Figure 48:
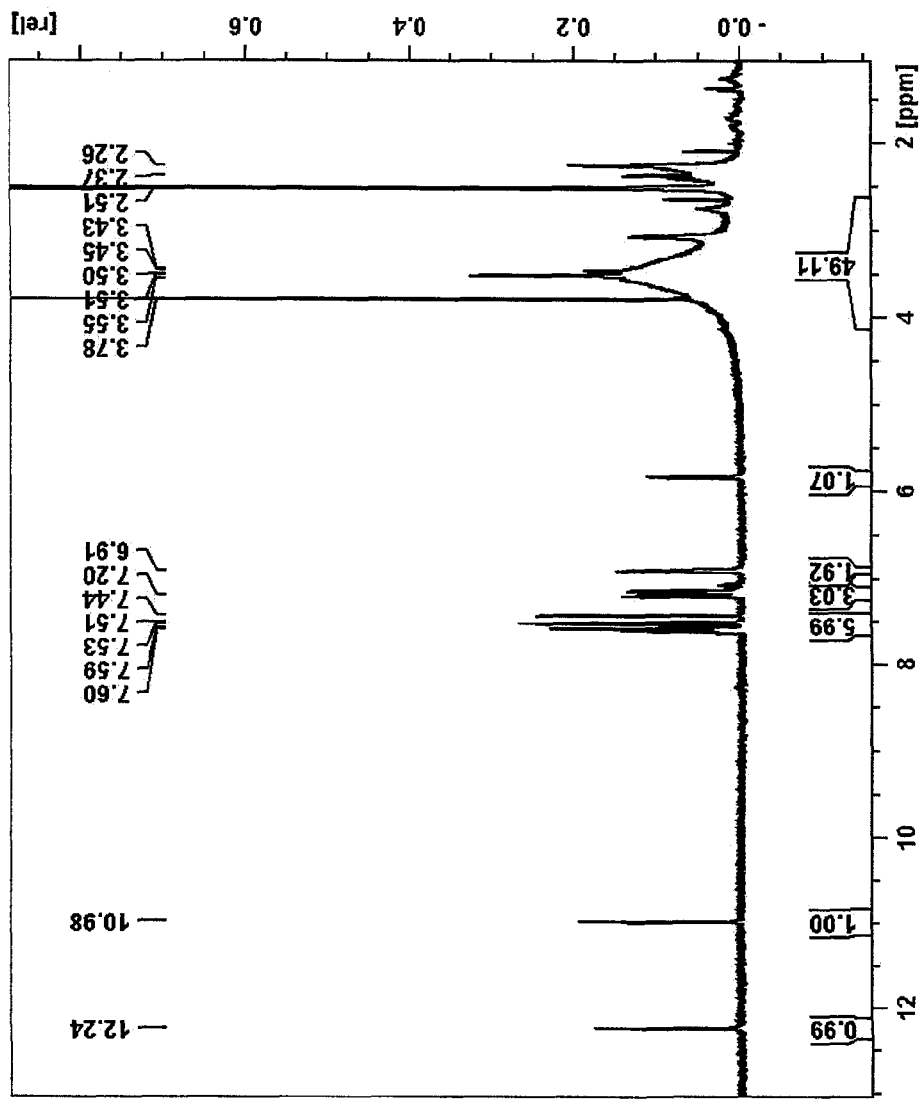

acetyl]amino}phenyl)amino](phenyl)methylidene}-2-oxo-2,3-dihydro-1H-indole-6-carboxylate p-toluenesulfonic acid salt;

FIG. 21 is a Raman spectrum of the Crystal modification 2 of methyl (3Z)-3-{[(4-{methyl[(4-methylpiperazin-1-yl)acetyl]amino}phenyl)amino]phenyl)methylidene}-2-oxo-2,3-dihydro-1H-indole-6-carboxylate p-toluenesulfonic acid salt;

FIG. 22 is a DSC curve of the Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt;

FIG. 23 is a TGA curve of the Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt;

FIG. 24 is a $^1$H-NMR spectrum of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate and p-toluenesulfonic acid salt prepared according to Example 4;

FIG. 25 is an XRPD pattern of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate L-tartaric acid salt;

FIG. 26 is an FTIR spectrum of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate L-tartaric acid salt;

FIG. 27 is a Raman spectrum of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate L-tartaric acid salt;

FIG. 28 is a DSC curve of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate L-tartaric acid salt;

FIG. 29 is a TGA curve of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate L-tartaric acid salt;

FIG. 30 is a $^1$H-NMR spectrum of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate and L-tartaric acid salt prepared according to Example 6;

FIG. 31 is an XRPD pattern of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate maleic acid salt;

FIG. 32 is an FTIR spectrum of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate maleic acid salt;

FIG. 33 is a Raman spectrum of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate maleic acid salt;

FIG. 34 is a DSC curve of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate maleic acid salt;

FIG. 35 is a TGA curve of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate maleic acid salt;

FIG. 36 is a $^1$H-NMR spectrum of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate and maleic acid salt prepared according to Example 8;

FIG. 37 is an XRPD pattern of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate acetic acid salt;

FIG. 38 is an FTIR spectrum of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate acetic acid salt;

FIG. 39 is a Raman spectrum of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate acetic acid salt;

FIG. 40 is a DSC curve of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-H-indole-6-carboxylate acetic acid salt;

FIG. 41 is a TGA curve of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate acetic acid salt;

FIG. 42 is a $^1$H-NMR spectrum of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate and acetic acid salt prepared according to Example 9;

FIG. 43 is an XRPD pattern of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate phosphoric acid salt;

FIG. 44 is an FTIR spectrum of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate phosphoric acid salt;

FIG. 45 is a Raman spectrum of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate phosphoric acid salt;

FIG. 46 is a DSC curve of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate phosphoric acid salt;

FIG. 47 is a TGA curve of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate phosphoric acid salt;

FIG. 48 is a $^1$H-NMR spectrum of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate and phosphoric acid salt prepared according to Example 10;

DETAILED DESCRIPTION OF THE INVENTION

The following description is presented to enable a person with common knowledge in the art to make and use the various embodiments. Descriptions of specific devices, techniques, and applications are provided only as examples. Various modifications to the examples described herein will be readily apparent to those with common knowledge in the art, and the general principles described herein may be applied to other examples and applications without departing from the spirit and scope of the various embodiments. Therefore, the various embodiments are not intended to be limited to the examples described herein and shown, but are to be accorded the scope consistent with the claims.

The aim of the present invention is to provide novel crystalline forms of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate salts of Formula I,

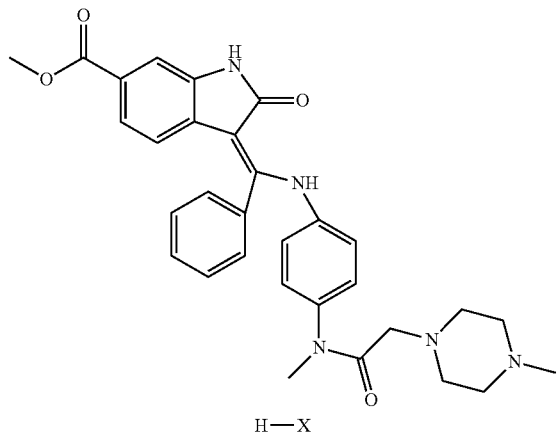

(I)

wherein HX represents at least one acid component, preferably methanesulfonic acid, p-toluenesulphonic acid, L-tartaric acid, maleic acid, acetic acid and phosphoric acid, with advantageous properties for pharmaceutical use regarding the physico-chemical properties and can be produced in a reproducible manner even in industrial scale. The invention also relates to the processes for the preparation thereof as well as said use thereof in pharmaceutically acceptable compositions. Use of said crystalline forms of intedanib and manufactured salts in the preparation of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate in the free form or in the form of any pharmaceutically acceptable salt thereof is also part of this invention.

Variations in the crystal structure of intedanib salts may affect the dissolution rate (which may affect bioavailability etc.), manufacturability (e.g., ease of handling, ability to consistently prepare doses of known strength) and stability (e.g., thermal stability, shelf life, etc.) of a pharmaceutical drug product, particularly when formulated in a solid oral dosage form (e.g., in a form of a tablet). The therapeutic use and manufacturing of intedanib involves the development of a new solid forms of intedanib salts that will be more bioavailable and stable.

The term "form, forms" of intedanib, as used in this document, is synonymous to terms "solid state form, solid state form" of intedanib and includes crystalline forms, hydrates and solvates of intedanib. The term "crystalline form" of intedanib, as used in this document, is synonymous to commonly used expressions "polymorphic form" or "crystalline modification" of intedanib.

The use of the term "about" includes and describes the value or parameter per se. For example, "about x" includes and describes "x" per se. In some embodiments, the term "about" when used in association with a measurement, or used to modify a value, a unit, a constant, or a range of values, refers to variations of +/−20 percent, preferably +/−10 percent and more preferably +/−5 percent.

The term "substantially" or "substantially free/pure" with respect to a particular solid form of a compound means that the polymorphic form contains about less than 30 percent, about less than 20 percent, about less than 15 percent, about less than 10 percent, about less than 5 percent, or about less than 1 percent by weight of impurities. In other embodiments, "substantially" or "substantially free/pure" refers to a substance free of impurities. Impurities may, for example, include by-products or left over reagents from chemical reactions, contaminants, degradation products, other polymorphic forms, water, and solvents.

It has now been surprisingly found that the above-mentioned crystal modifications of salts of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate with at least one acid component HX, wherein HX is preferably methanesulfonic acid, p-toluenesulphonic acid, L-tartaric acid, maleic acid, acetic acid and phosphoric acid can be prepared and have not been described in the literature yet and no solid state analytical data (X-Ray Powder Diffraction patterns, Single-Crystal X-Ray Diffraction data etc.) serving to characterize the crystalline phases have been provided.

Figure 1:
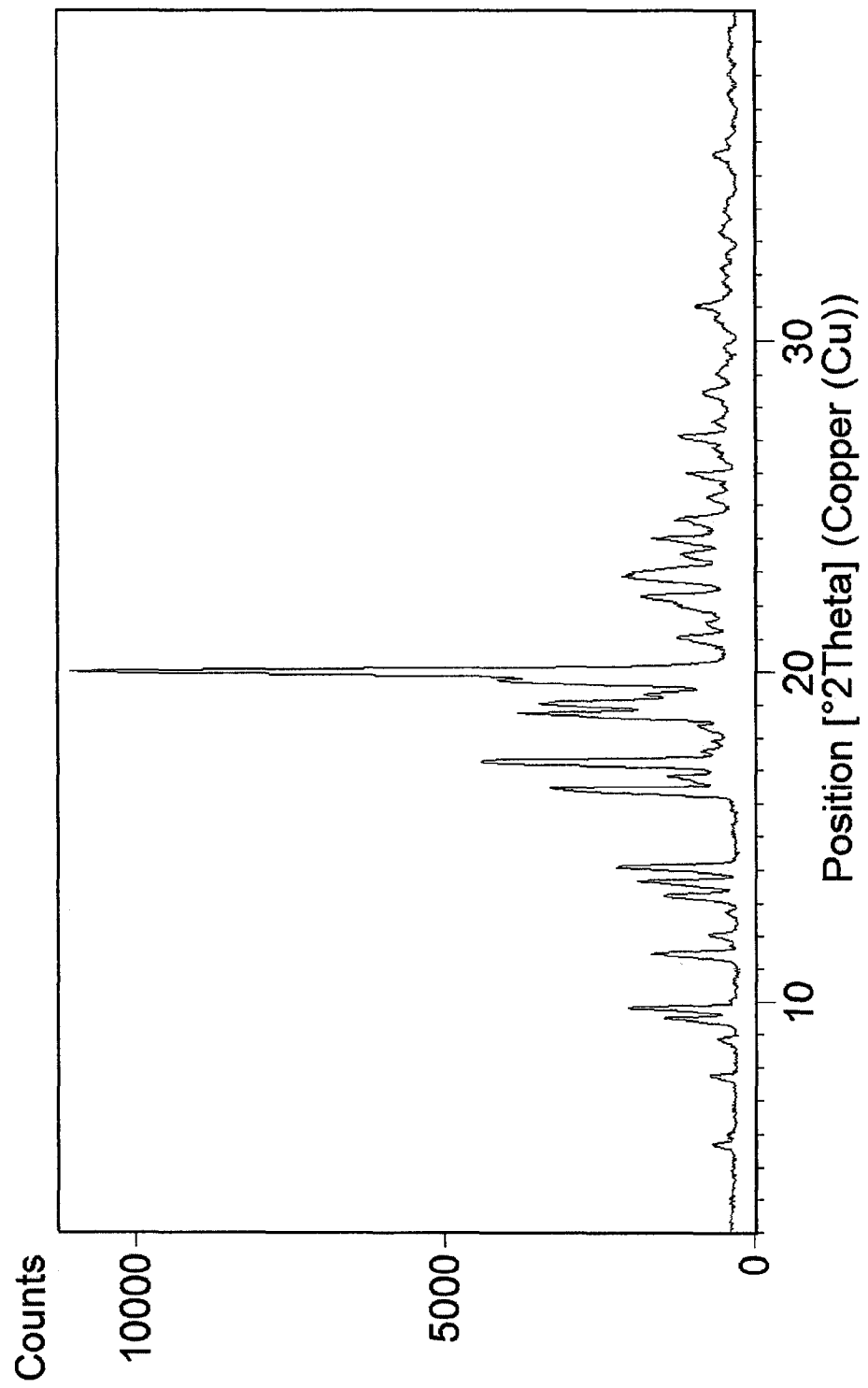
FIG. 1 is an XRPD pattern of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt.

The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt according to the invention has the characteristic XRPD pattern as shown in FIG. 1. XRPD pattern was recorded on an X-Ray Powder Diffractometer (X'PERT PRO MPD PANalytical). The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt exhibits the following diffraction peaks in XRPD pattern, see Table 1, below:

TABLE 1

| Pos. [°2Th.] | d [Å] | Rel. Int. [%] |
|---|---|---|
| 5.68 | 15.561 | 2.9 |
| 7.72 | 11.450 | 3.8 |
| 8.81 | 10.025 | 2.5 |
| 9.46 | 9.346 | 10.5 |
| 9.78 | 9.037 | 16.0 |
| 11.49 | 7.692 | 8.7 |
| 12.03 | 7.353 | 4.5 |
| 13.21 | 6.699 | 10.8 |
| 13.62 | 6.494 | 13.5 |
| 14.07 | 6.291 | 17.4 |
| 16.45 | 5.386 | 16.8 |
| 16.78 | 5.278 | 8.8 |
| 17.19 | 5.154 | 34.7 |
| 18.75 | 4.730 | 23.7 |
| 18.96 | 4.678 | 21.8 |
| 19.30 | 4.596 | 10.9 |
| 19.76 | 4.490 | 21.8 |
| 19.98 | 4.440 | 100.0 |
| 21.00 | 4.227 | 7.2 |
| 22.26 | 3.991 | 11.3 |
| 23.01 | 3.862 | 10.2 |
| 23.48 | 3.786 | 6.3 |
| 23.96 | 3.712 | 10.1 |
| 24.53 | 3.626 | 7.0 |
| 25.23 | 3.527 | 3.4 |
| 25.91 | 3.436 | 6.1 |

TABLE 1-continued

| Pos. [°2Th.] | d [Å] | Rel. Int. [%] |
| --- | --- | --- |
| 27.08 | 3.290 | 8.4 |
| 28.43 | 3.137 | 5.0 |
| 30.62 | 2.918 | 3.0 |
| 31.02 | 2.881 | 5.5 |
| 35.58 | 2.521 | 3.0 |

Figure 2:
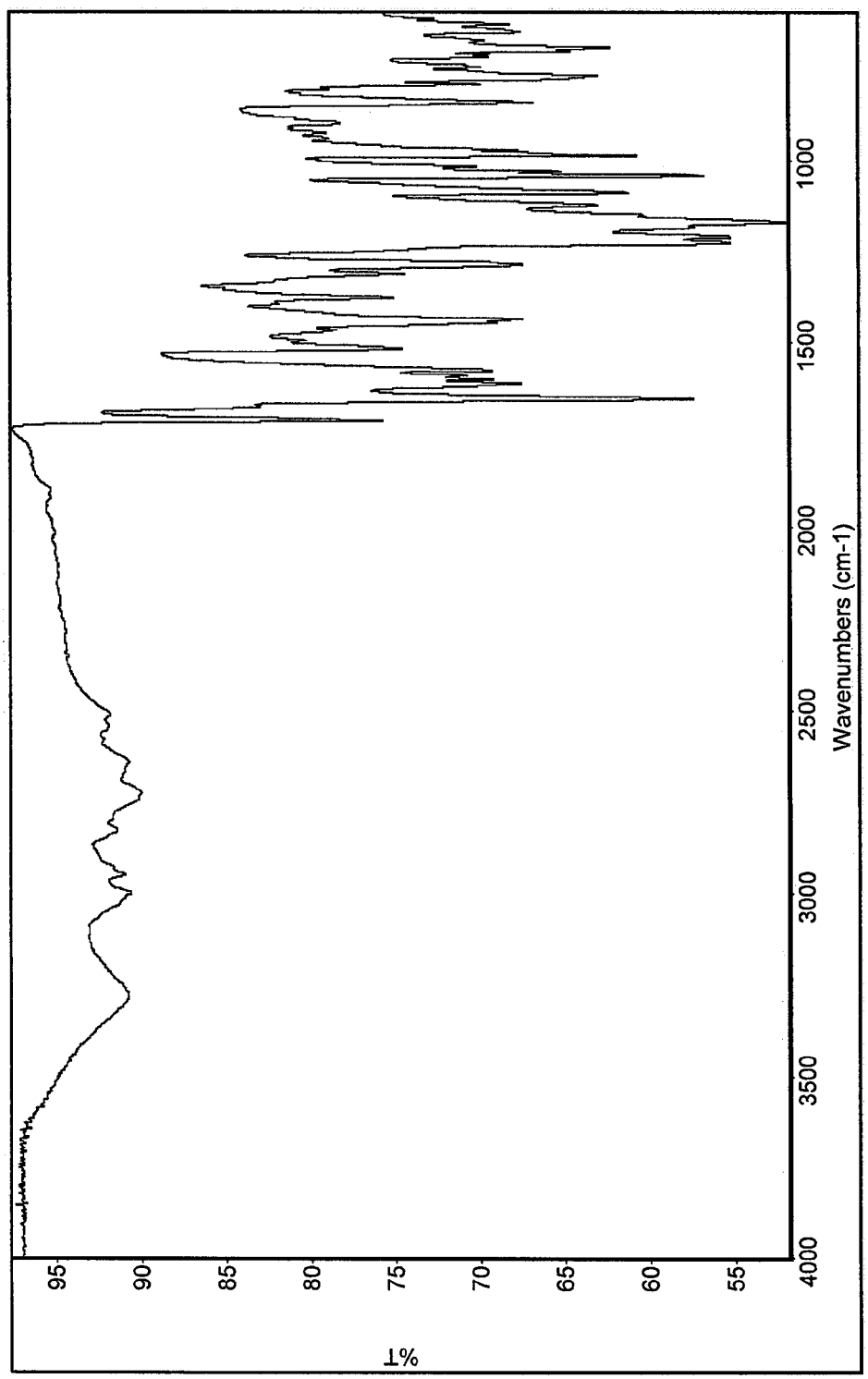
FIG. 2 is an FTIR spectrum of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt.
Figure 3:
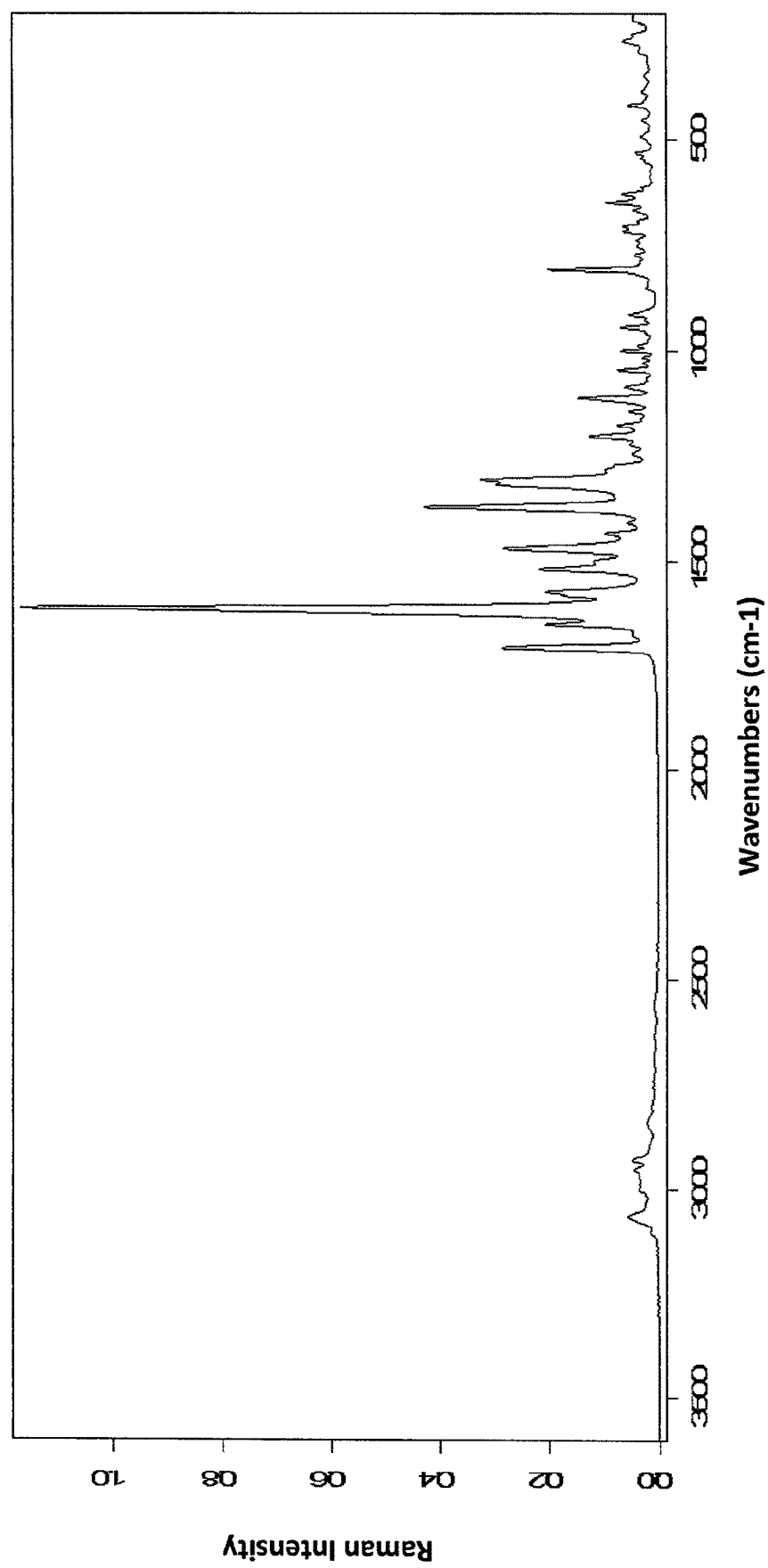
FIG. 3 is a Raman spectrum of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-H-indole-6-carboxylate methanesulfonic acid salt.

The Crystal form 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt can be characterized by FTIR and Raman spectroscopy. FIG. 2 shows the FTIR spectrum (Nicolet Thermo 6700c) comprising characteristic peaks at 3275, 3001, 2950, 2828, 2509, 1708, 1650, 1166, 1041 and 842 cm$^{-1}$ wavenumbers. The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt is characterised by a Raman spectrum (Bruker RFS 100/5) comprising characteristic peaks at 3065, 2953, 2930, 1709, 1651, 1613, 1376, 1312, 810 and 417 cm$^1$ wavenumbers, shown in FIG. 3.

Figure 4:
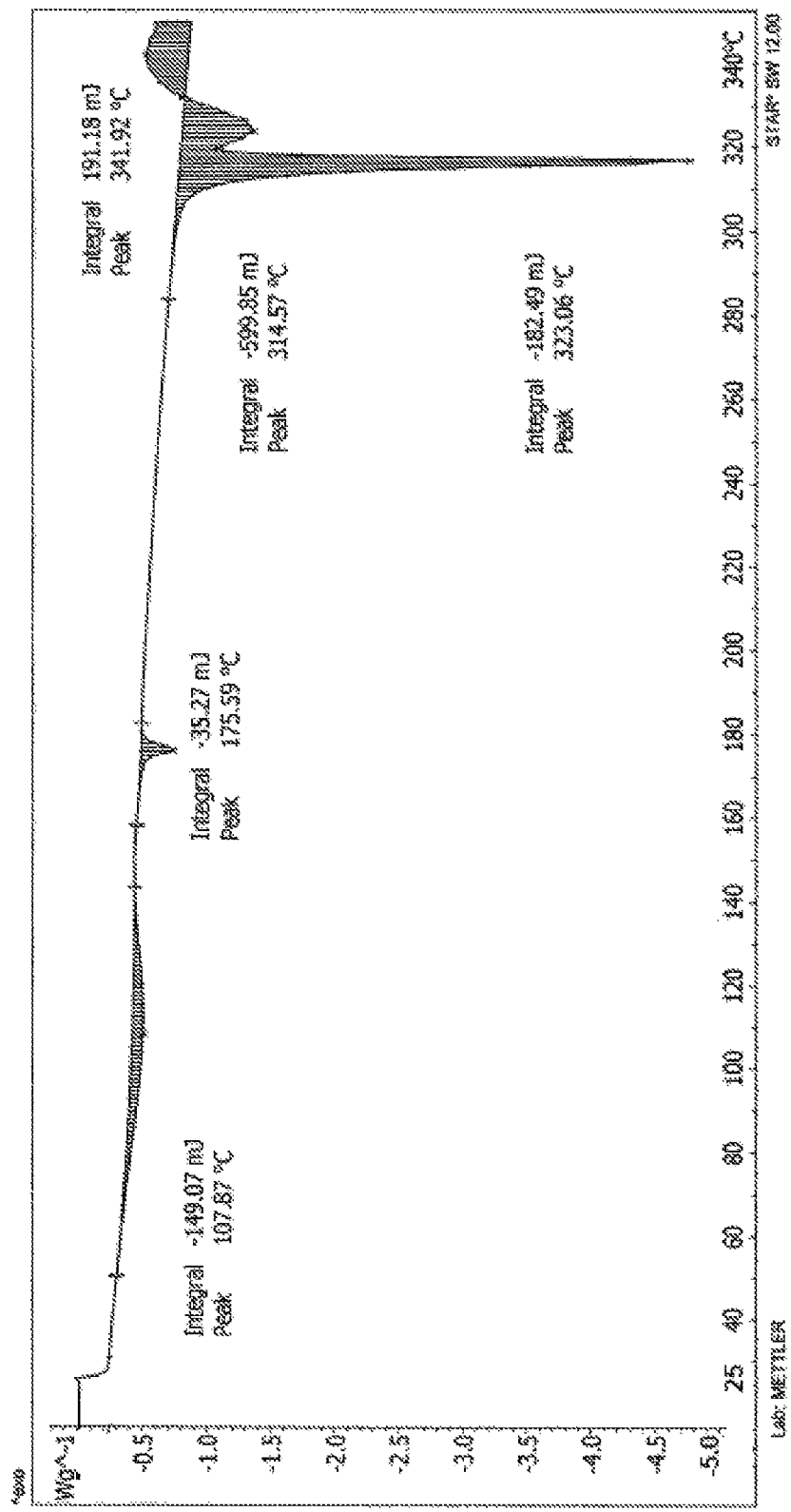
FIG. 4 is a DSC curve of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt.
Figure 5:
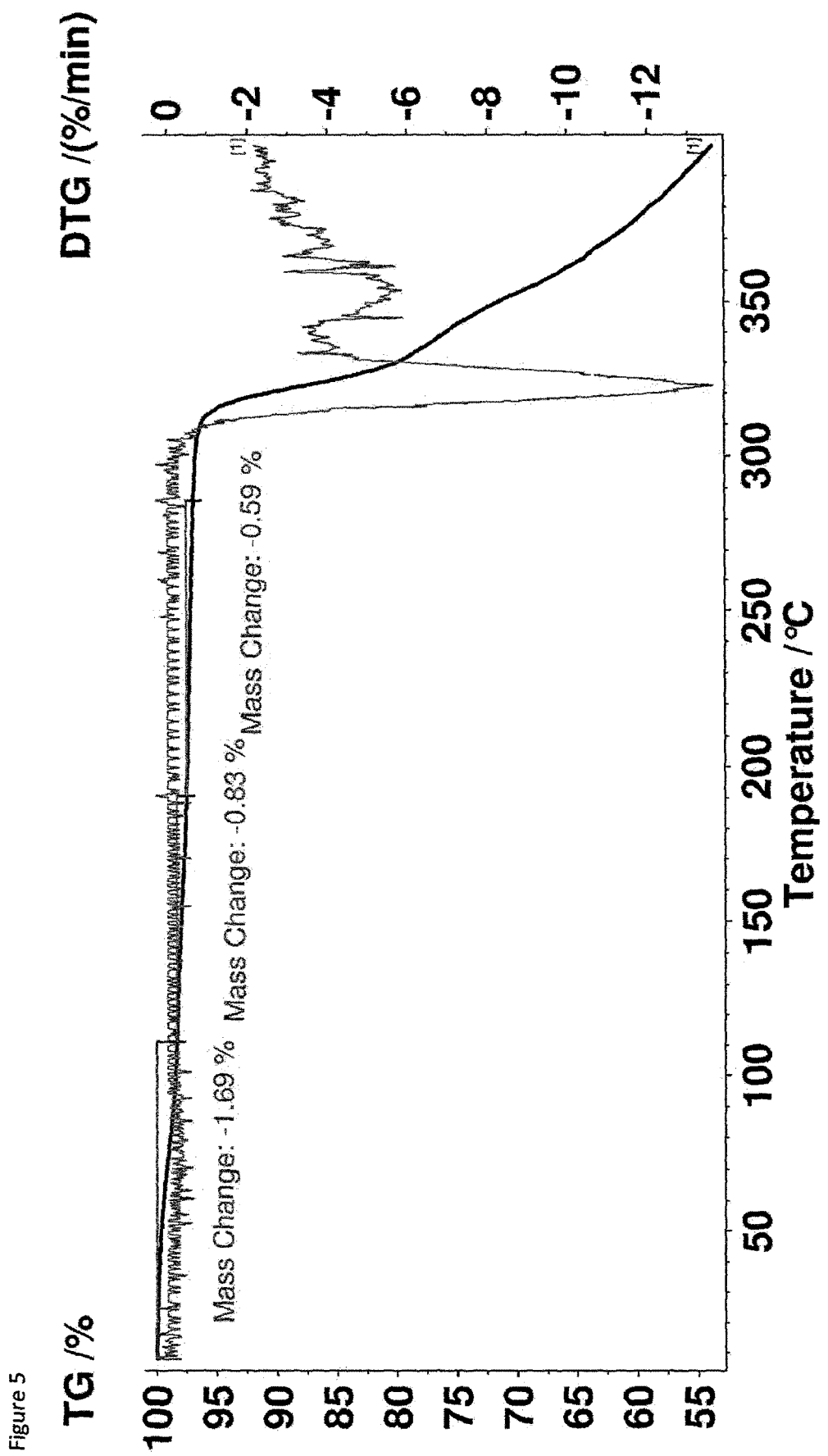
FIG. 5 is a TGA curve of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt.

The Crystal form 1 of methyl (3Z)-3-{[(4-{methyl[(4-methylpiperazin-1-yl)acetyl]amino}phenyl)amino]-(phenyl)methylidene}-2-oxo-2,3-dihydro-1H-indole-6-carboxylate methanesulfonic acid salt can be further described by thermal analytical methods. FIG. 4 shows the DSC (Mettler-Toledo 822e DSC) and FIG. 5 shows the TGA (NETZSCH TG 209 thermogravimetric analyser) curves measured in the range of 25° C. to 350° C. and 25° C. to 400° C. The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt shows a 1.69% weight loss in the range of 25° C. to 110° C. indicating that the solid form is a hemihydrate. The DSC measurement gives a melting process with $T_{desolvation1}$=107.9° C., $T_{desolvation2}$=175.6° C., $T_{peak}$=314.6° C.

It is worthy of note that the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt exhibit 10° C. higher melting point compared to (3Z)-3-{[(4-{methyl[(4-methylpiperazin-1-yl)acetyl]amino}phenyl)amino](phenyl)methylidene}-2-oxo-2,3-dihydro-1H-indole-6-carboxylate ethanesulfonic acid salt hemihydrate described in the patent WO2004013099, hence Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt is expected to have superior stability. The higher melting point is a good indication that the above mentioned Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt is likely to have increased physical and chemical stability.

In one of the objects of the invention, process for preparation of the Crystal modification 1 is provided. In this process, intedanib free base is suspended in a suitable organic solvent and heated to a temperature 60° C. The methanesulfonic acid is added to the solution. The suitable organic solvent is preferably a polar protic solvent selected from the group consisting of: methanol, ethanol, 1-propanol, 2-propanol, 1-butanol, 2-butanol or a mixture thereof, more preferably in methanol, even more preferably methanol at the temperature of 60° C.

The Crystal form 1 of intedanib methanesulfonic acid salt can be prepared by a process comprising the following steps:
a/ suspending intedanib free base in a suitable organic solvent at 60° C.;
b/ drop-wise addition of the aqueous solution of the methanesulfonic acid, resulting in a clear solution;
c/ stirring the solution of step b/ at 60° C. for additional 1 hour;
d/ cooling the solution of the step c/ to 44° C. where it is seeded and precipitation occurs;
e/ cooling the suspension of step d/ to 0-5° C.;
f/ keeping the suspension of step e/ for 16 hours at a temperature of 0-5° C.;
g/ isolating the intedanib methanesulfonic acid salt in Crystal form 1
h/ optionally, drying the product of step g/ under the laboratory conditions until the constant weight of the product is reached The suitable organic solvent is preferably a polar protic solvent, more preferably the polar protic solvent is selected from the group consisting of: methanol, ethanol, 1-propanol, 2-propanol, 1-butanol, 2-butanol or a mixture thereof, even more preferably the suitable organic solvent is ethanol and even more preferably the suitable organic solvent is methanol at the temperature of 60° C.

Figure 7:
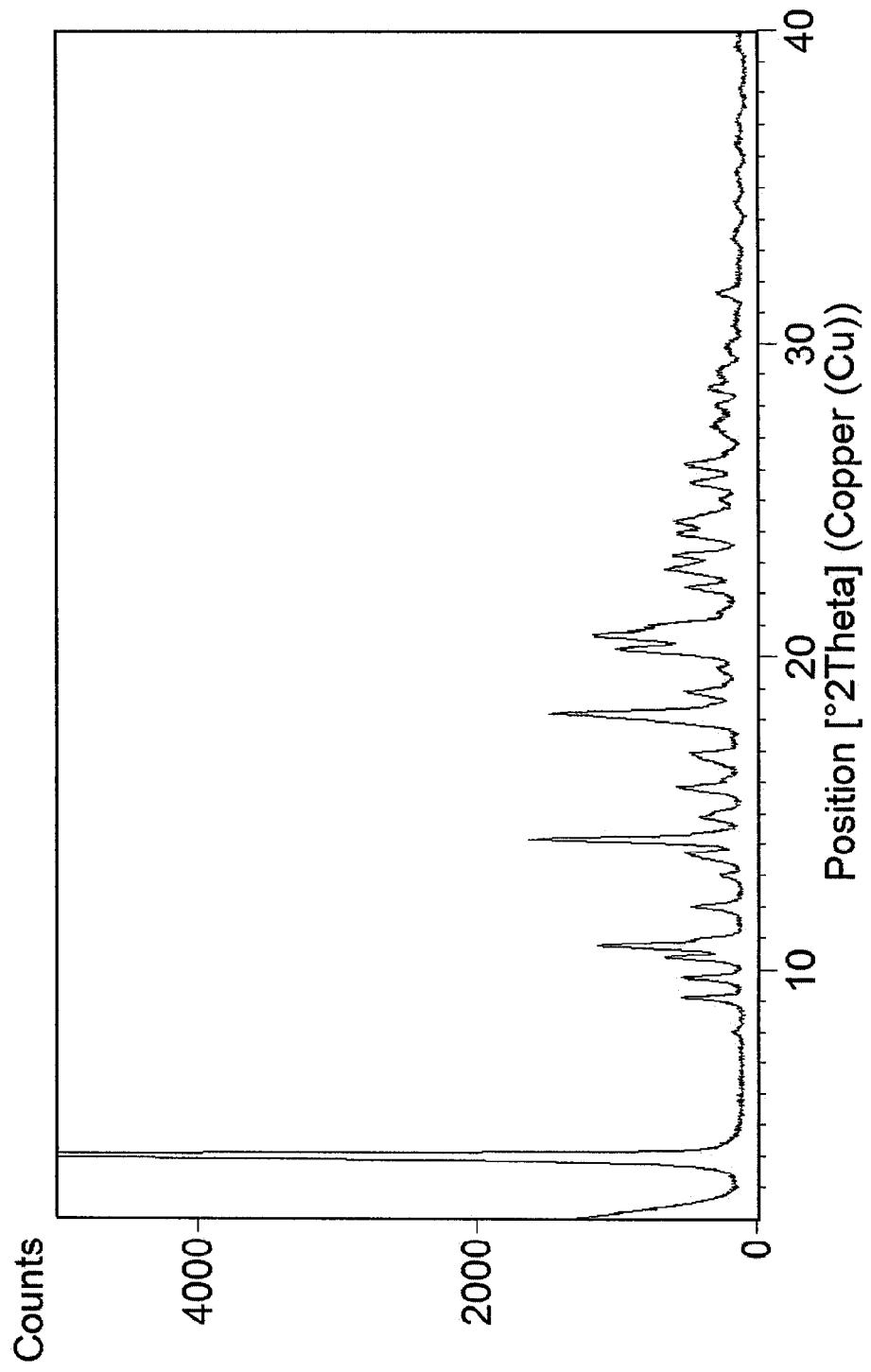
FIG. 7 is an XRPD pattern of the Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt.

The Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt according to the invention has the characteristic XRPD pattern as shown in FIG. 7. XRPD pattern was recorded on an X-Ray Powder Diffractometer (X'PERT PRO MPD PANalytical). The Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt exhibits the following diffraction peaks in XRPD pattern, see Table 2, below:

TABLE 2

| Pos. [°2Th.] | d [Å] | Rel. Int. [%] |
| --- | --- | --- |
| 3.98 | 22.169 | 100.0 |
| 9.10 | 9.711 | 6.2 |
| 9.73 | 9.079 | 6.1 |
| 10.37 | 8.521 | 7.3 |
| 10.73 | 8.238 | 14.9 |
| 11.97 | 7.390 | 4.9 |
| 12.96 | 6.827 | 2.0 |
| 13.63 | 6.493 | 6.5 |
| 14.13 | 6.262 | 21.2 |
| 14.87 | 5.951 | 4.1 |
| 15.81 | 5.602 | 6.5 |
| 16.82 | 5.267 | 5.4 |
| 18.13 | 4.888 | 18.3 |
| 18.87 | 4.700 | 4.8 |
| 20.20 | 4.392 | 11.4 |
| 20.59 | 4.311 | 10.8 |
| 22.15 | 4.009 | 5.3 |
| 22.77 | 3.903 | 6.7 |
| 23.20 | 3.830 | 5.9 |
| 23.84 | 3.729 | 4.4 |
| 24.32 | 3.657 | 5.7 |
| 25.56 | 3.482 | 4.6 |
| 26.15 | 3.405 | 5.1 |
| 27.37 | 3.256 | 2.3 |
| 27.98 | 3.186 | 2.1 |
| 28.55 | 3.124 | 3.0 |

TABLE 2-continued

| Pos. [°2Th.] | d [Å] | Rel. Int. [%] |
|---|---|---|
| 29.03 | 3.073 | 2.0 |
| 31.59 | 2.830 | 2.2 |

Figure 8:
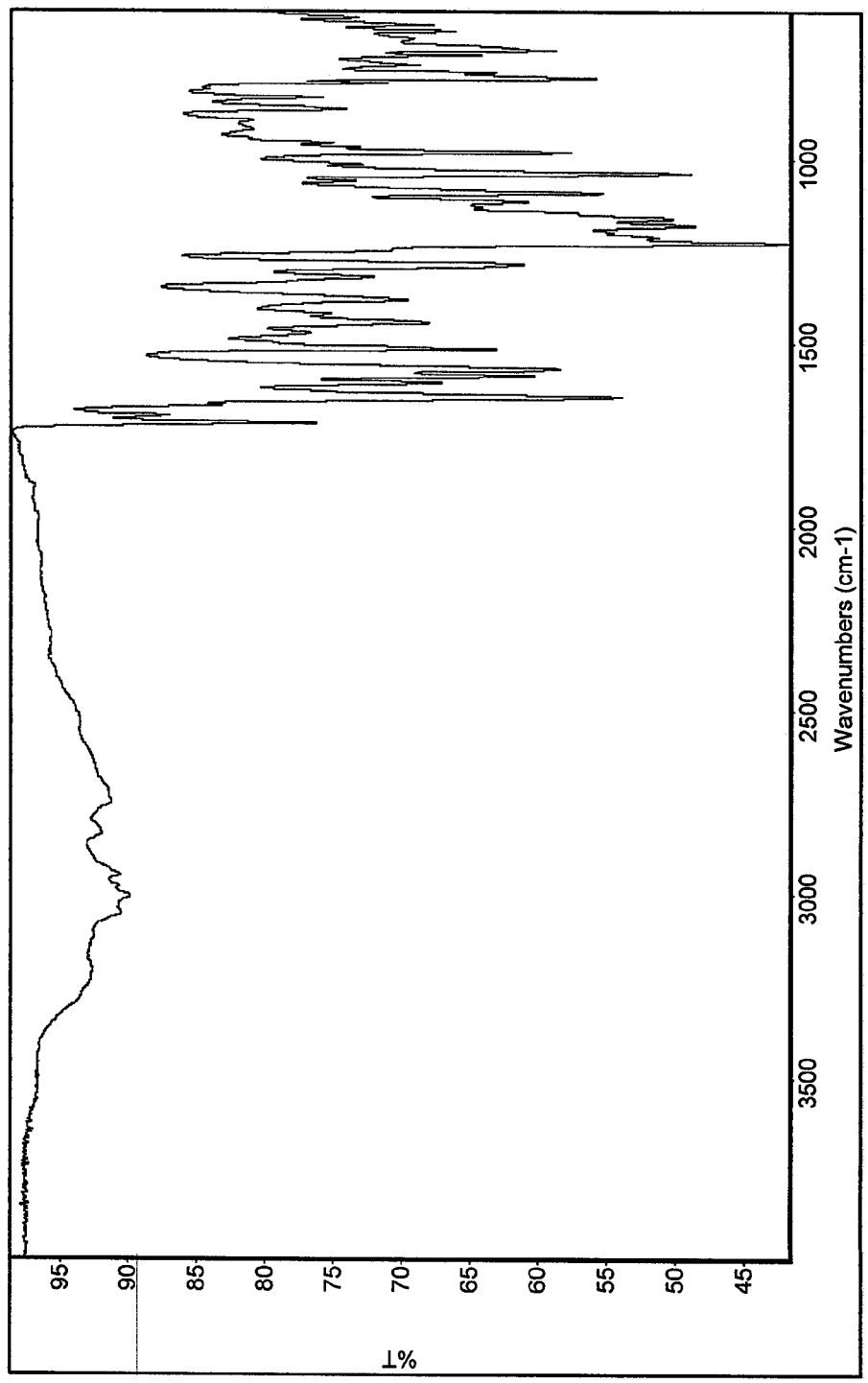
FIG. 8 is an FTIR spectrum of the Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt.
Figure 9:
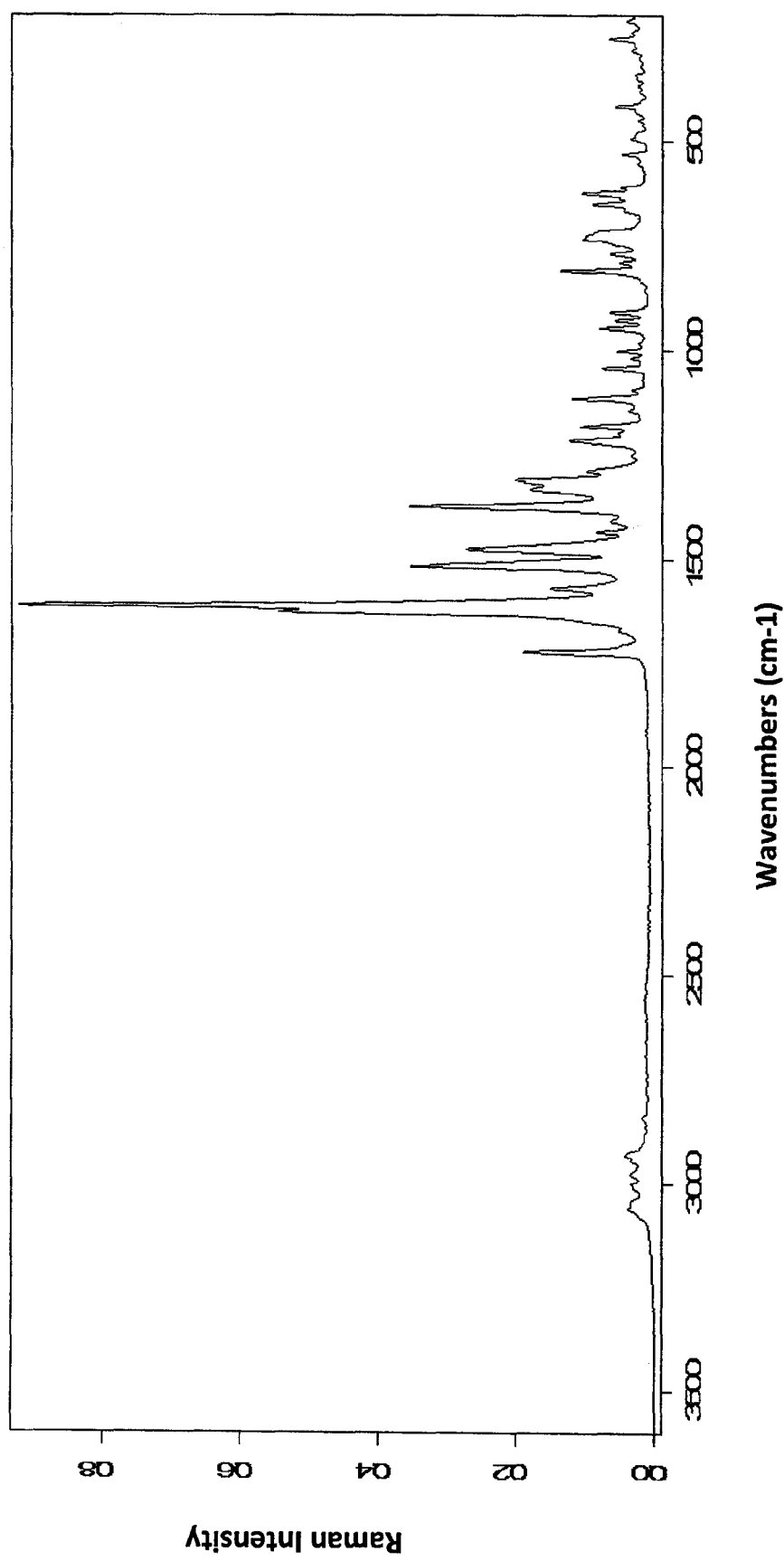
FIG. 9 is a Raman spectrum of the Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt.

The Crystal form 2 of methyl (3Z)-3-{[(4-{methyl[(4-methylpiperazin-1-yl)acetyl]amino}phenyl)-amino](phenyl)methylidene}-2-oxo-2,3-dihydro-1H-indole-6-carboxylate methanesulfonic acid salt can be characterized by FTIR and Raman spectroscopy. FIG. 8 shows the FTIR spectrum (Nicolet Thermo 6700c) comprising characteristic peaks at 3006, 2950, 2836, 2748, 1720, 1672, 1282, 1209, 1037 and 779 cm$^{-1}$ wavenumbers. The Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt is characterised by a Raman spectrum (Bruker RFS 100/S) comprising characteristic peaks at 3061, 3002, 2980, 2933, 1725, 1613, 1518, 1377, 811 and 256 cm$^{-1}$ wavenumbers, shown in FIG. 9.

Figure 10:
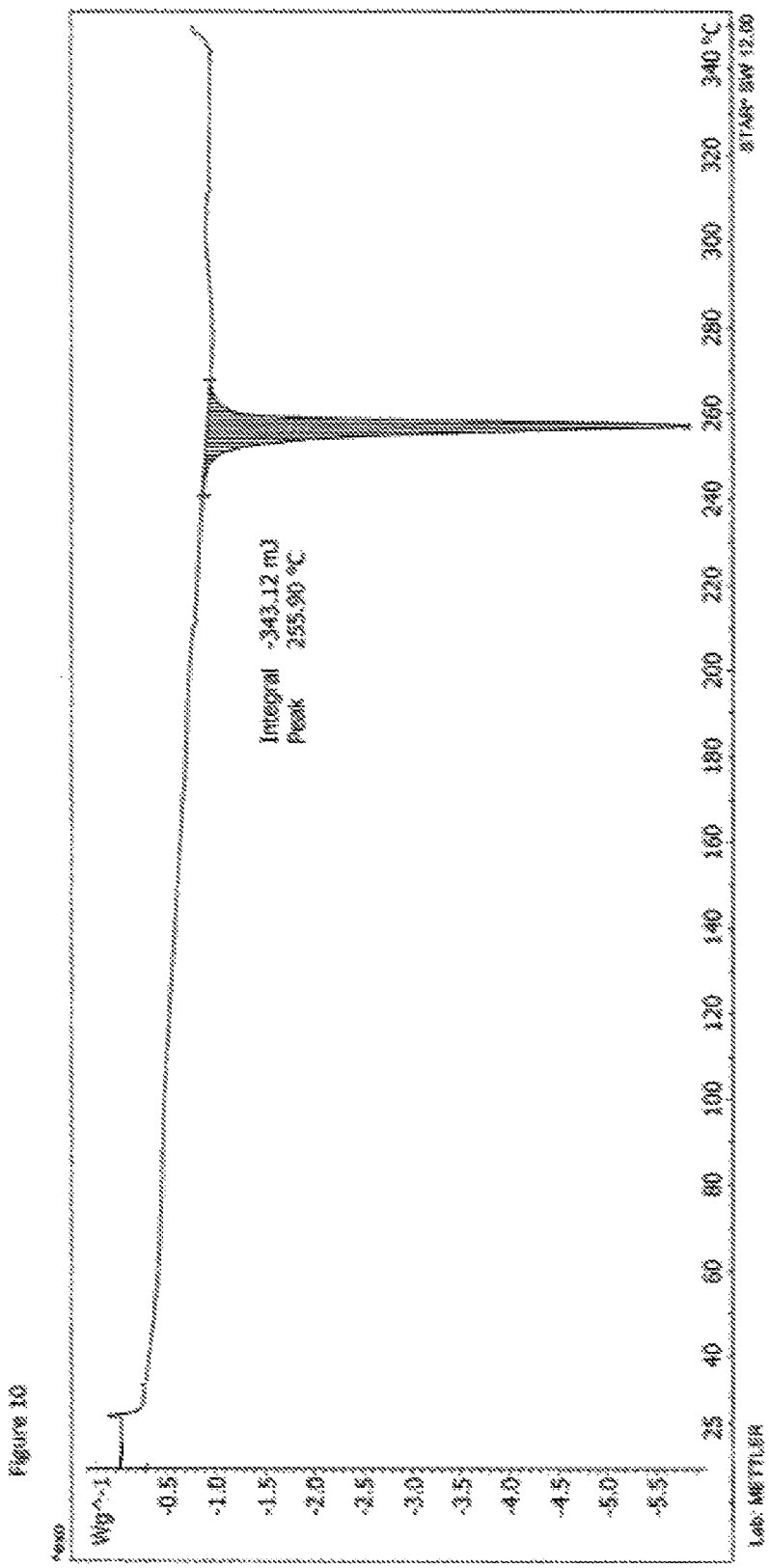
FIG. 10 is a DSC curve of the Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt.
Figure 11:
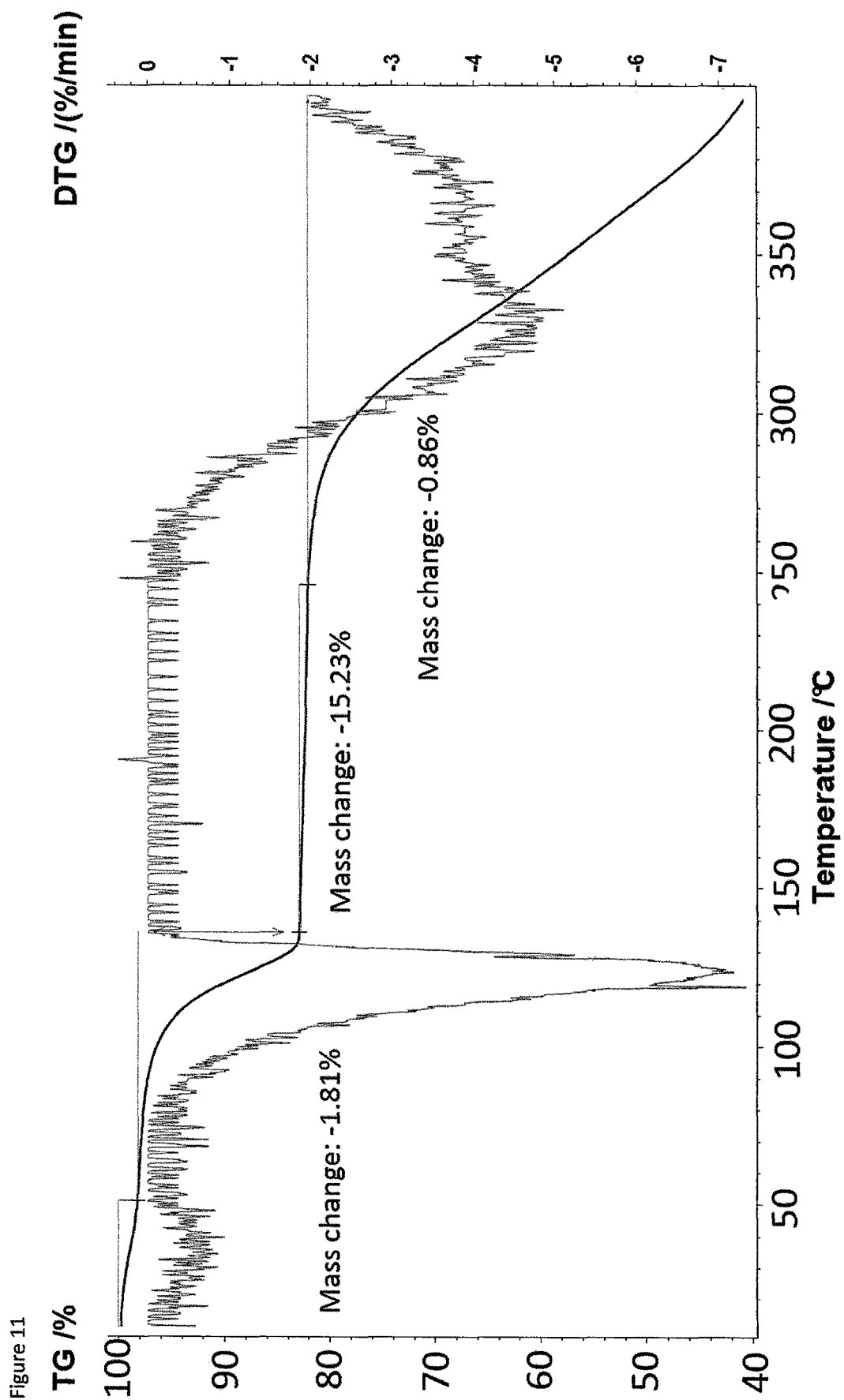
FIG. 11 is a TGA curve of the Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt.

The Crystal form 2 of methyl (3Z)-3-{[(4-{methyl[(4-methylpiperazin-1-yl)acetyl]amino}phenyl)amino]-(phenyl)methylidene}-2-oxo-2,3-dihydro-1H-indole-6-carboxylate methanesulfonic acid salt can be further described by thermal analytical methods. FIG. 10 shows the DSC (Mettler-Toledo 822e DSC) and FIG. 11 shows the TGA (NETZSCH TG 209 thermogravimetric analyser) curves measured in the range of 25° C. to 350° C. and 25° C. to 400° C. The Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt shows a 2.53% weight loss in the range of 25° C. to 229° C. The DSC measurement gives a melting process with $T_{peak}$=255.9° C.

In one of the objects of the invention, process for preparation of the Crystal modification 2 is provided. In this process, intedanib free base is suspended in a suitable organic solvent and heated to a temperature 50° C. Then 2 molar equivalent of methanesulfonic acid is added to the solution. The suitable organic solvent is preferably a polar protic solvent selected from the group consisting of: methanol, ethanol, 1-propanol, 2-propanol, 1-butanol, 2-butanol or a mixture thereof, more preferably in methanol, even more preferably methanol at the temperature of 50° C.

The process of preparation of the Crystal modification 2 of intedanib methanesulfonic acid salt thus comprises the following steps:

a/ suspending intedanib free base in a suitable organic solvent at 50° C.;
b/ drop-wise addition of the methanesulfonic acid >98% aqueous solution inducing dissolution followed by precipitation;
c/ stirring the suspension of step b/ at 50° C. for additional 1 hour;
d/ cooling the suspension of step c/ to a temperature of 0-5° C.;
e/ keeping the suspension of step d/ for 16 hours at a temperature of 0-5° C.;
f/ isolating the intedanib methanesulfonic acid salt in Crystal form 2;
g/ optionally, drying the product of step f/ under the laboratory conditions until the constant weight of the product is reached.

The suitable organic solvent is preferably a polar protic solvent selected from the group consisting of: methanol, ethanol, 1-propanol, 2-propanol, 1-butanol, 2-butanol or a mixture thereof, more preferably in methanol, even more preferably methanol at the temperature of 50° C.

Figure 13:
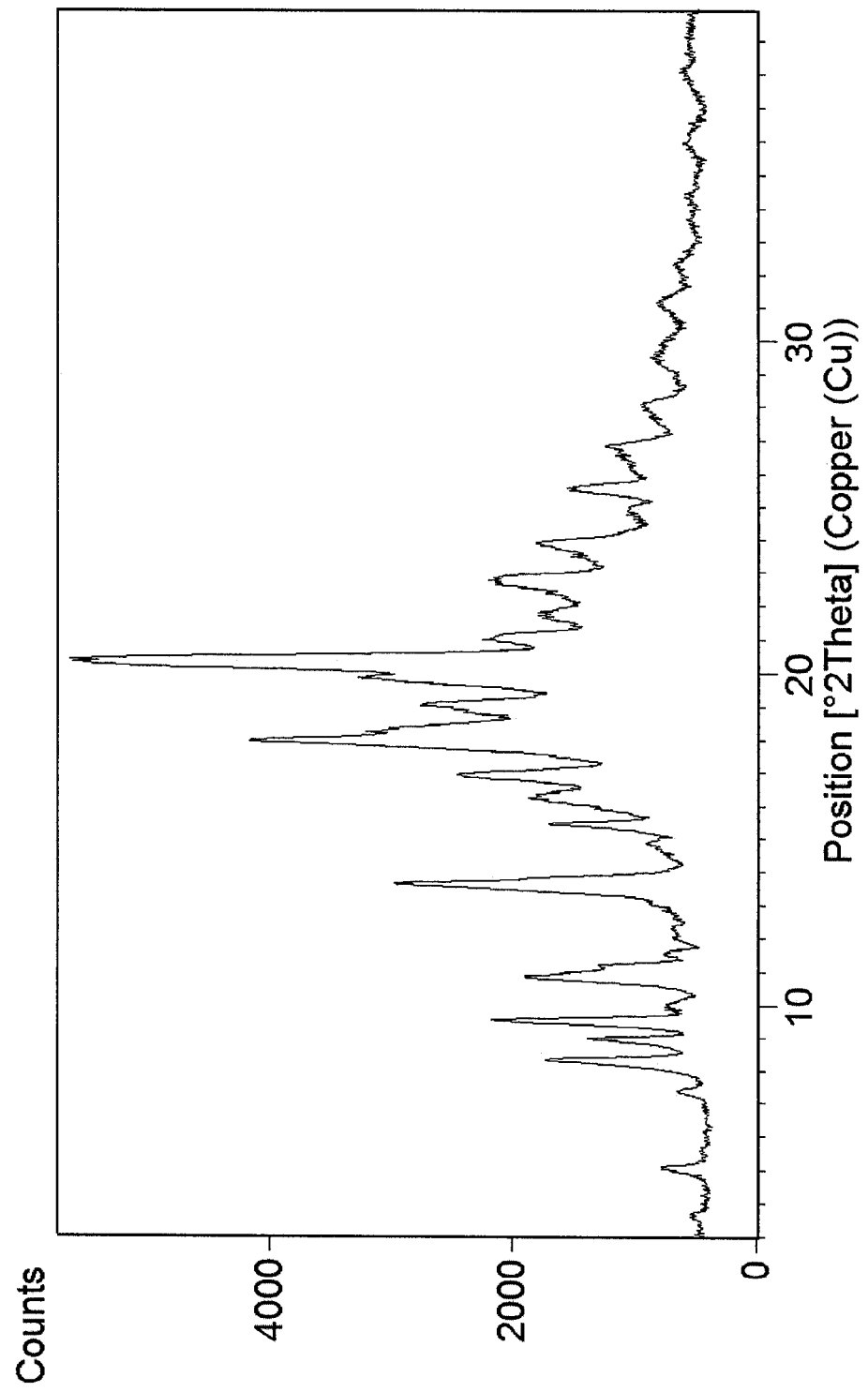
FIG. 13 is an XRPD pattern of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt.

The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt according to the invention has the characteristic XRPD pattern as shown in FIG. 13. XRPD pattern was recorded on an X-Ray Powder Diffractometer (X'PERT PRO MPD PANalytical). The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt exhibits the following diffraction peaks in XRPD pattern, see Table 3, below:

TABLE 3

| Pos. [°2Th.] | d [Å] | Rel. Int. [%] |
|---|---|---|
| 5.04 | 17.525 | 10.3 |
| 7.34 | 12.036 | 6.6 |
| 8.27 | 10.689 | 33.7 |
| 8.93 | 9.891 | 23.7 |
| 9.50 | 9.304 | 45.9 |
| 10.85 | 8.148 | 37.3 |
| 13.58 | 6.514 | 54.8 |
| 15.43 | 5.738 | 24.0 |
| 16.23 | 5.457 | 20.8 |
| 16.89 | 5.244 | 35.1 |
| 17.91 | 4.948 | 71.2 |
| 18.99 | 4.668 | 34.4 |
| 19.81 | 4.477 | 44.1 |
| 20.41 | 4.347 | 100.0 |
| 21.02 | 4.223 | 23.2 |
| 21.74 | 4.085 | 12.8 |
| 22.62 | 3.929 | 25.0 |
| 23.85 | 3.728 | 21.1 |
| 25.57 | 3.482 | 15.2 |
| 26.82 | 3.321 | 10.4 |
| 28.00 | 3.184 | 4.6 |

Figure 14:
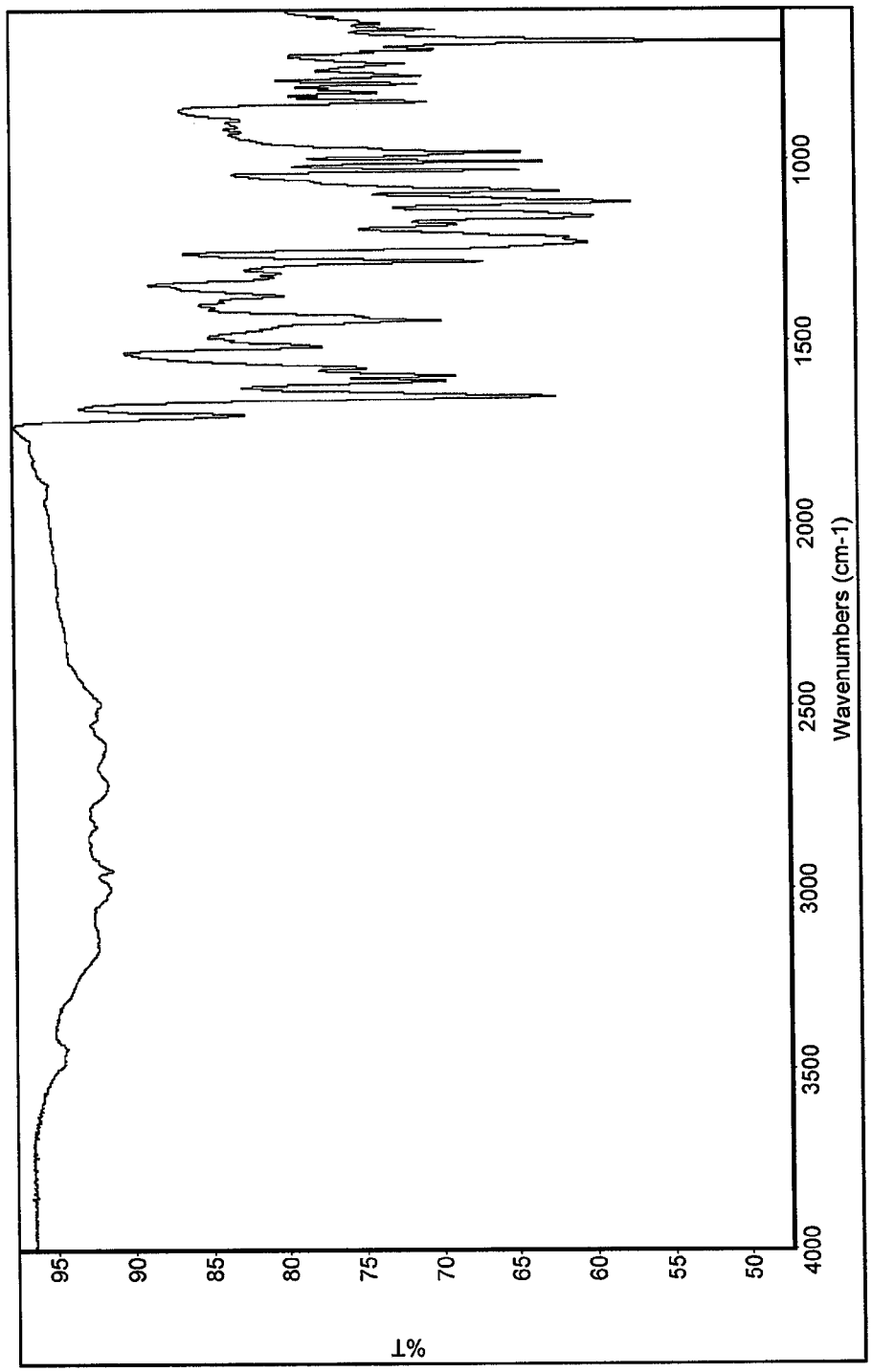
FIG. 14 is an FTIR spectrum of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt.
Figure 15:
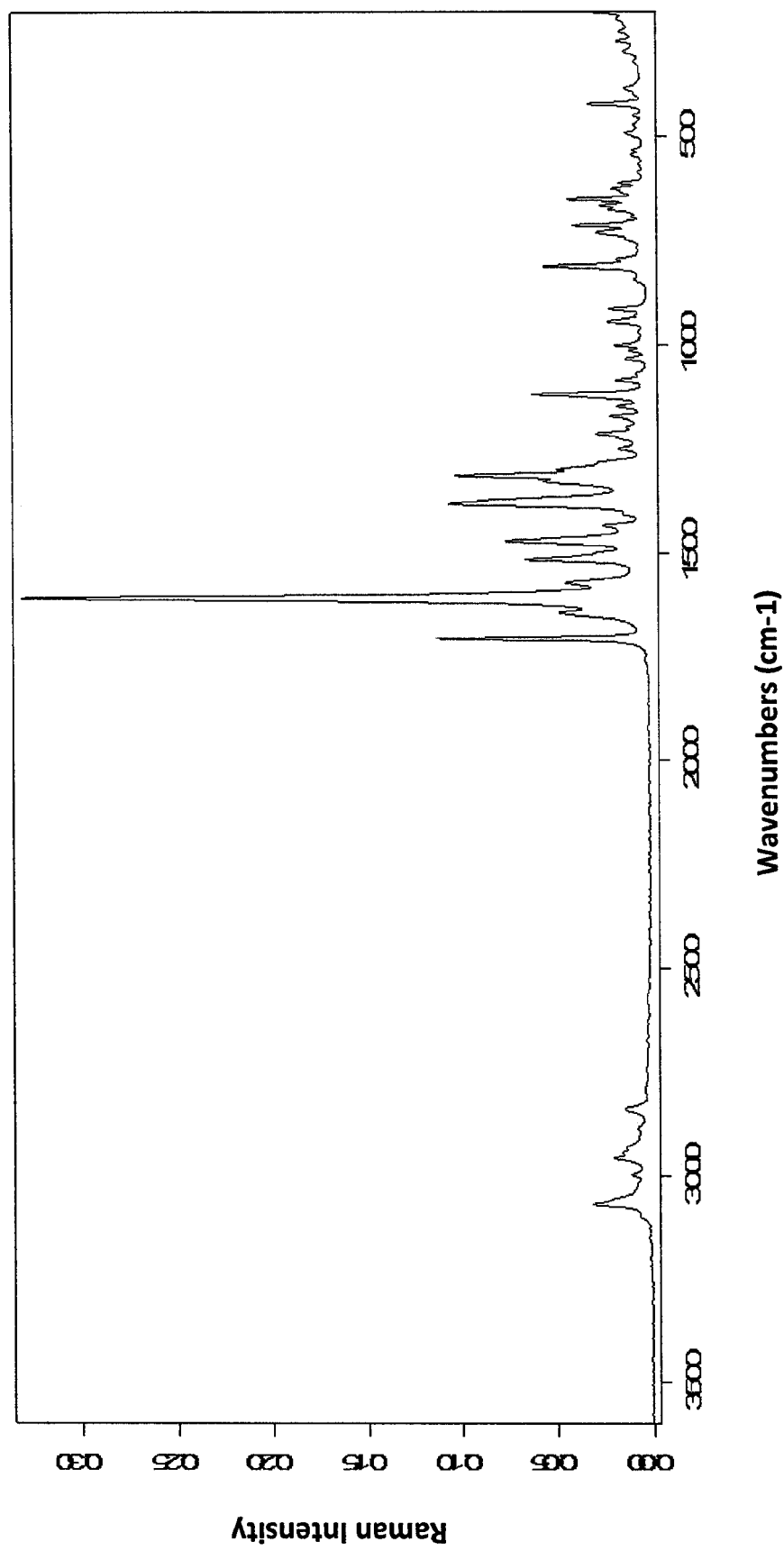
FIG. 15 is a Raman spectrum of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt.

The Crystal form 1 of methyl (3Z)-3-{[(4-{methyl[(4-methylpiperazin-1-yl)acetyl]amino}phenyl)-amino](phenyl)methylidene}-2-oxo-2,3-dihydro-1H-indole-6-carboxylate p-toluenesulfonic acid salt can be characterized by FTIR and Raman spectroscopy. FIG. 14 shows the FTIR spectrum (Nicolet Thermo 6700c) comprising characteristic peaks at 3444, 3006, 2952, 2832, 2494, 1702, 1650, 1444, 1118 and 681 cm$^{-1}$ wavenumbers. The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt is characterised by a Raman spectrum (Bruker RFS 100/S) comprising characteristic peaks at 3070, 2999, 2957, 2838, 1706, 1609, 1384, 1316, 1121 and 813 cm$^{-1}$ wavenumbers, shown in FIG. 15.

Figure 16:
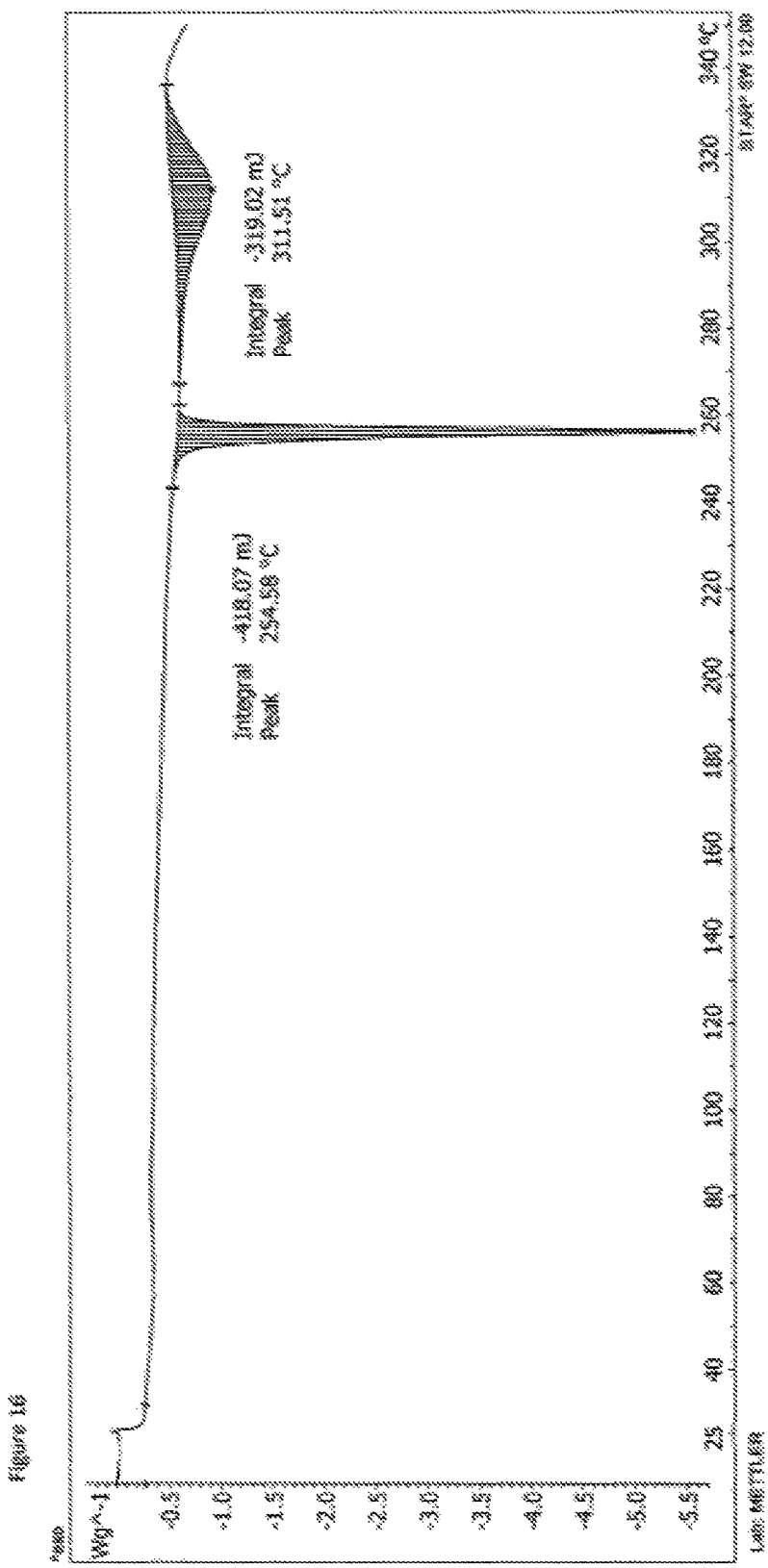
FIG. 16 is a DSC curve of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt.
Figure 17:
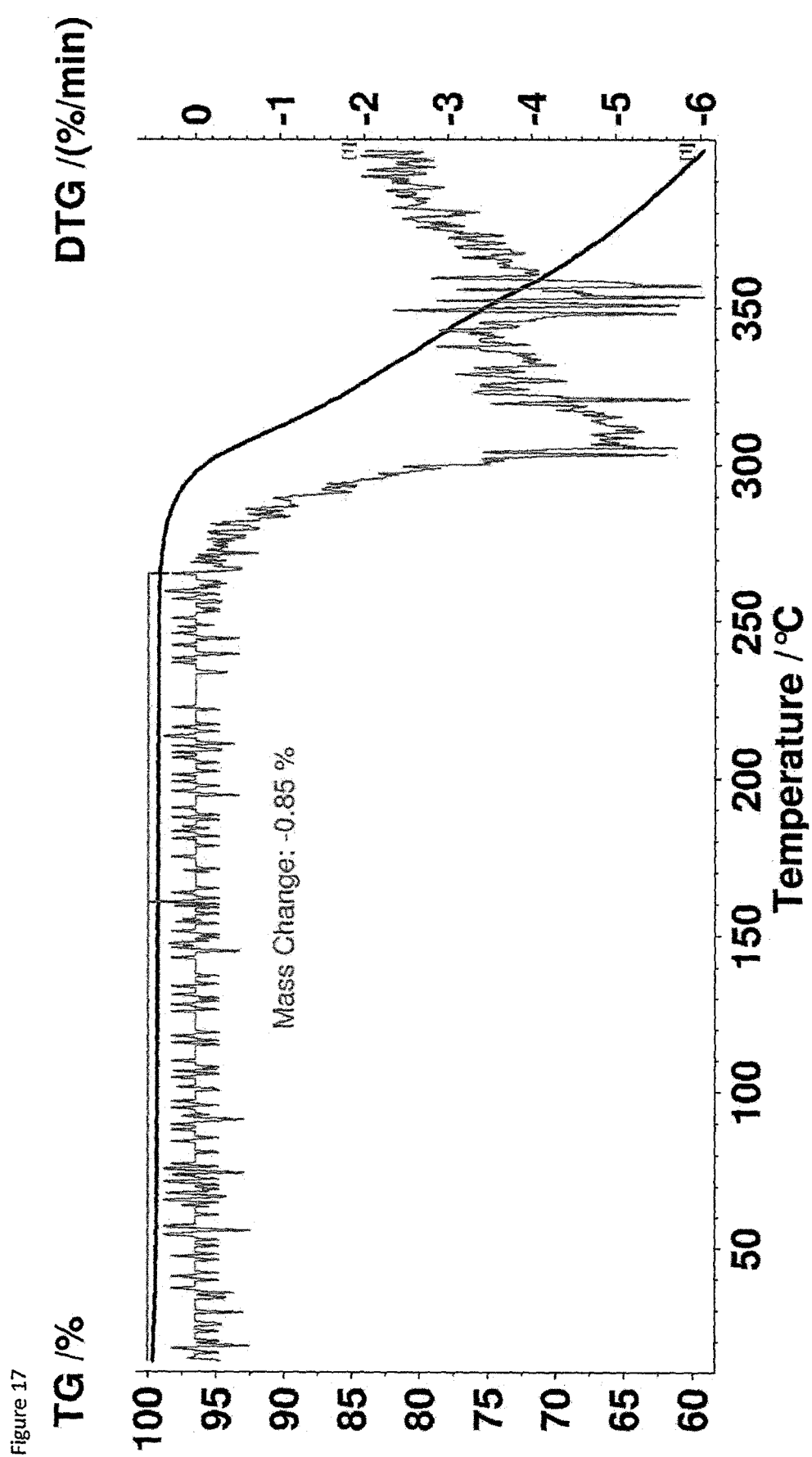
FIG. 17 is a TGA curve of the Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt.

The Crystal form 1 of methyl (3Z)-3-{[(4-{methyl[(4-methylpiperazin-1-yl)acetyl]amino}phenyl)amino]-(phenyl)methylidene}-2-oxo-2,3-dihydro-1H-indole-6-carboxylate p-toluenesulfonic acid salt can be further described by thermal analytical methods. FIG. 16 shows the DSC (Mettler-Toledo 822e DSC) and FIG. 17 shows the TGA (NETZSCH TG 209 thermogravimetric analyser) curves measured in the range of 25° C. to 350° C. and 25° C. to 400° C. The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt shows a 0.85% weight loss in the range of 25° C. to 265° C. The DSC measurement gives a melting process with $T_{peak}$=254.6° C.

In one of the objects of the invention, process for preparation of the Crystal modification 1 is provided. In this process, intedanib free base is suspended in a suitable organic solvent and heated to a temperature 50° C. The p-toluenesulfonic acid is added to the solution. The suitable organic solvent is preferably a polar aprotic solvent is selected from the group consisting of methyl-acetate, ethyl-acetate, butyl-acetate, acetonitrile, acetone, methyl ethyl ketone or a mixture thereof, more preferably the suitable polar protic solvent is methyl ethyl ketone, even more preferably it is methyl ethyl ketone at the temperature of 50° C.

The process of preparation of the Crystal modification 1 of intedanib p-toluenesulfonic acid salt thus comprises the following steps:

a/ suspending intedanib free base in a suitable organic solvent at 50° C.;
b/ drop-wise addition of the p-toluenesulfonic solution in a suitable organic solvent inducing dissolution followed by precipitation;
c/ stirring the suspension of step b/ at 50° C. for additional 1 hour;
d/ cooling the suspension of step c/ to a temperature of 0-5° C.;
e/ keeping the suspension of step d/ for 16 hours at a temperature of 0-5° C.;
f/ isolating the intedanib p-toluenesulfonic acid salt in Crystal form 1;
g/ optionally, drying the product of step f/ under the laboratory conditions until the constant weight of the product is reached.

The suitable organic solvent is preferably a polar aprotic solvent is selected from the group consisting of methyl-acetate, ethyl-acetate, butyl-acetate, acetonitrile, acetone, methyl ethyl ketone or a mixture thereof, more preferably the suitable polar protic solvent is methyl ethyl ketone, even more preferably it is methyl ethyl ketone at the temperature of 50° C.

Figure 19:
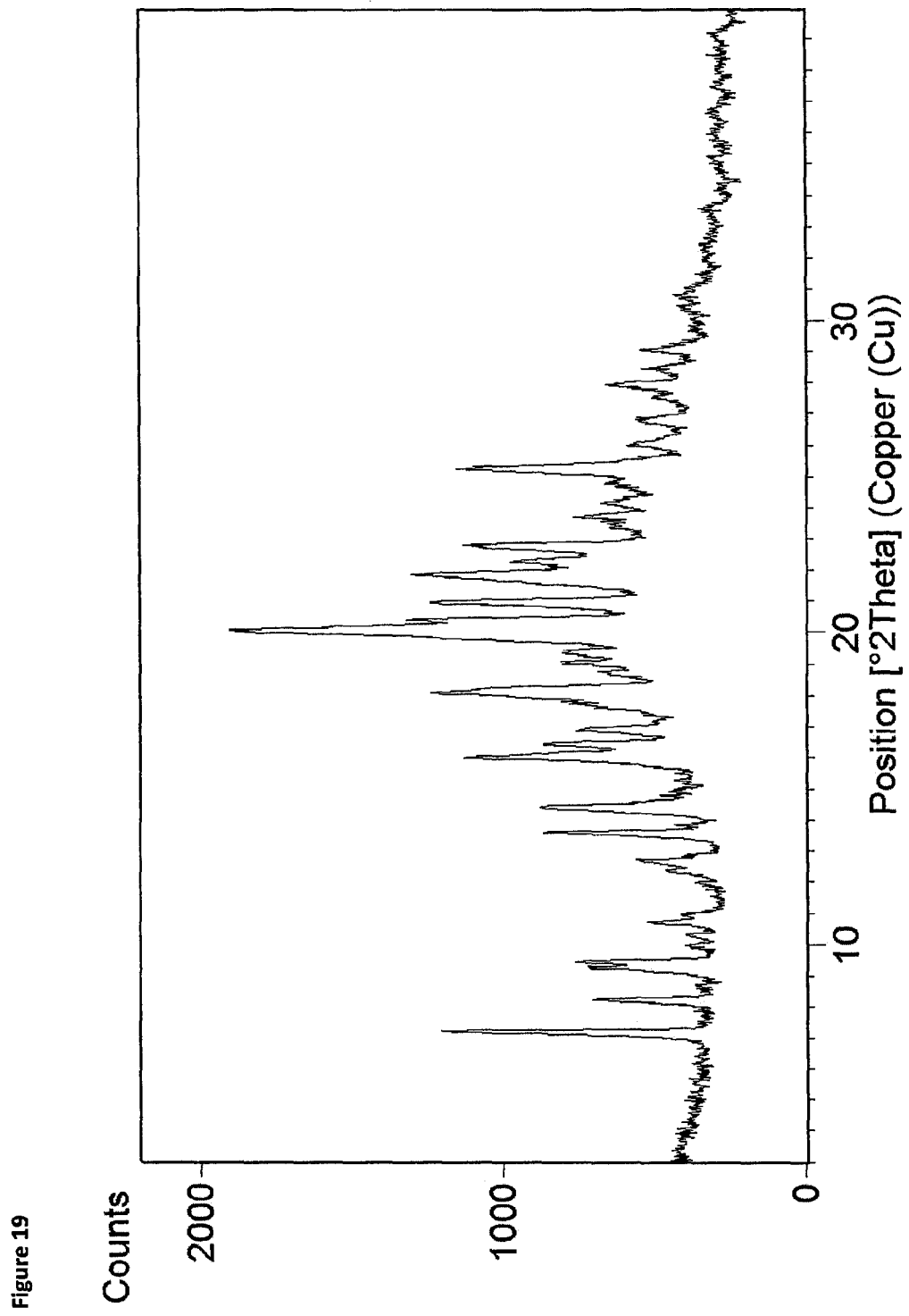
FIG. 19 is an XRPD pattern of the Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt.

The Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenenesulfonic acid salt according to the invention has the characteristic XRPD pattern as shown in FIG. 19. XRPD pattern was recorded on an X-Ray Powder Diffractometer (X'PERT PRO MPD PANalytical). The Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenenesulfonic acid salt exhibits the following diffraction peaks in XRPD pattern, see Table 4, below:

TABLE 4

| Pos. [°2Th.] | d [Å] | Rel. Int. [%] |
| --- | --- | --- |
| 7.16 | 12.331 | 65.5 |
| 8.22 | 10.751 | 28.9 |
| 9.25 | 9.550 | 30.8 |
| 9.45 | 9.351 | 32.3 |
| 10.71 | 8.251 | 16.9 |
| 12.65 | 6.992 | 19.0 |
| 13.56 | 6.523 | 42.8 |
| 14.39 | 6.152 | 41.0 |
| 16.01 | 5.533 | 58.2 |

TABLE 4-continued

| Pos. [°2Th.] | d [Å] | Rel. Int. [%] |
| --- | --- | --- |
| 16.42 | 5.396 | 31.4 |
| 16.88 | 5.248 | 24.2 |
| 18.04 | 4.914 | 52.8 |
| 19.01 | 4.666 | 16.2 |
| 19.33 | 4.589 | 11.5 |
| 20.03 | 4.429 | 100.0 |
| 20.92 | 4.243 | 49.8 |
| 21.78 | 4.077 | 55.6 |
| 22.26 | 3.990 | 27.8 |
| 22.74 | 3.908 | 51.8 |
| 23.71 | 3.750 | 19.2 |
| 25.23 | 3.527 | 52.5 |
| 26.01 | 3.424 | 10.7 |
| 26.75 | 3.330 | 9.7 |
| 27.89 | 3.196 | 18.7 |

Figure 20:
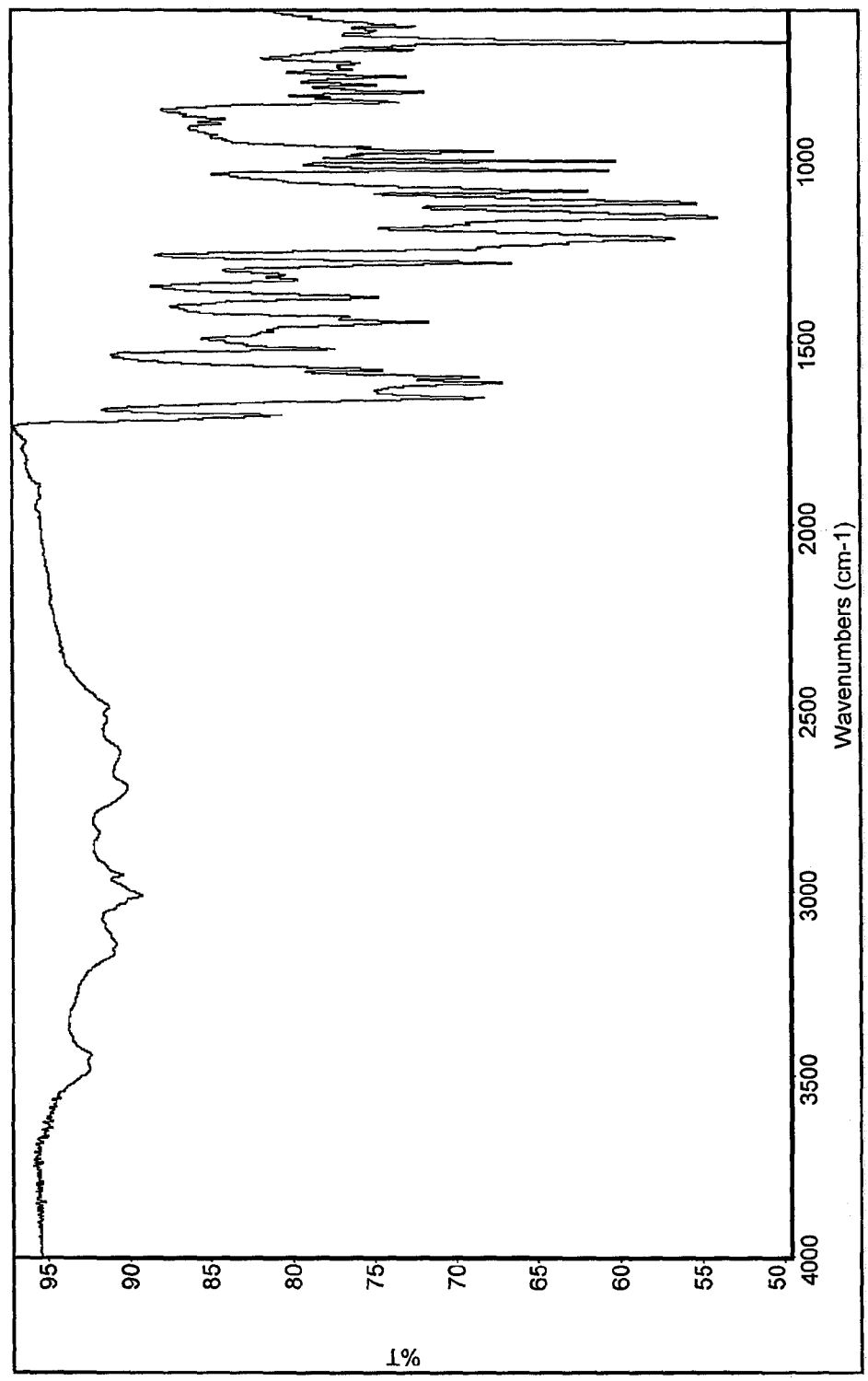
FIG. 20 is an FTIR spectrum of the Crystal modification 2 of methyl (3Z)-3-{[(4-{methyl[(4-methylpiperazin-1-yl)

The Crystal form 2 of methyl (3Z)-3-{[(4-{methyl[(4-methylpiperazin-1-yl)acetyl]amino}phenyl)-amino](phenyl)methylidene}-2-oxo-2,3-dihydro-1H-indole-6-carboxylate p-toluenenesulfonic acid salt can be characterized by FTIR and Raman spectroscopy. FIG. 20 shows the FTIR spectrum (Nicolet Thermo 6700c) comprising characteristic peaks at 3446, 3010, 2954, 2711, 2495, 1699, 1217, 1158, 1031 and 681 cm$^{-1}$ wavenumbers. The Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenenesulfonic acid salt is characterised by a Raman spectrum (Bruker RFS 100/S) comprising characteristic peaks at 3063, 2958, 2923, 2888, 2845, 1705, 1617, 1314, 808 and 291 cm$^1$ wavenumbers, shown in FIG. 21.

The Crystal form 2 of methyl (3Z)-3-{[(4-{methyl[(4-methylpiperazin-1-yl)acetyl]amino}phenyl)amino]-(phenyl)methylidene}-2-oxo-2,3-dihydro-1H-indole-6-carboxylate p-toluenenesulfonic acid salt can be further described by thermal analytical methods. FIG. 22 shows the DSC (Mettler-Toledo 822e DSC) and FIG. 23 shows the TGA (NETZSCH TG 209 thermogravimetric analyser) curves measured in the range of 25° C. to 350° C. and 25° C. to 400° C. The Crystal modification 2 of methyl (3Z)-3-{[(4-{methyl[(4-methylpiperazin-1-yl)acetyl]amino}phenyl)amino](phenyl) methylidene}-2-oxo-2,3-dihydro-1H-indole-6-carboxylate p-toluenenesulfonic acid salt shows a 1.5% weight loss in the range of 25° C. to 68° C. The DSC measurement gives a melting process with $T_{desolvation}$=77.7° C. and $T_{peak}$=236.9° C.

In one of the objects of the invention, process for preparation of the Crystal modification 2 is provided. In this process, intedanib free base is suspended in a suitable organic solvent and heated to a temperature 50° C. The p-toluenesulfonic acid is added to the solution. The suitable organic solvent is preferably a polar protic solvent selected from the group consisting of: methanol, ethanol, 1-propanol, 2-propanol, 1-butanol, 2-butanol or a mixture thereof, more preferably in methanol, even more preferably ethanol at the temperature of 50° C.

The process of preparation of the Crystal modification 2 of intedanib p-toluenesulfonic acid salt thus comprises the following steps:

a/ suspending intedanib free base in a suitable organic solvent at 50° C.;
b/ drop-wise addition of the p-toluenesulfonic solution in a suitable organic solvent inducing dissolution followed by precipitation;

c/ stirring the suspension of step b/ at 50° C. for additional 1 hour;
d/ cooling the suspension of step c/ to a temperature of 0-5° C.;
e/ keeping the suspension of step d/ for 16 hours at a temperature of 0-5° C.;
f/ isolating the intedanib p-toluenesulfonic acid salt in Crystal form 2;
g/ optionally, drying the product of step f/ under the laboratory conditions until the constant weight of the product is reached.

The suitable organic solvent is preferably a polar protic solvent selected from the group consisting of methanol, ethanol, 1-propanol, 2-propanol, 1-butanol, 2-butanol or a mixture thereof, more preferably methanol or ethanol, even more preferably ethanol at the temperature of 50° C.

Another process for the preparation of Crystal modification 2 of intedanib p-toluenesulfonic acid salt comprises the following steps:
a/ suspending intedanib p-toluenesulfonic acid salt in ethanol at room temperature;
b/ stirring the suspension of step a/ at room temperature for 72 hours;
c/ isolating the Crystal modification 2 of intedanib p-toluenesulfonic acid salt;
d/ optionally, drying the product of step c/ under the laboratory conditions until the constant weight of the product is reached.

The Crystal modification 1 of methyl (3Z)-3-{[(4-{methyl[(4-methylpiperazin-1-yl)acetyl]amino}-phenyl)amino](phenyl)methylidene}-2-oxo-2,3-dihydro-1H-indole-6-carboxylate L-tartaric acid acid salt according to the invention has the characteristic XRPD pattern as shown in FIG. 25. XRPD pattern was recorded on an X-Ray Powder Diffractometer (X'PERT PRO MPD PANalytical). The Crystal modification 1 of methyl (3Z)-3-{[(4-{methyl[(4-methylpiperazin-1-yl)acetyl]amino}phenyl)amino]-(phenyl)methylidene}-2-oxo-2,3-dihydro-1H-indole-6-carboxylate L-tartaric acid salt exhibits the following diffraction peaks in XRPD pattern, see Table 5, below:

TABLE 5

| Pos. [°2Th.] | d [Å] | Rel. Int. [%] |
| --- | --- | --- |
| 5.94 | 14.857 | 21.2 |
| 7.43 | 11.896 | 16.0 |
| 9.51 | 9.289 | 58.0 |
| 11.89 | 7.440 | 12.1 |
| 13.27 | 6.666 | 5.6 |
| 13.70 | 6.457 | 32.7 |
| 14.01 | 6.317 | 58.6 |
| 14.85 | 5.962 | 24.8 |
| 16.02 | 5.529 | 6.9 |
| 17.85 | 4.964 | 45.2 |
| 19.08 | 4.648 | 54.0 |
| 19.47 | 4.556 | 96.8 |
| 20.00 | 4.436 | 100.0 |
| 20.62 | 4.304 | 31.0 |
| 22.00 | 4.037 | 34.9 |
| 23.20 | 3.831 | 23.9 |
| 23.94 | 3.714 | 21.9 |
| 27.83 | 3.203 | 4.6 |
| 29.53 | 3.022 | 8.1 |
| 30.53 | 2.926 | 3.8 |
| 31.30 | 2.856 | 6.8 |
| 33.03 | 2.710 | 3.5 |
| 36.01 | 2.492 | 3.7 |

The Crystal form 1 of methyl (3Z)-3-{[(4-{methyl[(4-methylpiperazin-1-yl)acetyl]amino}phenyl)-amino](phenyl)methylidene}-2-oxo-2,3-dihydro-1H-indole-6-carboxylate L-tartaric acid salt can be characterized by FTIR and Raman spectroscopy. FIG. 26 shows the FTIR spectrum (Nicolet Thermo 6700c) comprising characteristic peaks at 3064, 3000, 2952, 2840, 1706, 1610, 1378, 1312, 1117 and 809 cm-1 wavenumbers. The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate L-tartaric acid acid salt is characterised by a Raman spectrum (Bruker RFS 100/S) comprising characteristic peaks at 3065, 3000, 2952, 2840, 1706, 1610, 1378, 1312, 1117 and 809 cm$^{-1}$ wavenumbers, shown in FIG. 27.

The Crystal form 1 of methyl (3Z)-3-{[(4-{methyl[(4-methylpiperazin-1-yl)acetyl]amino}phenyl)-amino](phenyl)methylidene}-2-oxo-2,3-dihydro-1H-indole-6-carboxylate L-tartaric acid salt can be further described by thermal analytical methods. FIG. 28 shows the DSC (Mettler-Toledo 822e DSC) and FIG. 29 shows the TGA (NETZSCH TG 209 thermogravimetric analyser) curves measured in the range of 25° C. to 350° C. and 25° C. to 400° C. The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate L-tartaric acid salt shows a 1.69% weight loss in the range of 25° C. to 57° C. The DSC measurement gives a melting process with $T_{desolvation}$=58.5° C. and $T_{peak}$=253.8° C.

In one of the objects of the invention, process for preparation of the Crystal modification 1 is provided. In this process, intedanib free base is suspended in a suitable organic solvent and heated to a temperature 50° C. The L-tartaric acid is added to the solution. The suitable organic solvent is preferably a polar aprotic solvent, more preferably the polar aprotic solvent is selected from the group consisting of: methyl-acetate, ethyl-acetate, butyl-acetate, acetonitrile, acetone, methyl ethyl ketone or a mixture thereof, even more preferably the suitable organic solvent is ethyl acetate and even more preferably the suitable organic solvent is methyl ethyl ketone at the temperature of 50° C.

The process of preparation of the Crystal modification 1 of intedanib L-tartaric acid salt thus comprises the following steps:
a/ suspending intedanib free base in a suitable organic solvent at 50° C.;
b/ drop-wise addition of the L-tartaric acid solution in a suitable organic solvent inducing dissolution followed by precipitation;
c/ stirring the suspension of step b/ at 50° C. for additional 1 hour;
d/ cooling the suspension of step c/ to a temperature of 0-5° C.;
e/ keeping the suspension of step d/ for 16 hours at a temperature of 0-5° C.;
f/ isolating the intedanib L-tartaric acid salt in Crystal form 1;
g/ optionally, drying the product of step f/ under the laboratory conditions until the constant weight of the product is reached.

The suitable organic solvent is preferably a polar aprotic solvent, more preferably the polar aprotic solvent is selected from the group consisting of methyl-acetate, ethyl-acetate, butyl-acetate, acetonitrile, acetone, methyl ethyl ketone or a mixture thereof, more preferably the suitable organic solvent is ethyl acetate or methyl ethyl ketone, even more preferably the suitable organic solvent is methyl ethyl ketone at the temperature of 50° C.

Another process for the preparation of Crystal modification 1 of intedanib L-tartaric acid salt comprises the following steps:

a/ suspending intedanib L-tartaric acid salt in methyl ethyl ketone at room temperature;
b/ stirring the suspension of step a/ at room temperature for 72 hours;
c/ isolating the Crystal modification 1 of intedanib L-tartaric acid salt;
d/ optionally, drying the product of step c/ under the laboratory conditions until the constant weight of the product is reached.

The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate maleic acid salt according to the invention has the characteristic XRPD pattern as shown in FIG. 31. XRPD pattern was recorded on an X-Ray Powder Diffractometer (X'PERT PRO MPD PANalytical). The Crystal modification 1 of methyl (3Z)-3-{[(4-{methyl[(4-methylpiperazin-1-yl)acetyl]amino}phenyl)-amino](phenyl)methylidene}-2-oxo-2,3-dihydro-1H-indole-6-carboxylate maleic acid salt exhibits the following diffraction peaks in XRPD pattern, see Table 6, below:

TABLE 6

| Pos. [°2Th.] | d [Å] | Rel. Int. [%] |
| --- | --- | --- |
| 5.38 | 16.409 | 17.5 |
| 9.16 | 9.649 | 7.1 |
| 10.70 | 8.260 | 23.3 |
| 10.94 | 8.079 | 26.4 |
| 11.92 | 7.419 | 8.3 |
| 12.37 | 7.149 | 15.1 |
| 12.64 | 6.996 | 31.1 |
| 13.55 | 6.531 | 10.2 |
| 14.04 | 6.302 | 9.1 |
| 15.13 | 5.852 | 6.9 |
| 15.63 | 5.664 | 9.7 |
| 16.44 | 5.389 | 57.9 |
| 17.49 | 5.068 | 18.2 |
| 17.78 | 4.985 | 52.3 |
| 18.55 | 4.780 | 16.4 |
| 19.10 | 4.644 | 34.1 |
| 19.45 | 4.560 | 100.0 |
| 19.94 | 4.450 | 36.9 |
| 21.43 | 4.143 | 34.0 |
| 21.81 | 4.072 | 19.1 |
| 23.70 | 3.752 | 17.1 |
| 24.24 | 3.669 | 10.8 |
| 25.01 | 3.557 | 24.1 |
| 26.22 | 3.397 | 9.3 |
| 27.40 | 3.253 | 14.1 |
| 27.84 | 3.202 | 10.6 |
| 28.49 | 3.131 | 6.8 |
| 29.06 | 3.070 | 6.6 |
| 30.18 | 2.959 | 13.3 |
| 30.99 | 2.883 | 8.4 |

The Crystal form 1 of methyl (3Z)-3-{[(4-{methyl[(4-methylpiperazin-1-yl)acetyl]amino}phenyl)-amino](phenyl)methylidene}-2-oxo-2,3-dihydro-1H-indole-6-carboxylate maleic acid salt can be characterized by FTIR and Raman spectroscopy. FIG. 32 shows the FTIR spectrum (Nicolet Thermo 6700c) comprising characteristic peaks at 3171, 3026, 2951, 2823, 2478, 1706, 1653, 1222, 985 and 648 cm$^{-1}$ wavenumbers. The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate maleic acid salt is characterised by a Raman spectrum (Bruker RFS 100/S) comprising characteristic peaks at 3065, 3032, 3009, 2969, 2952, 1706, 1612, 1378, 1312 and 811 cm$^{-1}$ wavenumbers, shown in FIG. 33.

The Crystal form 1 of methyl (3Z)-3-{[(4-{methyl[(4-methylpiperazin-1-yl)acetyl]amino}phenyl)amino]-(phenyl)methylidene}-2-oxo-2,3-dihydro-1H-indole-6-carboxylate maleic acid salt can be further described by thermal analytical methods. FIG. 34 shows the DSC (Mettler-Toledo 822e DSC) and FIG. 35 shows the TGA (NETZSCH TG 209 thermogravimetric analyser) curves measured in the range of 25° C. to 350° C. and 25° C. to 400° C. The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate maleic acid salt shows a 1.17% weight loss in the range of 25° C. to 190° C. and 1% weight loss in the range of 190° C. to 221° C. The DSC measurement gives a melting process with $T_{desolvation}$=216.5° C. and $T_{peak}$=232.5° C.

In one of the objects of the invention, process for preparation of the Crystal modification 1 is provided. In this process, intedanib free base is suspended in a suitable organic solvent and heated to a temperature 50° C. The maleic acid is added to the solution. The suitable organic solvent is preferably a polar aprotic solvent, more preferably the polar aprotic solvent is selected from the group consisting of: methyl-acetate, ethyl-acetate, butyl-acetate, acetonitrile, acetone, methyl ethyl ketone or a mixture thereof, even more preferably the suitable organic solvent is ethyl acetate and even more preferably the suitable organic solvent is ethyl acetate at the temperature of 50° C.

The Crystal form 1 of intedanib maleic acid salt can be prepared by a process comprising the following steps:

a/ suspending of intedanib free base in a suitable organic solvent at 50° C.;
b/ drop-wise addition of the solution of maleic acid in a suitable organic solvent;
c/ stirring the solution of step b/ at 50° C. for additional 1 hour while precipitation occurred;
d/ cooling the suspension of step c/ to room temperature;
e/ keeping the suspension of step d/ for 16 hours at room temperature;
f/ isolating the intedanib maleic acid salt in Crystal form 1;
g/ optionally, drying the product of step f/ under the laboratory conditions until the constant weight of the product is reached.

The suitable organic solvent is preferably a polar aprotic solvent, more preferably the polar aprotic solvent is selected from the group consisting of: methyl-acetate, ethyl-acetate, butyl-acetate, acetonitrile, acetone, methyl ethyl ketone or a mixture thereof, more preferably the suitable organic solvent is ethyl acetate and even more preferably the suitable organic solvent is ethyl acetate at the temperature of 50° C.

The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate acetic acid salt according to the invention has the characteristic XRPD pattern as shown in FIG. 37. XRPD pattern was recorded on an X-Ray Powder Diffractometer (X'PERT PRO MPD PANalytical). The Crystal modification 1 of methyl (3Z)-3-{[(4-{methyl[(4-methylpiperazin-1-yl)acetyl]amino}phenyl)-amino](phenyl)methylidene}-2-oxo-2,3-dihydro-1H-indole-6-carboxylate acetic acid salt exhibits the following diffraction peaks in XRPD pattern, see Table 7, below:

TABLE 7

| Pos. [°2Th.] | d [Å] | Rel. Int. [%] |
|---|---|---|
| 6.58 | 13.418 | 26.9 |
| 7.51 | 11.762 | 6.1 |
| 9.39 | 9.415 | 47.0 |
| 9.82 | 9.002 | 9.4 |
| 13.32 | 6.644 | 8.9 |
| 14.41 | 6.140 | 22.3 |
| 15.31 | 5.783 | 39.6 |
| 15.94 | 5.555 | 7.8 |
| 17.41 | 5.090 | 10.1 |
| 17.78 | 4.984 | 28.7 |
| 18.60 | 4.768 | 18.5 |
| 18.71 | 4.739 | 40.2 |
| 18.87 | 4.699 | 32.6 |
| 19.01 | 4.666 | 52.9 |
| 19.16 | 4.628 | 33.2 |
| 19.75 | 4.492 | 19.9 |
| 20.66 | 4.295 | 100.0 |
| 21.78 | 4.078 | 43.1 |
| 23.24 | 3.824 | 22.9 |
| 23.51 | 3.781 | 13.7 |
| 23.88 | 3.724 | 12.9 |
| 24.84 | 3.581 | 19.4 |
| 26.60 | 3.349 | 5.3 |
| 26.83 | 3.320 | 4.9 |
| 27.92 | 3.193 | 4.1 |
| 28.60 | 3.119 | 23.7 |
| 29.05 | 3.072 | 8.7 |
| 29.61 | 3.015 | 7.6 |
| 31.02 | 2.881 | 5.9 |
| 31.62 | 2.828 | 9.2 |
| 32.89 | 2.721 | 2.8 |
| 35.52 | 2.525 | 4.4 |
| 35.67 | 2.515 | 6.3 |
| 35.99 | 2.493 | 5.3 |
| 36.10 | 2.486 | 5.3 |

The Crystal form 1 of methyl (3Z)-3-{[(4-{methyl[(4-methylpiperazin-1-yl)acetyl]amino}phenyl)-amino](phenyl)methylidene}-2-oxo-2,3-dihydro-1H-indole-6-carboxylate acetic acid salt can be characterized by FTIR and Raman spectroscopy. FIG. 38 shows the FTIR spectrum (Nicolet Thermo 6700c) comprising characteristic peaks at 3059, 2988, 2955, 2814, 1713, 1281, 1098, 992, 786 and 644 cm$^1$ wavenumbers. The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate acetic acid salt is characterised by a Raman spectrum (Bruker RFS 100/S) comprising characteristic peaks at 3063, 3023, 2958, 2936, 2924, 1720, 1611, 1472, 1318 and 810 cm$^{-1}$ wavenumbers, shown in FIG. 39.

The Crystal form 1 of methyl (3Z)-3-{[(4-{methyl[(4-methylpiperazin-1-yl)acetyl]amino}phenyl)amino]-(phenyl)methylidene}-2-oxo-2,3-dihydro-1H-indole-6-carboxylate acetic acid salt can be further described by thermal analytical methods. FIG. 40 shows the DSC (Mettler-Toledo 822e DSC) and FIG. 41 shows the TGA (NETZSCH TG 209 thermogravimetric analyser) curves measured in the range of 25° C. to 350° C. and 25° C. to 400° C. The Crystal modification 1 of methyl (3Z)-3-{[(4-{methyl[(4-methyl-piperazin-1-yl)acetyl]amino}phenyl)amino](phenyl)methylidene}-2-oxo-2,3-dihydro-1H-indole-6-carboxylate acetic acid salt shows a 0.27% weight loss in the range of 25° C. to 100° C. and 5.6% weight loss in the range of 100° C. to 155° C., 3.2% weight loss in the range of 155° C. to 182° C. and 3.7% weight loss in the range of 182° C. to 248° C. The DSC measurement gives a melting process with $T_{desolvation1}=120.7°$ C., $T_{desolvation2}=146.6°$ C., $T_{peak1}=177.5°$ C. and $T_{peak2}=254.4°$ C.

In one of the objects of the invention, process for preparation of the Crystal modification 1 is provided. In this process, intedanib free base is suspended in a suitable organic solvent and heated to a temperature 50° C. The acetic acid is added to the solution. The suitable organic solvent is preferably a polar aprotic solvent selected from the group consisting of methyl-acetate, ethyl-acetate, butyl-acetate, acetonitrile, acetone, methyl ethyl ketone or a mixture thereof, more preferably the suitable polar aprotic solvent is methyl ethyl ketone, even more preferably it is methyl ethyl ketone at the temperature of 50° C.

The process of preparation of the Crystal modification 1 of intedanib acetic acid salt thus comprises the following steps:

a/ suspending intedanib free base in a suitable organic solvent at 50° C.;

b/ drop-wise addition of the acetic solution in a suitable organic solvent inducing dissolution followed by precipitation;

c/ stirring the suspension of step b/ at 50° C. for additional 1 hour;

d/ cooling the suspension of step c/ to a temperature of 0-5° C.;

e/ keeping the suspension of step d/ for 16 hours at a temperature of 0-5° C.;

f/ isolating the intedanib acetic acid salt in Crystal form 1;

g/ optionally, drying the product of step f/ under the laboratory conditions until the constant weight of the product is reached.

The suitable organic solvent is preferably a polar aprotic solvent is selected from the group consisting of methyl-acetate, ethyl-acetate, butyl-acetate, acetonitrile, acetone, methyl ethyl ketone or a mixture thereof, more preferably the suitable polar aprotic solvent is methyl ethyl ketone, even more preferably it is methyl ethyl ketone at the temperature of 50° C.

The Crystal modification 1 of methyl (3Z)-3-{[(4-{methyl[(4-methylpiperazin-1-yl)acetyl]amino}-phenyl)amino](phenyl)methylidene}-2-oxo-2,3-dihydro-1H-indole-6-carboxylate phosphoric acid salt according to the invention has the characteristic XRPD pattern as shown in FIG. 43. XRPD pattern was recorded on an X-Ray Powder Diffractometer (X'PERT PRO MPD PANalytical). The Crystal modification 1 of methyl (3Z)-3-{[(4-{methyl[(4-methylpiperazin-1-yl)acetyl]amino}phenyl)-amino](phenyl)methylidene}-2-oxo-2,3-dihydro-1H-indole-6-carboxylate phosphoric acid salt exhibits the following diffraction peaks in XRPD pattern, see Table 8, below:

TABLE 8

| Pos. [°2Th.] | d [Å] | Rel. Int. [%] |
|---|---|---|
| 5.55 | 15.919 | 47.2 |
| 8.06 | 10.955 | 31.6 |
| 10.60 | 8.338 | 9.3 |
| 11.18 | 7.905 | 100.0 |
| 11.60 | 7.624 | 22.5 |
| 13.99 | 6.324 | 15.5 |
| 14.71 | 6.018 | 12.3 |
| 15.72 | 5.634 | 19.0 |
| 15.97 | 5.546 | 17.2 |
| 16.24 | 5.454 | 29.4 |
| 16.83 | 5.263 | 25.1 |
| 17.93 | 4.944 | 21.5 |
| 19.46 | 4.557 | 39.8 |
| 21.58 | 4.114 | 22.9 |
| 22.30 | 3.984 | 63.1 |
| 23.30 | 3.815 | 21.5 |

TABLE 8-continued

| Pos. [°2Th.] | d [Å] | Rel. Int. [%] |
|---|---|---|
| 24.36 | 3.651 | 5.4 |
| 25.26 | 3.524 | 8.8 |
| 25.88 | 3.440 | 11.4 |
| 27.08 | 3.290 | 13.2 |
| 28.31 | 3.150 | 5.8 |
| 28.89 | 3.088 | 7.9 |
| 29.76 | 2.999 | 6.6 |
| 31.02 | 2.880 | 4.6 |
| 32.63 | 2.742 | 3.8 |

The Crystal form 1 of methyl (3Z)-3-{[(4-{methyl[(4-methylpiperazin-1-yl)acetyl]amino}phenyl)-amino](phenyl)methylidene}-2-oxo-2,3-dihydro-1H-indole-6-carboxylate phosphoric acid salt can be characterized by FTIR and Raman spectroscopy. FIG. 44 shows the FTIR spectrum (Nicolet Thermo 6700c) comprising characteristic peaks at 2974, 2725, 2328, 1710, 1683, 1568, 1292, 1226, 959 and 876 $cm^{-1}$ wavenumbers. The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate phosphoric acid salt is characterised by a Raman spectrum (Bruker RFS 100/S) comprising characteristic peaks at 3074, 3060, 2973, 2953, 1708, 1611, 1373, 1329, 811 and 675 $cm^{-1}$ wavenumbers, shown in FIG. 45.

The Crystal form 1 of methyl (3Z)-3-{[(4-{methyl[(4-methylpiperazin-1-yl)acetyl]amino}phenyl)amino]-(phenyl)methylidene}-2-oxo-2,3-dihydro-1H-indole-6-carboxylate phosphoric acid salt can be further described by thermal analytical methods. FIG. 46 shows the DSC (Mettler-Toledo 822e DSC) and FIG. 47 shows the TGA (NETZSCH TG 209 thermogravimetric analyser) curves measured in the range of 25° C. to 350° C. and 25° C. to 400° C. The Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate phosphoric acid salt shows a 2.85% weight loss in the range of 25° C. to 110° C. The DSC measurement gives a melting process with $T_{desolvation}$=140.1° C., $T_{peak1}$=247.6° C. and $T_{peak2}$=283.0° C.

In one of the objects of the invention, process for preparation of the Crystal modification 1 is provided. In this process, intedanib free base is suspended in a suitable organic solvent and heated to a temperature 50° C. The phosphoric acid is added to the solution. The suitable organic solvent is preferably a polar aprotic solvent, more preferably the polar aprotic solvent is selected from the group consisting of: methyl-acetate, ethyl-acetate, butyl-acetate, acetonitrile, acetone, methyl ethyl ketone or a mixture thereof, more preferably the suitable organic solvent is ethyl acetate and even more preferably the suitable organic solvent is ethyl acetate at the temperature of 50° C.

The Crystal form 1 of intedanib phosphoric acid salt can be prepared by a process comprising the following steps:

a/ suspending of intedanib free base in a suitable organic solvent at 50° C.;
b/ drop-wise addition of the solution of phosphoric acid in a suitable organic solvent;
c/ stirring the solution of step b/ at 50° C. for additional 1 hour while precipitation occurred;
d/ cooling the suspension of step c/ to room temperature;
e/ keeping the suspension of step d/ for 16 hours at room temperature;
f/ isolating the intedanib phosphoric acid salt in Crystal form 1;
g/ optionally, drying the product of step f/ under the laboratory conditions until the constant weight of the product is reached.

The suitable organic solvent is preferably a polar aprotic solvent, more preferably the polar aprotic solvent is selected from the group consisting of: methyl-acetate, ethyl-acetate, butyl-acetate, acetonitrile, acetone, methyl ethyl ketone or a mixture thereof, more preferably the suitable organic solvent is ethyl acetate and even more preferably the suitable organic solvent is ethyl acetate at the temperature of 50° C.

The term "room temperature" is defined as a temperature between 15° C. and 29° C. for the purpose of this document; preferably it is between 20-23° C.

The term "drying under the laboratory conditions", as used in this patent application, means drying at room temperature and relative humidity 20-60%.

Analysis—NMR (Nuclear Magnetic Resonance)

For $^1$H NMR spectrum the Bruker NMR spectrometer AVANCE 500 MHz and DMSO as solvent were used. The stoichiometry of salts was determined from integrals of corresponding signals of API and counterion.

In case of phosphates the stoichiometry was determined by means of an internal standard added to the measured sample. This standard was a compound containing in its molecule defined numbers of phosporus and hydrogen atoms. Signals of this compound were compared with those of intedanib phosphate both in $^1$H and $^{31}$P NMR spectrum.

Analysis—XRPD (X-Ray Powder Diffractometry)

Diffractograms were obtained with laboratory X'PERT PRO MPD PANalytical diffractometer, used radiation CuKα (λ=0.1542 nm (1.542 Å).

Generator Settings:
excitation voltage 45 kV
anodic current 40 mA.
Scan Description:
scan type—gonio
measurement range 2-40° 2θ
step size 0.01° 2θ
step time: 0.5 s.

Samples were measured as received on Si plate (zero background holder).

Incident beam optics: programmable divergence slits (irradiated length 10 mm). 10 mm mask. 1/4° anti-scatter fixed slit, 0.02 rad Soller slits.

Diffracted beam optics: X'Celerator detector, scanning mode, active length 2.122°. 0.02 rad Soller slits, anti-scatter slit 5.0 mm. Ni filter.

Analysis—FTIR (Fourier-Transformed Infra-Red) Spectroscopy

FTIR spectra were measured by Nicolet Thermo 6700 spectrometer.
General Settings:
Number of sample scans: 45
Number of background scans: 45
Resolution: 4.000
Sample gain: 4.0
Optical velocity: 0.6329
Aperture: 100.00

Analysis—Roman Spectroscopy

Raman spectrum were recorded by FT-Raman Bruker RFS 100/S Spectrometer
General Settings:
Excitation source: Nd-YAG laser (1064 nm)
Applied spectruml domain: 4000-200 $cm^{-1}$
Applied laser power: 250 mW Detector: liquid nitrogen cooled Ge-diode detector (D418-T)
Resolution: 4 cm$^{-1}$
Number of accumulations: 128
Scattering geometry: 180° (back scattering)
Aperture: 3.5 mm Analysis—DSC (Differential Scanning Calorimetry)

DSC measurements were performed using a Mettler-Toledo 822e DSC.

Samples were placed into standard aluminum pans (40 µL) sealed with a pierced lid. The sample cell was heated under a nitrogen purge at a rate of 10° C./min from 25° C. up to a final temperature of 300° C. with 50 mL/min nitrogen purge. The temperatures specified in relation to DSC analyses are the temperatures of the peak maxima ($T_{peak}$) and onset temperature ($T_{onset}$) of peaks for the crystalline modification. The enthalpy is given in J/g.

The weight of sample was about 2.5-3 mg.

Analysis—TGA (ThermoGravimetric Analysis)

TGA analyses were performed using a NETZSCH TG 209 thermogravimetric analyser (NETZSCH-Gerätebau GmbH, Germany).

Each sample was placed in an aluminum sample pan and inserted into the TG furnace. The furnace was heated under nitrogen purge at a rate of 10° C./min from 25° C. up to a final temperature of 300° C.

The weight of sample was about 5-15 mg.

EXAMPLES

The following examples are intended to further illustrate the present invention without limiting its scope.

Example 1

Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt 7000 mg (13 mmol) of intedanib free base was suspended in 80 mL of methanol and was heated to 60° C. The solution of 1247 mg Methanesulfonic acid (>98%) in 2 mL of water (13 mol) was added dropwise and a clear solution formed.

The solution was stirred at 60° C. for additional 1 hour and was cooled down slowly to 44° C. where it turned to opaque and was seeded. Then was further cooled to 0° C. where 40 mL of MTBE was added and the suspension was stirred at 0° C. for additional 2 hours.

The product was filtered through a G4 glass filter and was washed with 10 mL of MTBE.

Product: 7580 mg
Yield: 92%
HPLC: 99.8%

XRPD pattern was measured (FIG. 1) and showed that the compound is in a crystalline state that was designated as Crystal modification 1 of intedanib methanesulfonic acid salt.

Figure 6:
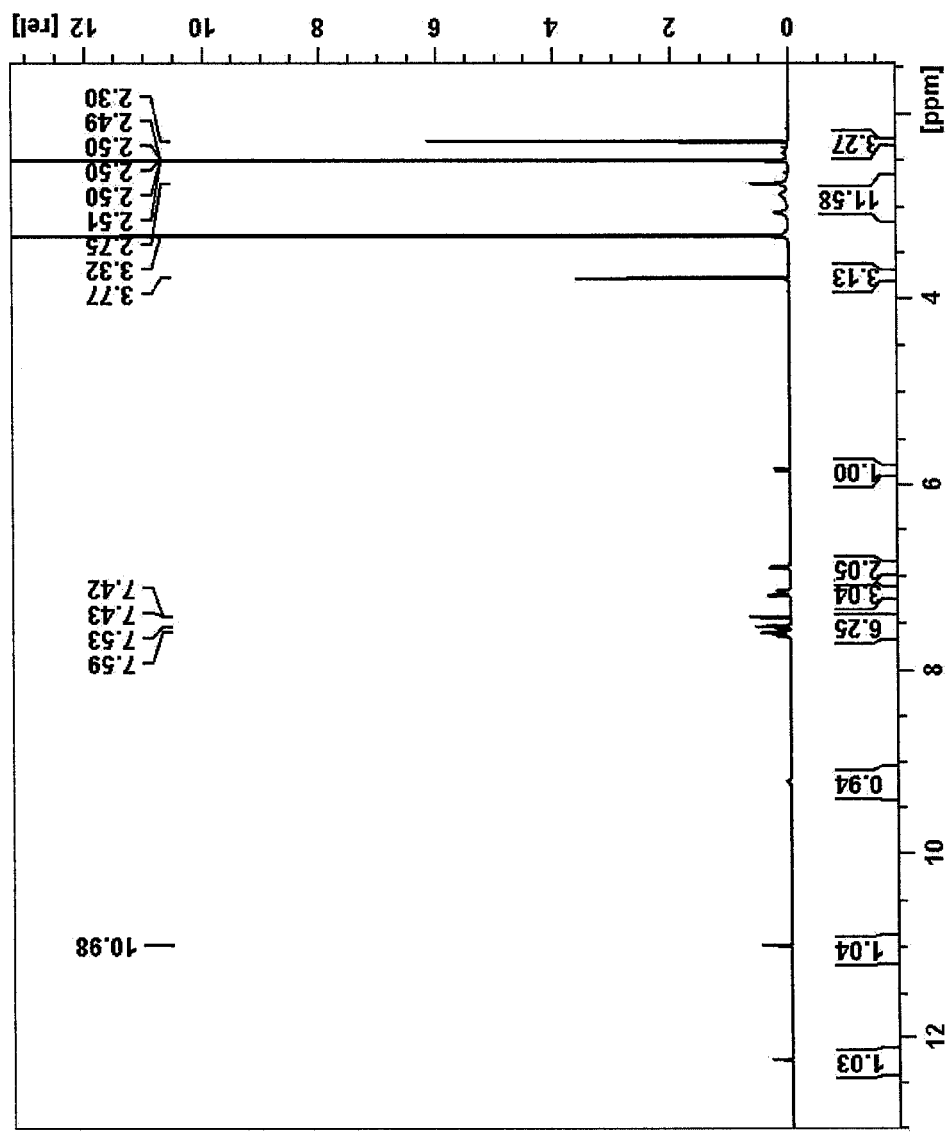
FIG. 6 is a $^1$H-NMR spectrum of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate and methanesulfonic acid salt prepared according to Example 1.

$^1$H-NMR spectrum was measured (FIG. 6) and confirmed that the compound shows the structure with an API:methanesulfonic acid stoichiometry of 1:1.

Example 2

Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate methanesulfonic acid salt 7000 mg (13 mmol) of intedanib free base was suspended in 80 mL of methanol and was heated to 50° C. The solution of 2500 mg Methanesulfonic acid (>98%) in 2 mL of methanol (26 mol) was added dropwise and a clear solution formed which precipitated within a minute.

The suspension was stirred at 50° C. for additional 1 hour and was cooled down slowly to 0° C. and was stirred at that temperature for additional 2 hours.

The product was filtered through a glass filter and was washed with 10 mL of methanol.

Product: 8840 mg
Yield: 93%
HPLC: 99.8%

XRPD pattern was measured (FIG. 7) and showed that the compound is in a crystalline state that was designated as Crystal modification 2 of intedanib methanesulfonic acid salt.

Figure 12:
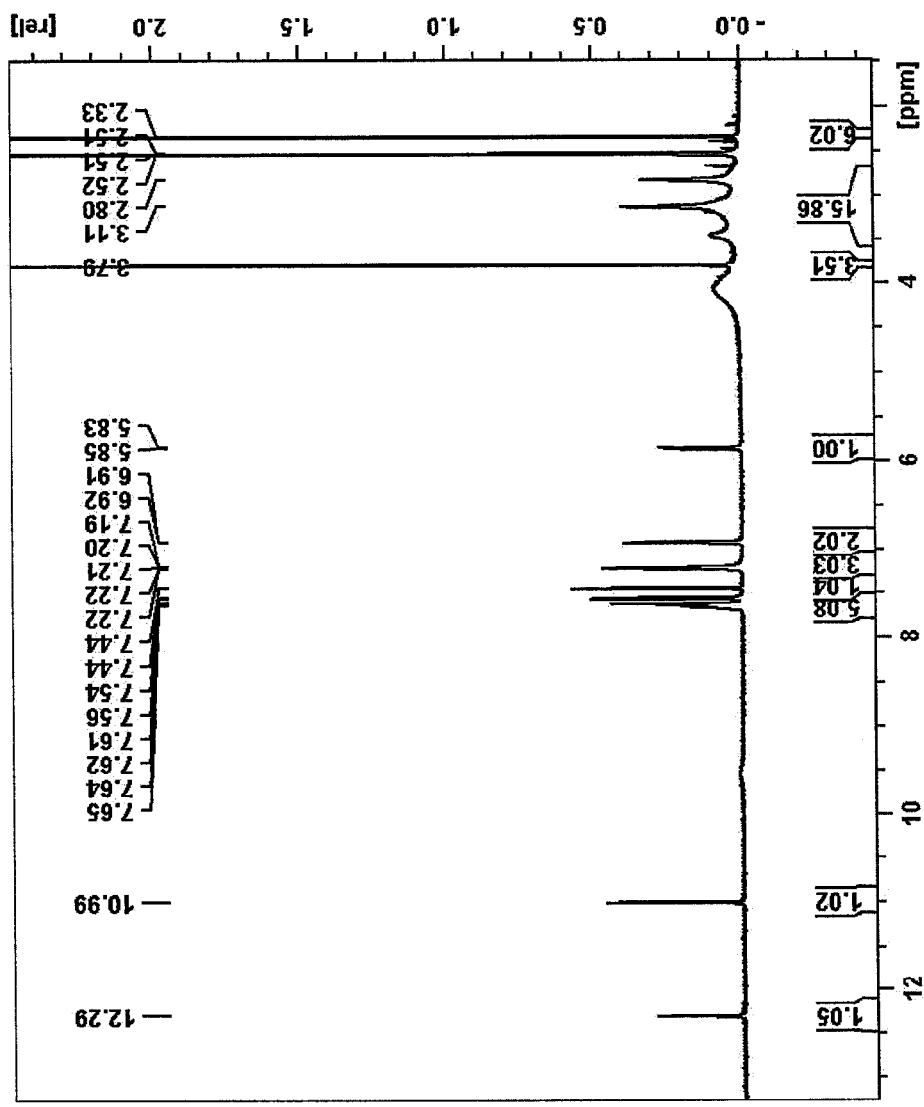
FIG. 12 is a $^1$H-NMR spectrum of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate and methanesulfonic acid salt prepared according to Example 2.

$^1$H-NMR spectrum was measured (FIG. 12) and confirmed that the compound shows the structure with an API:methanesulfonic acid stoichiometry of 1:2.

Example 3

Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt 7000 mg (13 mmol) of intedanib free base was suspended in 70 mL of methyl ethyl ketone and was heated to 50° C. The solution of 2715 mg p-toluenesulfonic acid in 4 mL of water (13 mmol) was added dropwise and a clear solution formed which precipitated within a minute.

The suspension was stirred at 50° C. for additional 1 hour and was cooled down slowly to 0° C. and was stirred at that temperature for additional 2 hours.

The product was filtered through a glass filter and was washed with 5 mL of methyl ethyl ketone.

Product: 8160 mg
Yield: 86%
HPLC: 99.8%

XRPD pattern was measured (FIG. 13) and showed that the compound is in a crystalline state that was designated as Crystal modification 1 of intedanib p-toluenesulfonic acid salt.

Figure 18:
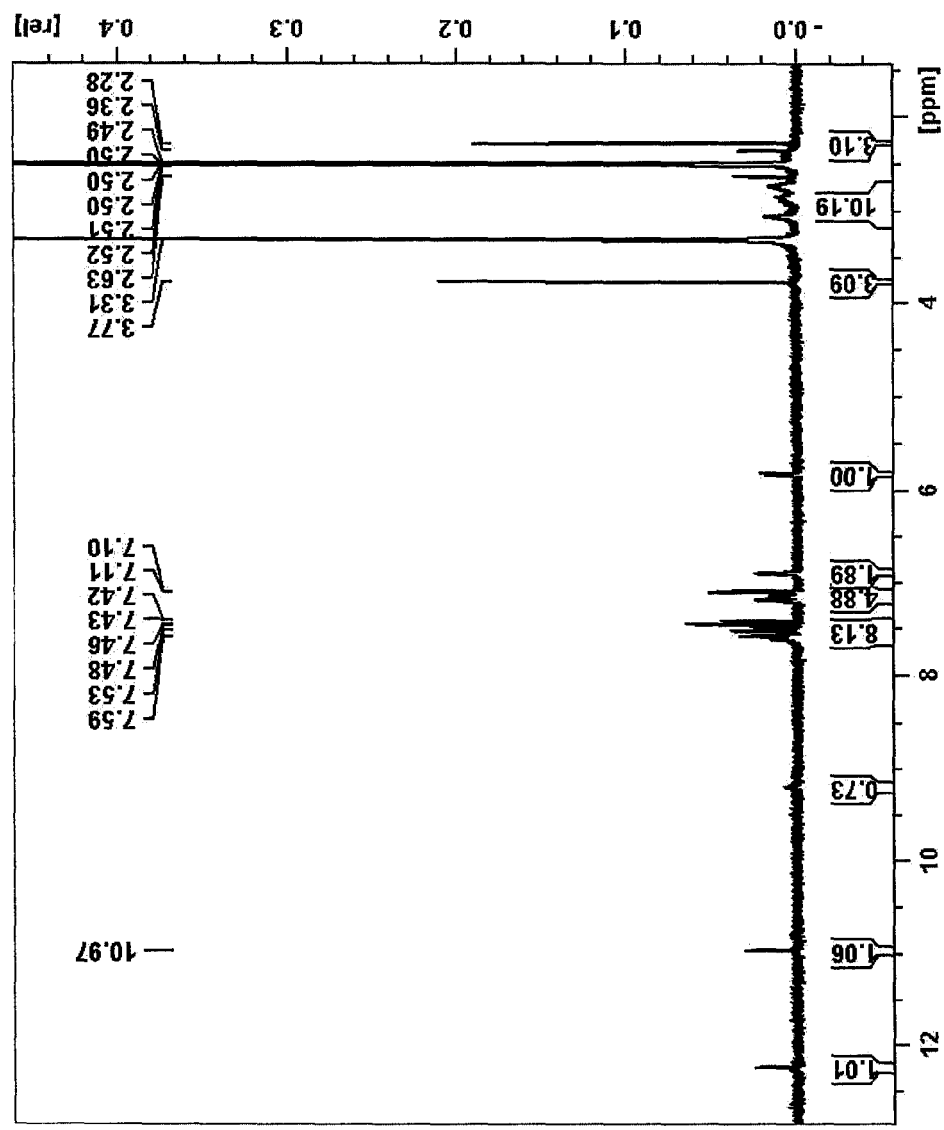
FIG. 18 is a $^1$H-NMR spectrum of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate and p-toluenesulfonic acid salt prepared according to Example 3.

$^1$H-NMR spectrum was measured (FIG. 18) and confirmed that the compound shows the structure with an API:p-toluenesulfonic acid stoichiometry of 1:1.

Example 4

Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt 300 mg (0.56 mmol) of intedanib free base was suspended in 5 mL of ethanol and was heated to 50° C.

The solution of 106 mg (0.56 mmol) p-toluenesulfonic acid in 2 mL of ethanol was added dropwise and a clear solution formed which precipitated within a minute.

The suspension was stirred at 50° C. for additional 1 hour and was cooled down slowly to 0° C. and was stirred at that temperature for additional 2 hours.

The product was filtered through a glass filter and was washed with 2 mL of ethanol.

Product: 345 mg
Yield: 85%
HPLC: 99.8%

XRPD pattern was measured (FIG. 19) and showed that the compound is in a crystalline state that was designated as Crystal modification 2 of intedanib p-toluenesulfonic acid salt.

$^1$H-NMR spectrum was measured (FIG. 24) and showed that the compound confirms the structure with an API:p-toluenesulfonic acid stoichiometry of 1:1.

Example 5

Crystal modification 2 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate p-toluenesulfonic acid salt 200 mg (0.274 mmol) of intedanib p-toluenesulfonic acid salt was suspended in 1 mL of ethanol at room temperature. The suspension was kept in closed vessel at room temperature applying a continuous stirring for 72 hours.

The solid obtained was collected by filtration and dried by vacuum suction at 40° C.

XRPD pattern was measured (FIG. 19) and showed that the compound is in a crystalline state that was designated as Crystal modification 2 of intedanib p-toluenesulfonic acid salt.

Example 6

Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate L-tartaric acid salt 7000 mg (13 mmol) of intedanib free base was suspended in 70 mL of methyl ethyl ketone and was heated to 50° C. The solution of 1070 mg L-tartaric acid in 4 mL of water (6.5 mmol) was added dropwise and a clear solution formed which precipitated within a minute.

The suspension was stirred at 50° C. for additional 1 hour and was cooled down slowly to 0° C. and was stirred at that temperature for additional 16 hours.

The product was filtered through a glass filter and was washed with 10 mL of methyl ethyl ketone.

Product: 7850 mg
Yield: 98%
HPLC: 99.7%

XRPD pattern was measured (FIG. 25) and showed that the compound is in a crystalline state that was designated as Crystal modification 1 of intedanib L-tartaric acid salt.

$^1$H-NMR spectrum was measured (FIG. 30) and confirmed that the compound shows the structure with an API:L-tartaric acid stoichiometry of 2:1.

Example 7

Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate L-tartaric acid salt 200 mg (0.325 mmol) of intedanib L-tartaric acid salt was suspended in 1 mL of methyl ethyl ketone at room temperature. The suspension was kept in closed vessel at room temperature applying a continuous stirring for 72 hours.

The solid obtained was collected by filtration and dried by vacuum suction at 40° C.

XRPD pattern was measured (FIG. 25) and showed that the compound is in a crystalline state that was designated as Crystal modification 1 of intedanib L-tartaric acid salt.

Example 8

Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate maleic acid salt 7000 mg (13 mmol) of intedanib free base was suspended in 70 mL of ethyl acetate and was heated to 50° C. The solution of 1650 mg maleic acid in 3 mL of water (13 mmol) was added dropwise and a clear solution formed which precipitated within a minute.

The suspension was stirred at 50° C. for additional 1 hour and was cooled down slowly to 0° C. and was stirred at that temperature for additional 2 hours.

The product was filtered through a glass filter and was washed with 5 mL of ethyl acetate.

Product: 8190 mg
Yield: 96%
HPLC: 99.8%

XRPD pattern was measured (FIG. 31) and showed that the compound is in a crystalline state that was designated as Crystal modification 1 of intedanib maleic acid salt.

$^1$H-NMR spectrum was measured (FIG. 36) and confirmed that the compound shows the structure with an API:maleic acid stoichiometry of 1:1.

Example 9

Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate acetic acid salt 300 mg (0.56 mmol) of intedanib free base was suspended in 5 mL of methyl ethyl ketone and was heated to 50° C. 34 µl (0.56 mmol) of acetic acid (>99%) was added and a clear solution formed which was cooled down to 0° C. and seeded. The suspension was stirred at 0° C. for additional 16 hours.

The product was filtered through a glass filter and was washed with 0.5 mL of methyl ethyl ketone.

Product: 210 mg
Yield: 64%
HPLC: 99.7%

XRPD pattern was measured (FIG. 37) and showed that the compound is in a crystalline state that was designated as Crystal modification 1 of intedanib acetic acid salt.

¹H-NMR spectrum was measured (FIG. 42) and confirmed that the compound shows the structure with an API:acetic acid stoichiometry of 1:1.

Example 10

Crystal modification 1 of methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate phosphoric acid salt 300 mg (0.56 mmol) of intedanib free base was suspended in 5 mL of ethyl acetate and was heated to 50° C. 40 μl (0.56 mmol) of phosphoric acid (85%) was added and a clear solution formed which precipitated within a minute. The suspension was slowly cooled down to 0° C. and stirred at 0° C. for additional 16 hours.

The product was filtered through a glass filter and was washed with 0.5 mL of ethyl acetate Product: 250 mg
Yield: 70%
HPLC: 99.8%

XRPD pattern was measured (FIG. 43) and showed that the compound is in a crystalline state that was designated as Crystal modification 1 of intedanib phosphoric acid salt.

¹H-NMR spectrum was measured (FIG. 48) and confirmed that the compound shows the structure with an API:phosphoric acid stoichiometry of 1:1.

The invention claimed is:

1. A salt comprising methyl (3Z)-3-{[(4-{methyl[(4-methylpiperazin-1-yl)acetyl]amino}phenyl)amino]-(phenyl)methylidene}-2-oxo-2,3-dihydro-1H-indole-6-carboxylate of Formula I and at least one acid component (HX), wherein the acid addition salt is a hemihydrate in a crystalline form and the acid component (HX) is a mono-methanesulphonic acid, characterized by an X-ray powder diffraction pattern that comprises characteristic peaks at about 9.8; 14.1; 17.2; 20.0 and 22.8°±0.2° 2-theta measured by CuKα radiation

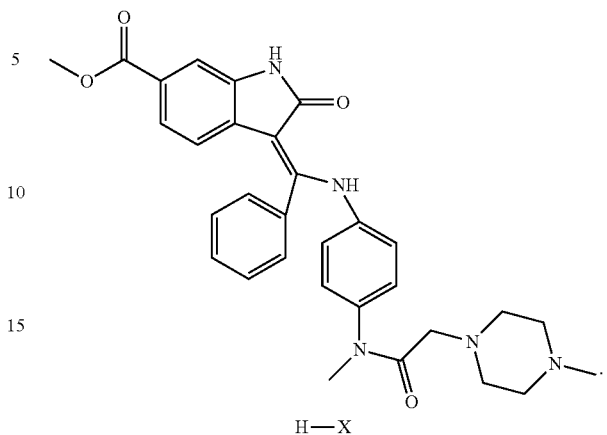

(I)

2. A method for preparing the Crystal modification 1 of the salt as defined in claim 1, comprising the following steps:
a. suspending intedanib free base in a polar protic solvent at 60° C.;
b. drop-wise addition of the aqueous solution of the methanesulfonic acid, resulting in a clear solution;
c. stirring the solution of step b. at 60° C. for additional 1 hour;
d. cooling the solution of step c. to 44° C. where it is seeded and precipitation occurs;
e. cooling the suspension of step d. to 0-5° C.;
f. keeping the suspension of step e. for 16 hours at a temperature of 0-5° C.;
g. isolating the intedanib methanesulfonic acid salt in Crystal modification 1; and
h. optionally, drying the product of step g. under the laboratory conditions until the constant weight of the product is reached.

* * * * *